(12) United States Patent
Cannizzaro et al.

(10) Patent No.: US 9,610,299 B2
(45) Date of Patent: *Apr. 4, 2017

(54) COMPOUNDS FOR THE TREATMENT OF ADDICTION

(71) Applicant: Gilead Sciences, Inc., Foster City, CA (US)

(72) Inventors: Carina E. Cannizzaro, Foster City, CA (US); Michael Graupe, Foster City, CA (US); Juan A. Guerrero, Concord, CA (US); Yafan Lu, Foster City, CA (US); Robert G. Strickley, San Mateo, CA (US); Chandrasekar Venkataramani, Redwood City, CA (US); Jeff Zablocki, Los Altos, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/659,042

(22) Filed: Mar. 16, 2015

(65) Prior Publication Data

US 2015/0250805 A1 Sep. 10, 2015

Related U.S. Application Data

(60) Continuation of application No. 13/966,029, filed on Aug. 13, 2013, now Pat. No. 9,000,015, which is a division of application No. 13/537,536, filed on Jun. 29, 2012, now Pat. No. 8,558,001.

(60) Provisional application No. 61/503,923, filed on Jul. 1, 2011.

(51) Int. Cl.
*A61K 31/675* (2006.01)
*C07D 213/64* (2006.01)
*C07F 9/58* (2006.01)
*A61K 31/4418* (2006.01)

(52) U.S. Cl.
CPC ........ *A61K 31/675* (2013.01); *A61K 31/4418* (2013.01); *C07D 213/64* (2013.01); *C07F 9/581* (2013.01); *C07F 9/584* (2013.01)

(58) Field of Classification Search
CPC .............................. C07D 213/62; A61K 31/47
USPC .......................................... 546/300; 514/314
See application file for complete search history.

(56) References Cited

U.S. PATENT DOCUMENTS

| 8,558,001 | B2 | 10/2013 | Cannizzaro et al. | |
| 8,575,353 | B2 * | 11/2013 | Cannizzaro et al. | 546/300 |
| 9,000,015 | B2 * | 4/2015 | Cannizzaro et al. | 514/351 |
| 2008/0032995 | A1 | 2/2008 | Zablocki et al. | |
| 2008/0207610 | A1 | 8/2008 | Zablocki et al. | |
| 2009/0209533 | A1 | 8/2009 | Zablocki et al. | |
| 2011/0105602 | A2 | 5/2011 | Mochly-Rosen et al. | |
| 2013/0079328 | A1 | 3/2013 | Cheng et al. | |

FOREIGN PATENT DOCUMENTS

| WO | WO-2008014497 A2 | 1/2008 |
| WO | WO-2008112164 A2 | 9/2008 |
| WO | WO-2009094028 A1 | 7/2009 |
| WO | WO 2009/134400 A1 | 11/2009 |
| WO | WO-2010028175 A1 | 3/2010 |
| WO | WO-2010062308 A1 | 6/2010 |
| WO | WO 2012/003189 A1 | 1/2012 |

OTHER PUBLICATIONS

Chen, C. et al., (2008) "Activation of Aldehyde Dehydrogenase-2 Reduces Ischemic Damage to the Heart" www.sciencemag.org 321:1493-1495.
Gao, G. et al. (2001) "Synthesis of Potential Antidipsotropic Isoflavones: Inhibitors of the Mitochondrial Monoamine Oxidase-Aldehyde Dehydrogenase Pathway" *Journal of Medicinal Chemistry* 44(20):3320-3328.
Dick et al., (2006) "The Genetics of Alcohol and other Drug Dependence" *Alcohol Research and Health* 31(2): 111-118.
Gao, G. et al. (2003) "Synthesis of Daidzin Analogues as Potential Agents for Alcohol Abuse" *Bioorganic & Medicinal Chemitry* 11:4069-4081.
Keung et al. (1993) "A Potent, Selective Inhibitor of Human Mitochondrial Aldehyde Dehydrogenase" *Proceedings of the National Academy of Sciences of the USA* 90:1247-1251.
Keung et al. (1998) "Kudzu Root: An Ancient Chinese Source of Modern Antidipsotropic Agents" *Phytochemistry* 47(4):499-506.
Keung (2003) "Anti-Dispotropic Isoflavones: The Potential Therapeutic Agents for Alcohol Dependence" *Medicinal Research Reviews* 23(4):669-696.

(Continued)

*Primary Examiner* — David K O'Dell
(74) *Attorney, Agent, or Firm* — Sheppard Mullin Richter & Hampton LLP

(57) ABSTRACT

Disclosed are novel compounds having the structure of Formula (I):

Formula (I)

which are useful for treating mammals for dependence upon substances of addiction, for example addiction to a dopamine-producing agent such as cocaine, morphine, amphetamines, nicotine, and/or alcohol. Also disclosed are pharmaceutical compositions comprising a therapeutically effective amount of a compound of Formula (I) and methods of using the compounds of Formula (I) in the treatment of addiction to a dopamine-producing agent.

3 Claims, 7 Drawing Sheets

(56) References Cited

OTHER PUBLICATIONS

Keung et al. (1993) "Daidzin and Daidzein Suppress Free-choice Ethanol Intake by Syrian Golden Hamsters" *Proceedings of the National Academy of Sciences of the USA* 90:10008-10012.
Lowe et al. (2008) "Structure of Daidzin, a Naturally Occurring Anti-Alcohol-Addiction Agent, in Complex with Human Mitochondrial Aldehyde Dehydrogenase" *Journal of Medicinal Chemistry* 51:4482-4487.
Luo et al., (2006) "Diplotype Trend Regression Analysis of the ADH Gene Cluster and the ALDH2 Gene: Multiple Significant Associates with Alcohol Dependence", *The American Journal of Human Genetics*, 78; 973-987.
Perez-Miller et al. (2010) "Alda-1 is an Agonist and Chemical Chaperone for the Common Human Aldehyde Dehydrogenase 2 Variant" *Nature Structural & Molecular Biology* 17(2):159-165.
Rooke et al. (2000) "The Mitochondrial Monoamine Oxidase-Aldehyde Dehydrogenase Pathway: A Potential Site of Action of Daidzin" *Journal of Medicinal Chemistry* 43(22):4169-4179.
International Search Report for PCT/US2012/044809, International Filing Date Jun. 29, 2012, mailed Aug. 13, 2012.
Office Action dated Mar. 14, 2013 Pakistan Patent Application No. 427/2012.
Communication pursuant to Rules 161(1) and 162 in European Application No. 12735394.4 dated Mar. 14, 2014, (2 pages).
English Translation of Decision of Rejection in Taiwan Application No. 101122794 dated Nov. 12, 2014, (2 pages).
English Translation of First Examination Report in Chilean Application No. 3597-2013 dated Sep. 10, 2015, (10 pages).
English Translation of First Office Action in Chinese Application No. 201280032944.6 dated Oct. 10, 2014, (7 pages).
English Translation of First Office Action in Ukraine Application No. a 2013 14148 dated Jan. 5, 2015, (3 pages).
English Translation of Notification No. 12880/SHTT-SC3 in Vietnam Application No. 1-2013-04100 dated Apr. 24, 2014, (1 page).
English Translation of Office Action in Bolivia Application No. SP-0209-2012 dated May 21, 2015, (10 pages).
English Translation of Office Action in Israel Application No. 230657 dated Aug. 31, 2015, (4 pages).
English Translation of Office Action in Korean Application No. 2014-7002302 dated Jul. 16, 2015, (4 pages).
English Translation of Office Action in Mexican Application No. MX/a/2013/014938 dated Aug. 19, 2015, (3 pages).
English Translation of Office Action in Taiwan Application No. 101122794 dated Mar. 21, 2014, (4 pages).
English Translation of Office Action in Thailand Application No. 1301007250 dated Oct. 20, 2015, (2 pages).
English Translation of Official Action in Eurasian Application No. 201391635 dated Jan. 30, 2014, (3 pages).
English Translation of Opposition in Bolivia Application No. SP-0209-2012 dated Mar. 20, 2014, (5 pages).
English Translation of Second Office Action in Chinese Application No. 201280032944.6 dated Apr. 13, 2015, (5 pages).
English Translation of Third Office Action in Chinese Application No. 201280032944.6 dated Jun. 23, 2015, (4 pages).
First Examination Report in Australia Application No. 2012279332 dated Feb. 11, 2014, (2 pages).
First Examination Report in New Zealand Application No. 618537 dated Oct. 16, 2014, (2 pages).
International Preliminary Report on Patentability for PCT Application No. PCT/US2012/044809 dated Jan. 7, 2014, (7 pages).
Official Action in Colombian Application No. 13-295.408 dated Apr. 24, 2015, (6 pages).
Examination and Search Report in African Regional Industrial Property Organization Application No. AP/P/2013/007282 dated Jul. 14, 2015, (4 pages).
Subsequent Substantive Examination Report in Philippines Application No. 1-2013-502674 dated Jan. 7, 2015, (1 page).
Substantive Examination Report in Philippines Application No. 1-2013-502674 dated Oct. 9, 2014, (1 page).
English translation of Official Action in Japanese Application No. 2014-519122 dated Dec. 8, 2015, (5 pages).
English translation of Second Office Action in Eurasian Application No. 201391635 dated May 20, 2015, (2 pages).
Extended European Search Report in European Application No. 15184883.5 dated Dec. 9, 2015, (7 pages).
English translation of First Official Action in Moldova Patent Application No. a20140009 dated May 12, 2016, 2 pages.
Non-Final Rejection in U.S. Appl. No. 13/537,536 dated May 17, 2013, 8 pages.
Non-Final Rejection in U.S. Appl. No. 13/791,422 dated May 17, 2013, 8 pages.
English translation of Second Office Action in Chilean Patent Application No. 2013-03597 dated Apr. 13, 2016, 14 pages.
English translation of Notice of Final Rejection in Korean Patent Application No. 2014-7002302 dated May 31, 2016, 5 pages.
Further Examination Report in New Zealand Application No. 618537 dated Feb. 5, 2016, 2 pages.

\* cited by examiner

Oral compound of Example 5 significantly reduced alcohol self administration

Cocaine cue reinstatement study design

Oral compound of Example 2 significantly inhibited cocaine cue reinstatement

Oral compound of Example 5 significantly inhibited cocaine cue reinstatement

Oral compound of Example 2 significantly reduced nicotine self administration

Acute oral Compound of Example 5 significantly reduced nicotine self administration

Chronic oral Compound of Example 5 significantly reduced nicotine self administration

COMPOUNDS FOR THE TREATMENT OF ADDICTION

CROSS-REFERENCE TO RELATED APPLICATIONS

This application is a continuation of U.S. patent application Ser. No. 13/966,029, filed Aug. 13, 2013, now U.S. Pat. No. 9,000,015, which is a divisional of U.S. patent application Ser. No. 13/537,536, filed Jun. 29, 2012, now U.S. Pat. No. 8,558,001, which claims the benefit under 35 U.S.C. §119(e) to U.S. Provisional application Ser. No. 61/503,923, filed Jul. 1, 2011, the entireties of which are hereby incorporated by reference.

FIELD

The present disclosure relates to novel human mitochondrial aldehyde dehydrogenase (ALDH-2) inhibitors and their use in treating mammals for their dependence upon drugs of addiction, such as an addiction to dopamine-producing agents like cocaine, opiates, amphetamines, nicotine, and alcohol. The disclosure further relates to methods for the use of such compounds, and to pharmaceutical compositions containing them.

BACKGROUND

Today, dependence upon drugs of addiction causes major health problems worldwide. For example, alcohol abuse and alcohol dependency can cause liver, pancreatic and kidney disease, heart disease, including dilated cardiomyopathy, polyneuropathy, internal bleeding, brain deterioration, alcohol poisoning, increased incidence of many types of cancer, insomnia, depression, anxiety, and even suicide. Heavy alcohol consumption by a pregnant mother can also lead to fetal alcohol syndrome, which is an incurable condition. Additionally, alcohol abuse and alcohol dependence are major contributing factors for head injuries, motor vehicle accidents, violence and assaults, and other neurological and other medical problems.

Addiction to nicotine is estimated by the National Institute on Drug Abuse to kill nearly 500,000 Americans every year. This total represents about 1 in 6 of all deaths in the U.S. caused by any means, and is more than the total of deaths caused by use of alcohol, cocaine, heroin, suicide, car accidents, fire and AIDS combined. Cigarette smoking is the most popular method of using nicotine, but there are also smokeless tobacco products such as snuff and chewing tobacco.

Nicotine addiction is linked to disease states such as leukemia, cataracts, and pneumonia; it is the cause of about one-third of all cancer deaths, the foremost of which is lung cancer. In addition to cancer, cigarette smoking also causes lung diseases, such as bronchitis and emphysema; it exacerbates asthma symptoms, and is the cause of chronic obstructive pulmonary diseases in general. It is also well known that cigarette smoking increases the risk of cardiovascular diseases, including stroke, heart attack, vascular disease, aneurysm, and the like.

Another major health problem is caused by cocaine abuse. Physical effects of cocaine use include constricted blood vessels, dilated pupils, and increased temperature, heart rate, and blood pressure. A user of cocaine can experience acute cardiovascular or cerebrovascular emergencies, such as a heart attack or stroke, potentially resulting in sudden death. Other complications associated with cocaine use include disturbances in heart rhythm, chest pain and respiratory failure, seizures, headaches, and gastrointestinal complications such as abdominal pain and nausea. Because cocaine has a tendency to decrease appetite, many chronic users can become malnourished. Repeated use of cocaine may lead to a state of increasing irritability, restlessness, and paranoia. This can result in a period of full-blown paranoid psychosis, in which the user loses touch with reality and experiences auditory hallucinations. Moreover, it is well known that the concurrent abuse of nicotine, cocaine and alcohol is common. It has been found that the combination of cocaine and alcohol exerts more cardiovascular toxicity in humans than either drug alone.

Historically, treating chemical dependence largely involved attempts to persuade patients to discontinue use the substance voluntarily (behavioral therapy). However, cocaine, morphine, amphetamines, nicotine, and alcohol, and other types of dopamine-producing agents are highly addictive substances, and dependence upon such drugs can be harder to break and is significantly more damaging than dependence on most other addictive substances. In particular, alcohol, cocaine, and heroin dependence are typically chronic relapsing disorders.

There has been some moderate success in providing effective treatments for tobacco addiction by the use of nicotine replacement therapy, such as nicotine gum or the nicotine transdermal patch. Additionally, antidepressants and antihypertensive drugs have been tried, with modest success. Attempts have also been made to treat tobacco addiction by persuading patients to discontinue the use of tobacco voluntarily (behavioral therapy), but this method has not proved to be very successful. Accordingly, it is clearly desirable to find a treatment for tobacco addiction that reduces or prevents the craving for nicotine that does not involve nicotine replacement therapy or the use of antidepressants and antihypertensive drugs.

Accordingly, there has been much interest in the scientific community in attempting to find substances that could be employed to ameliorate dependency on addictive agents. Compounds that have previously been employed for the treatment of alcohol abuse include disulfiram (Antabuse™), cyanamide, naltrexone; and acamprosate.

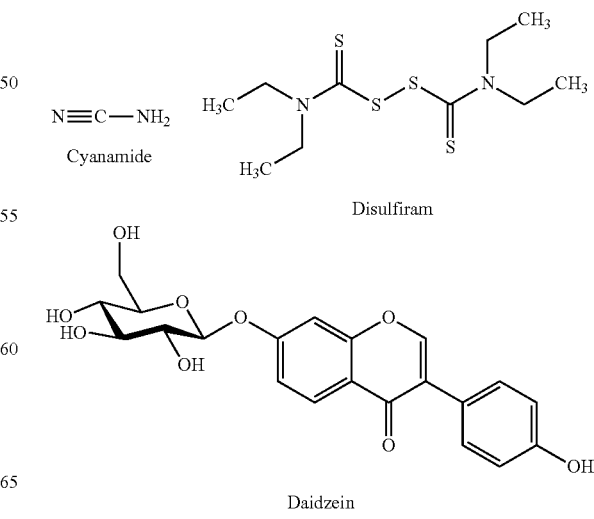

-continued

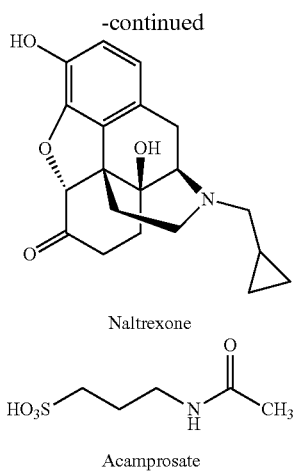

Naltrexone

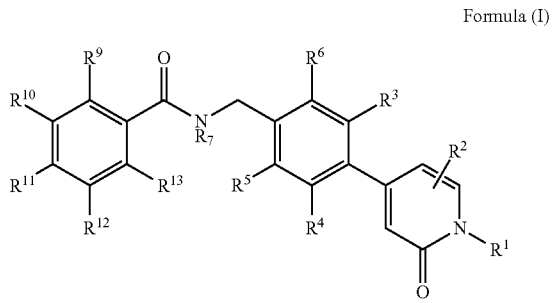

Acamprosate

Naltrexone, a classical opiate antagonist, appears to act by reducing alcohol craving in abstinent patients. The drug, however, is hepatotoxic and causes side-effects that often require medical intervention. Acamprosate, another approved drug, is thought to act by modulating glutamatergic systems. It only has moderate efficacy and serious side effects that include diarrhea, allergic reactions, irregular heartbeats, and low or high blood pressure. Disulfiram, an aldehyde dehydrogenase inhibitor, acts by interfering with the metabolic pathway of alcohol. Normally, alcohol is metabolized to acetaldehyde, which in turn is eliminated by oxidation to acetic acid by the enzyme aldehyde dehydrogenase. Disulfiram inhibits aldehyde dehydrogenase and thereby prevents oxidation of alcohol-generated acetaldehyde to acetic acid. Alcohol consumption during disulfiram treatment, however, leads to the accumulation of acetaldehyde, inducing unpleasant side-effects. Because disulfiram does not reduce craving for alcohol, success with the drug depends on a high level of patient motivation since patients who wish to drink can simply stop taking the drug. Additionally, it has been recently proposed that disulfiram can be used for the treatment of cocaine dependency (for example, see Bonet et al., *Journal of Substance Abuse Treatment*, 26 (2004), 225-232).

Recently it has been shown that an isoflavone known as daidzein and structurally related derivatives thereof are effective in suppressing ethanol intake. Daidzein is the major active component obtained from extracts of *Radix puerariae*, a traditional Chinese medication that suppresses ethanol intake in Syrian golden hamsters. See Keung, W. M. and Vallee, B. L. (1993) *Proc. Natl. Acad. Sci. USA* 90, 10008-10012 and Keung, W. M., Klyosov, A. A., and Vallee, B. L. (1997) *Proc. Natl. Acad. Sci. USA* 94, 1675-1679, and U.S. Pat. Nos. 5,624,910 and 6,121,010. U.S. Pat. Nos. 5,624,910 and 6,121,010 disclosed ether isoflavone derivatives of daidzein, which were shown to be effective in treating ethanol dependency.

Mechanistically, daidzein and its derivatives were shown to be potent and selective inhibitors of human mitochondrial aldehyde dehydrogenase (ALDH-2), which is an enzyme involved in the major enzymatic pathway responsible for ethanol metabolism in humans. It appears preferable that daidzein analogues inhibit ALDH-2 selectively relative to the monoamine oxidase (MAO) pathway because daidzein analogues that inhibit both ALDH-2 and MAO exhibited less antidipsotropic activity. Alternatively, WO 2008/014497 disclosed novel isoflavone derivatives that are selective ALDH-2 inhibitors with little effect on the MAO pathway and, thus, are useful for the treatment of alcohol dependency.

In view of the above-indicated discoveries, a demand has emerged for additional classes of compounds that are safe and effective for the treatment of alcohol dependency, but that are structurally distinct from disulfiram, cyanamide, naltrexone; acamprosate, daidzein, and analogs thereof. Ideally, such additional classes of compounds will also be useful for the treatment of other addictive agents such as cocaine, heroin, and nicotine, and in particular, ameliorate the tendency of abusers to relapse.

SUMMARY

Surprisingly, it has now been discovered that compounds of Formula (I) as described below, although structurally unrelated to known compounds for the treatment of addictive agents, are nonetheless effective for the treatment of alcohol dependency as determined from the model studies also described herein. Further, the compounds of Formula (I) are effective in the treatment of other addictive agents such as cocaine, heroin, and nicotine. In particular, the compounds of Formula (I) ameliorate the tendency of abusers to relapse. In certain aspects, the compounds of Formula (I) inhibit ALDH-2 selectively relative to the monoamine oxidase (MAO) pathway.

Accordingly, in certain aspects, is provided compounds of Formula (I):

Formula (I)

wherein:
$R^1$ is hydrogen, optionally substituted $C_{1-6}$ alkyl, —$CH_2OH$, —$CH_2OP(O)(OR^{20})(OR^{21})$;
$R^2$ is hydrogen, optionally substituted $C_{1-6}$ alkyl, cycloalkyl, or halo;
each of $R^3$, $R^4$, $R^5$, $R^6$, $R^9$, $R^{10}$, $R^{11}$, $R^{12}$ and $R^{13}$ is independently hydrogen, hydroxyl, —$OP(O)(OR^{20})$ $(OR^{21})$, —$CH_2OH$, —$CH_2OP(O)(OR^{20})(OR^{21})$, optionally substituted alkyl, optionally substituted alkylene, optionally substituted alkynyl, optionally substituted alkoxy, optionally substituted cycloalkyl, optionally substituted aryl, optionally substituted aralkyl, optionally substituted heteroaryl, optionally substituted heteroaralkyl, optionally substituted heterocyclyl, aminocarbonyl, acyl, acylamino, —O—($C_1$ to $C_6$-alkyl)-O—($C_1$ to $C_6$-alkyl), cyano, halo, —$SO_2NR^{24}R^{25}$; or —$NR^{24}R^{25}$;

$R^7$ is hydrogen or optionally substituted $C_{1-6}$ alkyl;

each of $R^{20}$ and $R^{21}$ is independently $Na^+$, $Li^+$, $K^+$, hydrogen, $C_{1-6}$ alkyl; or $R^{20}$ and $R^{21}$ can be combined to represent a single divalent cation $Zn^{2+}$, $Ca^{2+}$, or $Mg^{2+}$.

each of $R^{22}$ and $R^{23}$ is independently optionally substituted alkyl, optionally substituted alkoxy, optionally substituted cycloalkyl, optionally substituted aryl, or —$NR^{24}R^{25}$; and each of $R^{24}$ and $R^{25}$ is independently chosen from hydrogen or $C_{1-6}$ alkyl or when combined together with the nitrogen to which they are attached form a heterocycle; or a pharmaceutically acceptable salt, ester, single stereoisomer, mixture of stereoisomers, or tautomer thereof.

Provided is a compound of Formula (Ia):

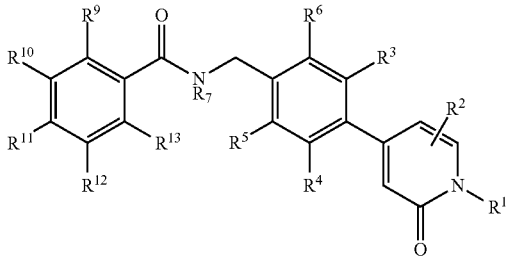

Formula (Ia)

wherein:

$R^1$ is hydrogen, optionally substituted $C_{1-6}$ alkyl, —$CH_2OH$, —$CH_2OP(O)(OR^{20})(OR^{21})$, —$C(O)R^{22}$, or —$SO_2R^{23}$;

$R^2$ is hydrogen, optionally substituted $C_{1-6}$ alkyl, cycloalkyl, or halo;

each of $R^3$, $R^4$, $R^5$, $R^6$, $R^9$, $R^{10}$, $R^{11}$, $R^{12}$ and $R^{13}$ is independently hydrogen, hydroxyl, —$OP(O)(OR^{20})(OR^{21})$, —$CH_2OH$, —$CH_2OP(O)(OR^{20})(OR^{21})$, optionally substituted alkyl, optionally substituted alkylene, optionally substituted alkynyl, optionally substituted alkoxy, optionally substituted cycloalkyl, optionally substituted aryl, optionally substituted aralkyl, optionally substituted heteroaryl, optionally substituted heteroaralkyl, optionally substituted heterocyclyl, aminocarbonyl, acyl, acylamino, —O—($C_1$ to $C_6$-alkyl)-O—($C_1$ to $C_6$-alkyl), cyano, halo, —$SO_2NR^{24}R^{25}$; or —$NR^{24}R^{25}$;

$R^7$ is hydrogen or optionally substituted $C_{1-6}$ alkyl;

each of $R^{20}$ and $R^{21}$ is independently $Na^+$, $Li^+$, $K^+$, hydrogen, $C_{1-6}$ alkyl; or $R^{20}$ and $R^{21}$ can be combined to represent a single divalent cation $Zn^{2+}$, $Ca^{2+}$, or $Mg^{2+}$.

each of $R^{22}$ and $R^{23}$ is independently optionally substituted alkyl, optionally substituted alkoxy, optionally substituted cycloalkyl, optionally substituted aryl, or —$NR^{24}R^{25}$; and each of $R^{24}$ and $R^{25}$ is independently chosen from hydrogen or $C_{1-6}$ alkyl or when combined together with the nitrogen to which they are attached form a heterocycle; or a pharmaceutically acceptable salt, ester, single stereoisomer, mixture of stereoisomers, or tautomer thereof.

Also provided is a compound of formula (Ib)

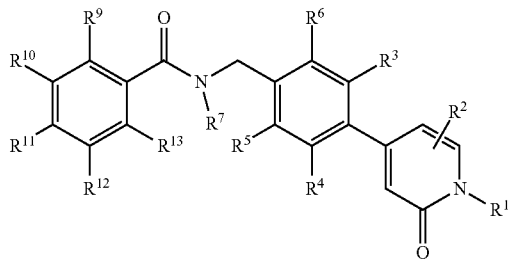

Formula (Ib)

wherein:

$R^1$ is hydrogen, $C_{1-6}$ alkyl, —$CH_2OR^{22}$, —$CH_2OP(O)(OR^{20})(OR^{21})$;

$R^2$ is hydrogen, cyano, $C_{1-6}$ alkyl, $C_3$-$C_6$ cycloalkyl, or halo;

each of $R^3$, $R^4$, $R^5$, $R^6$, $R^9$, $R^{10}$, $R^{11}$, $R^{12}$ and $R^{13}$ is independently hydrogen, halo, $C_1$-$C_6$ alley, hydroxyl, or —$CH_2OR^{22}$;

$R^7$ is hydrogen or $C_{1-6}$ alkyl;

each of $R^{20}$ and $R^{21}$ is independently $Na^+$, $Li^+$, $K^+$, hydrogen, or $C_{1-6}$ alkyl;

each $R^{22}$ is independently hydrogen, $C_1$-$C_6$ alkyl, $C_3$-$C_6$ cycloalkyl, phenyl or benzyl; or a pharmaceutically acceptable salt, single stereoisomer, mixture of stereoisomers, or tautomer thereof.

Also provided is a compound of formula II

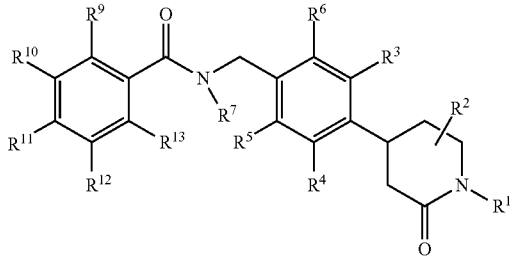

Formula (II)

wherein:

$R^1$ is hydrogen, —$CH_2OH$, —$CH_2OP(O)(OR^{20})(OR^{21})$, or optionally substituted $C_{1-6}$ alkyl;

$R^2$ is hydrogen, halo, optionally substituted lower $C_{1-6}$ alkyl, or optionally substituted cycloalkyl;

each of $R^3$, $R^4$, $R^5$, $R^6$, $R^9$, $R^{10}$, $R^{11}$, $R^{12}$ and $R^{13}$ is independently hydrogen, hydroxyl, —$OP(O)(OR^{20})(OR^{21})$, —$CH_2OH$, —$CH_2OP(O)(OR^{20})(OR^{21})$, aminocarbonyl, acyl, acylamino, —O—($C_1$ to $C_6$-alkyl)-O—($C_1$ to $C_6$-alkyl), cyano, halo, —$SO_2NR^{24}R^{25}$, —$NR^{24}R^{25}$, optionally substituted alkyl, optionally substituted alkylene, optionally substituted alkynyl, optionally substituted alkoxy, optionally substituted cycloalkyl, optionally substituted aryl, optionally substituted aralkyl, optionally substituted heteroaryl, optionally substituted heteroaralkyl, or optionally substituted heterocyclyl;

$R^7$ is hydrogen or optionally substituted $C_{1-6}$ alkyl;

each of $R^{20}$ and $R^{21}$ is independently $Na^+$, $Li^+$, $K^+$, hydrogen, $C_{1-6}$ alkyl; or $R^{20}$ and $R^{21}$ can be combined to represent a single divalent cation $Zn^{2+}$, $Ca^{2+}$, or $Mg^{2+}$.

each of $R^{22}$ and $R^{23}$ is independently optionally substituted alkyl, optionally substituted alkoxy, optionally substituted cycloalkyl, optionally substituted aryl, or —$NR^{24}R^{25}$; and each of $R^{24}$ and $R^{25}$ is independently chosen from hydrogen or $C_{1-6}$ alkyl or when combined together with the nitrogen to which they are attached form a heterocycle; or a pharmaceutically acceptable salt, ester, single stereoisomer, mixture of stereoisomers, or tautomer thereof.

In certain aspects, the disclosure provides pharmaceutical compositions comprising a therapeutically effective amount of a compound of the disclosure (e.g. a compound of Formula (I) or a pharmaceutically acceptable salt, ester, prodrug, stereoisomer, solvate, or hydrate thereof and at least one pharmaceutically acceptable carrier).

In certain aspects, is provided methods of using the compounds of Formula (I) in the treatment of addiction to a dopamine-producing agent. The method comprises administering to a mammal in need thereof a therapeutically effective dose of a compound of Formula (I). Such diseases include, but are not limited to, the treatment of dependency upon cocaine, opiates, amphetamines, nicotine, and alcohol.

Compounds of Formula (I), (Ia), (Ib) or (II) include, but are not limited to:
2,6-dichloro-4-(2-methoxyethoxy)-N-(4-(2-oxo-1,2-dihydropyridin-4-yl)benzyl)benzamide (1);
2,6-dichloro-N-[4-(2-oxo-1,2-dihydro-pyridin-4-yl)-benzyl]-benzamide (2);
2-chloro-3-fluoro-N-(4-(2-oxo-1,2-dihydropyridin-4-yl)benzyl)benzamide (3);
2-chloro-6-methyl-N-(4-(2-oxo-1,2-dihydropyridin-4-yl)benzyl)benzamide (4);
2,6-dimethyl-N-(4-(2-oxo-1,2-dihydropyridin-4-yl)benzyl)benzamide (5);
2,6-dichloro-N-[4-(6-methyl-2-oxo-1,2-dihydro-pyridin-4-yl)-benzyl]-benzamide (6);
2-chloro-3,6-difluoro-N-(4-(2-oxo-1,2-dihydropyridin-4-yl)benzyl)benzamide (7);
2,6-dichloro-N-(3-methyl-4-(2-oxo-1,2-dihydropyridin-4-yl)benzyl)benzamide (8);
2,6-dichloro-N-(4-(1-methyl-2-oxo-1,2-dihydropyridin-4-yl)benzyl)benzamide (9);
2,6-difluoro-N-(4-(2-oxo-1,2-dihydropyridin-4-yl)benzyl)benzamide (10);
2-chloro-6-fluoro-N-(4-(2-oxo-1,2-dihydropyridin-4-yl)benzyl)benzamide (11);
2,6-dichloro-N-(2-fluoro-4-(2-oxo-1,2-dihydropyridin-4-yl)benzyl)benzamide (12);
2,6-dichloro-N-(4-(5-fluoro-2-oxo-1,2-dihydropyridin-4-yl)benzyl)benzamide (13); and
phosphoric acid mono-(4-{4-[(2,6-dichloro-benzoylamino)-methyl]-phenyl}-2-oxo-2H-pyridin-1-ylmethyl) ester (14); or a pharmaceutically acceptable salt, ester, single stereoisomer, mixture of stereoisomers, or tautomer thereof.

Additional embodiments are described herein.

DETAILED DESCRIPTION

Before the present compositions and methods are described, it is to be understood that the disclosure is not limited to the particular compounds, compositions, methodologies, protocols, cell lines, assays, and reagents described, as these may vary. It is also to be understood that the terminology used herein is intended to describe particular embodiments, and is in no way intended to limit the scope as set forth in the appended claims.

DETAILED DESCRIPTION OF FIGURES

DEFINITIONS AND GENERAL PARAMETERS

Figure 1:
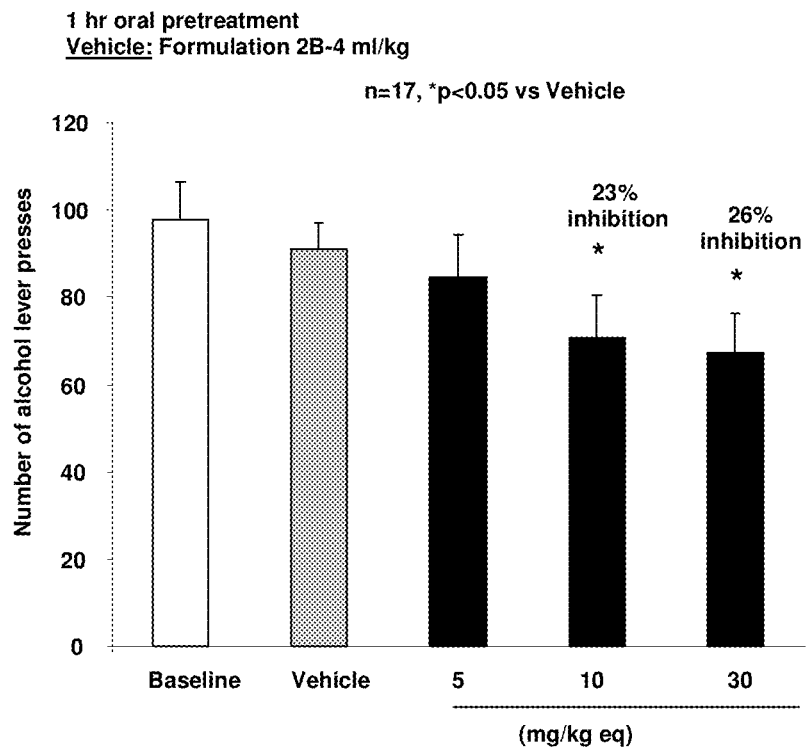
FIG. 1 shows significant reduction ($p<0.05$ versus vehicle) in alcohol self administration based on lever presses.

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having from 1 to 20 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:

1) an alkyl group as defined above, having 1, 2, 3, 4 or 5 substituents, (typically 1, 2, or 3 substituents) selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclyloxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2; or 2) an alkyl group as defined above that is interrupted by 1-10 atoms (e.g. 1, 2, 3, 4, or 5 atoms) independently chosen from oxygen, sulfur and $NR^a$, where $R^a$ is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, $CF_3$, amino, substituted amino, cyano, or —$S(O)_nR$, in which R is alkyl, aryl, or heteroaryl and n is 0, 1 or 2; or 3) an alkyl group as defined above that has both 1, 2, 3, 4 or 5 substituents as defined above and is also interrupted by 1-10 atoms (e.g. 1, 2, 3, 4, or 5 atoms) as defined above.

The term "lower alkyl" refers to a monoradical branched or unbranched saturated hydrocarbon chain having 1, 2, 3, 4, 5, or 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents (typically 1, 2, or 3 substituents), as defined for substituted alkyl, or a lower alkyl group as defined above that is interrupted by 1, 2, 3, 4, or 5 atoms as defined for substituted alkyl, or a lower alkyl group as defined above that has both 1, 2, 3, 4 or 5 substituents as defined above and is also interrupted by 1, 2, 3, 4, or 5 atoms as defined above.

The term "alkylene" refers to a diradical of a branched or unbranched saturated hydrocarbon chain, typically having from 1 to 20 carbon atoms (e.g. 1-10 carbon atoms, or 1, 2, 3, 4, 5 or 6 carbon atoms). This term is exemplified by groups such as methylene (—$CH_2$—), ethylene (—$CH_2CH_2$—), the propylene isomers (e.g., —$CH_2CH_2CH_2$— and —$CH(CH_3)CH_2$—), and the like.

The term "lower alkylene" refers to a diradical of a branched or unbranched saturated hydrocarbon chain, typically having 1, 2, 3, 4, 5, or 6 carbon atoms.

The term "substituted alkylene" refers to:
(1) an alkylene group as defined above having 1, 2, 3, 4, or 5 substituents (typically 1, 2, or 3 substituents) selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclyloxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2; or
(2) an alkylene group as defined above that is interrupted by 1-10 groups (e.g. 1, 2, 3, 4, or 5 groups) independently chosen from —O—, —S—, sulfonyl, —C(O)—, —C(O)O—, —C(O)N—, and —$NR^a$, where $R^a$ is chosen from hydrogen, optionally substituted alkyl, cycloalkyl, cycloalkenyl, aryl, heteroaryl and heterocyclyl; or
(3) an alkylene group as defined above that has both 1, 2, 3, 4 or 5 substituents as defined above and is also interrupted by 1-10 groups as defined above. Examples of substituted alkylenes are chloromethylene (—CH(Cl)—), aminoethylene (—CH($NH_2$)$CH_2$—), methylaminoethylene (—CH(NHMe)$CH_2$—), 2-carboxypropylene isomers (—$CH_2$CH($CO_2$H)$CH_2$—), ethoxyethyl (—$CH_2CH_2$O—$CH_2CH_2$—), ethylmethylaminoethyl (—$CH_2CH_2$—N($CH_3$)—$CH_2CH_2$—), 1-ethoxy-2-(2-ethoxy-ethoxy)ethane (—$CH_2CH_2$O—$CH_2CH_2$—O$CH_2CH_2$—), and the like.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "aralkyloxy" refers to the group —O-aralkyl. "Optionally substituted aralkyloxy" refers to an optionally substituted aralkyl group covalently linked to an optionally substituted alkylene group. Such aralkyl groups are exemplified by benzyloxy, phenylethyloxy, and the like.

The term "alkoxy" refers to the group R—O—, where R is optionally substituted alkyl or optionally substituted cycloalkyl, or R is a group —Y—Z, in which Y is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Typical alkoxy groups are alkyl-O— and include, by way of example, methoxy, ethoxy, n-propoxy, iso-propoxy, n-butoxy, tert-butoxy, sec-butoxy, n-pentoxy, n-hexyloxy, 1,2-dimethylbutoxy, and the like.

The term "lower alkoxy" refers to the group R—O— in which R is optionally substituted lower alkyl as defined above. This term is exemplified by groups such as methoxy, ethoxy, n-propoxy, iso-propoxy, n-butoxy, iso-butoxy, t-butoxy, n-hexyloxy, and the like.

The term "alkylthio" refers to the group R—S—, where R is as defined for alkoxy.

The term "alkenyl" refers to a monoradical of a branched or unbranched unsaturated hydrocarbon group typically having from 2 to 20 carbon atoms (more typically from 2 to 10 carbon atoms, e.g. 2 to 6 carbon atoms) and having from 1 to 6 carbon-carbon double bonds, e.g. 1, 2, or 3 carbon-carbon double bonds. Typical alkenyl groups include ethenyl (or vinyl, i.e. —CH=$CH_2$), 1-propylene (or allyl, —$CH_2$CH=$CH_2$), isopropylene (—C($CH_3$)=$CH_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having 1, 2, 3, 4 or 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, acyloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2.

The term "alkynyl" refers to a monoradical of an unsaturated hydrocarbon, typically having from 2 to 20 carbon atoms (more typically from 2 to 10 carbon atoms, e.g. 2 to 6 carbon atoms) and having from 1 to 6 carbon-carbon triple bonds e.g. 1, 2, or 3 carbon-carbon triple bonds. Typical alkynyl groups include ethynyl (—C≡CH), propargyl (or propynyl, —C≡CCH₃), and the like. In the event that alkynyl is attached to nitrogen, the triple bond cannot be alpha to the nitrogen.

The term "substituted alkynyl" refers to an alkynyl group as defined above having 1, 2, 3, 4 or 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclyloxy, hydroxyamino, alkoxyamino, nitro, —SO-alkyl, —SO-aryl, —SO-heteroaryl, —SO₂-alkyl, SO₂-aryl and —SO₂-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF₃, amino, substituted amino, cyano, and —S(O)$_n$R, where R is alkyl, aryl, or heteroaryl and n is 0, 1 or 2.

The term "aminocarbonyl" refers to the group —C(O)NRR where each R is independently hydrogen, alkyl, cycloalkyl, aryl, heteroaryl, heterocyclyl or where both R groups are joined to form a heterocyclic group (e.g., morpholino). Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF₃, amino, substituted amino, cyano, and —S(O)$_n$R, where R is alkyl, aryl, or heteroaryl and n is 0, 1 or 2.

The term "ester" or "carboxyester" refers to the group —C(O)OR, where R is alkyl, cycloalkyl, aryl, heteroaryl, or heterocyclyl, which may be optionally further substituted by alkyl, alkoxy, halogen, CF₃, amino, substituted amino, cyano, or —S(O)$_n$R$^a$, in which R$^a$ is alkyl, aryl, or heteroaryl and n is 0, 1 or 2.

The term "acylamino" refers to the group —NRC(O)R where each R is independently hydrogen, alkyl, aryl, heteroaryl, or heterocyclyl. All substituents may be optionally further substituted by alkyl, alkoxy, halogen, CF₃, amino, substituted amino, cyano, or —S(O)$_n$R, in which R is alkyl, aryl, or heteroaryl and n is 0, 1 or 2.

The term "acyloxy" refers to the groups —OC(O)-alkyl, —OC(O)-cycloalkyl, —OC(O)-aryl, —OC(O)-heteroaryl, and —OC(O)-heterocyclyl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF₃, amino, substituted amino, cyano, and —S(O)$_n$R, where R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl, fluorenyl, and anthryl). Typical aryls include phenyl, fluorenyl, naphthyl, anthryl, and the like.

Unless otherwise constrained by the definition for the aryl substituent, such aryl groups can optionally be substituted with 1, 2, 3, 4 or 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclyloxy, hydroxyamino, alkoxyamino, nitro, —SO-alkyl, —SO-aryl, —SO-heteroaryl, —SO₂-alkyl, SO₂-aryl and —SO₂-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF₃, amino, substituted amino, cyano, and —S(O)$_n$R, where R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —NH₂.

The term "substituted amino" refers to the group —NRR where each R is independently selected from the group consisting of hydrogen, alkyl, cycloalkyl, aryl, heteroaryl and heterocyclyl provided that both R groups are not hydrogen, or a group —Y—Z, in which Y is optionally substituted alkylene and Z is alkenyl, cycloalkenyl, or alkynyl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF₃, amino, substituted amino, cyano, and —S(O)—R, where R is alkyl, aryl, or heteroaryl and n is 0, 1 or 2.

The term "carboxyalkyl" refers to the groups —C(O)O-alkyl, —C(O)O-cycloalkyl, where alkyl and cycloalkyl are as defined herein, and may be optionally further substituted by alkyl, alkenyl, alkynyl, alkoxy, halogen, CF₃, amino, substituted amino, cyano, or —S(O)$_n$R, in which R is alkyl, aryl, or heteroaryl and n is 0, 1 or 2.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and bicyclo[2.2.1]heptane, or cyclic alkyl groups to which is fused an aryl group, for example indan, and the like.

The term "cycloalkenyl" refers to cyclic alkyl groups of from 3 to 20 carbon atoms having a single cyclic ring or multiple condensed rings and having at least one double bond and preferably from 1 to 2 double bonds.

The terms "substituted cycloalkyl" and "substituted cycloalkenyl" refer to cycloalkyl or cycloalkenyl groups having 1, 2, 3, 4 or 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, amino sulfonyl, aminocarbonylamino, heteroaryloxy, heterocyclyl, heterocyclyloxy, hydroxyamino, alkoxyamino, nitro, —SO-alkyl, —SO-aryl, —SO-heteroaryl, —SO₂-alkyl, SO₂-aryl and —SO₂-heteroaryl. The term "substituted cycloalkyl" also includes cycloalkyl groups wherein one or more of the annular carbon atoms of the cycloalkyl group is a carbonyl group (i.e. an oxygen atom is oxo to the ring). Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF₃, amino, substituted amino, cyano, and —S(O)$_n$R, where R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "alkoxycarbonylamino" refers to a group —NHC(O)OR in which R is optionally substituted alkyl.

The term "alkyl amine" refers to R—NH$_2$ in which R is optionally substituted alkyl.

The term "dialkyl amine" refers to R—NHR in which each R is independently an optionally substituted alkyl.

The term "trialkyl amine" refers to NR$_3$ in which R each R is independently an optionally substituted alkyl.

The term "azido" refers to a group

The term "hydroxyl" or "hydroxyl" refers to a group —OH.

The term "arylthio" refers to the group —S-aryl.

The term "heterocyclylthio" refers to the group —S-heterocyclyl.

The term "alkylthio" refers to the group —S-alkyl.

The term "aminosulfonyl" refers to the group —SO$_2$NRR, wherein each R is independently selected from the group consisting of hydrogen, alkyl, cycloalkyl, aryl, heteroaryl and heterocyclyl. Unless otherwise constrained by the definition, all substituents may optionally be further substituted by 1, 2, or 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclyloxy, hydroxyamino, alkoxyamino, nitro, —SO-alkyl, —SO-aryl, —SO-heteroaryl, —SO$_2$-alkyl, SO$_2$-aryl and —SO$_2$-heteroaryl.

The term "aminocarbonylamino" refers to the group —NR$^c$C(O)NRR, wherein R$^c$ is hydrogen or alkyl and each R is independently selected from the group consisting of hydrogen, alkyl, cycloalkyl, aryl, heteroaryl and heterocyclyl. Unless otherwise constrained by the definition, all substituents may optionally be further substituted by 1, 2, or 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl.

The term "heterocyclooxy" refers to the group —O-heterocyclyl.

The term "alkoxyamino" refers to the group —NHOR in which R is optionally substituted alkyl.

The term "hydroxyamino" refers to the group —NHOH.

The term "heteroaryl" refers to a group comprising single or multiple rings comprising 1 to 15 carbon atoms and 1 to 4 heteroatoms selected from oxygen, nitrogen, and sulfur within at least one ring. The term "heteroaryl" is generic to the terms "aromatic heteroaryl" and "partially saturated heteroaryl". The term "aromatic heteroaryl" refers to a heteroaryl in which at least one ring is aromatic. Examples of aromatic heteroaryls include pyrrole, thiophene, pyridine, quinoline, pteridine. The term "partially saturated heteroaryl" refers to a heteroaryl having a structure equivalent to an underlying aromatic heteroaryl which has had one or more double bonds in an aromatic ring of the underlying aromatic heteroaryl saturated. Examples of partially saturated heteroaryls include dihydropyrrole, dihydropyridine, chroman, and the like.

Unless otherwise constrained by the definition for the heteroaryl substituent, such heteroaryl groups can be optionally substituted with 1 to 5 substituents (typically 1, 2, or 3 substituents) selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl (an alkyl ester), arylthio, heteroaryl, heteroarylthio, heterocyclylthio, thiol, alkylthio, aryl, aryloxy, aralkyl, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2. Such heteroaryl groups can have a single ring (e.g., pyridyl or furyl) or multiple condensed rings (e.g., indolizinyl, benzothiazole, or benzothienyl). Examples of nitrogen heterocyclyls and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroaryloxy" refers to the group heteroaryl-O—.

The term "heterocyclyl," "heterocycle," or "heterocyclic" refers to a monoradical saturated group having a single ring or multiple condensed rings, having from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2. Preferred heterocyclics include tetrahydrofuranyl, morpholino, piperidinyl, and the like.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —S(O)$_2$R, in which R is alkyl, aryl, or heteroaryl. "Substituted sulfone" refers to a group —S(O)$_2$R, in which R is substituted alkyl, substituted aryl, or substituted heteroaryl, as defined herein.

The term "keto" or "oxo" refers to a group —C(O)—.

The term "thiocarbonyl" refers to a group —C(S)—.

The term "carboxy" refers to a group —C(O)—OH.

"Optional" or "optionally" means that the subsequently described event or circumstance may or may not occur, and that the description includes instances where said event or circumstance occurs and instances in which it does not.

A "substituted" group includes embodiments in which a monoradical substituent is bound to a single atom of the substituted group (e.g. forming a branch), and also includes embodiments in which the substituent may be a diradical bridging group bound to two adjacent atoms of the substituted group, thereby forming a fused ring on the substituted group.

Where a given group (moiety) is described herein as being attached to a second group and the site of attachment is not explicit, the given group may be attached at any available site of the given group to any available site of the second group. For example, a "lower alkyl-substituted phenyl", where the attachment sites are not explicit, may have any available site of the lower alkyl group attached to any available site of the phenyl group. In this regard, an "available site" is a site of the group at which a hydrogen of the group may be replaced with a substituent.

A compound of a given Formula (e.g. the "compound of Formula (I)") is intended to encompass the compounds of the disclosure, and the pharmaceutically acceptable salts, pharmaceutically acceptable esters, hydrates, polymorphs, and prodrugs of such compounds. Additionally, the compounds of the disclosure may possess one or more asymmetric centers, and can be produced as a racemic mixture or as individual enantiomers or diastereoisomers. The number of stereoisomers present in any given compound of a given Formula depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis, or by resolution of the compound by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

"Isomers" are different compounds that have the same molecular formula. Isomers include stereoisomers, enantiomers, and diastereomers.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Calm Ingold Prelog R S system. When the compound is a pure enantiomer the stereochemistry at each chiral carbon may be specified by either R or S. Resolved compounds whose absolute configuration is unknown are designated (+) or (−) depending on the direction (dextro- or laevorotary) that they rotate the plane of polarized light at the wavelength of the sodium D line.

Some of the compounds exist as tautomeric isomers. Tautomeric isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers. Non-limiting examples of amide-comprising and imidic acid-comprising tautomers are shown below:

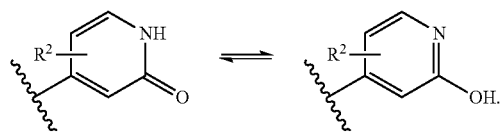

The term "therapeutically effective amount" refers to an amount that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "polymorph" refers to different crystal structures of a crystalline compound. The different polymorphs may result from differences in crystal packing (packing polymorphism) or differences in packing between different conformers of the same molecule (conformational polymorphism).

The term "solvate" refers to a complex formed by the combining of a compound of Formula (I) and a solvent.

The term "hydrate" refers to the complex formed by the combining of a compound of Formula (I) and water.

The term "prodrug" refers to a compound of Formula (I) that includes chemical groups which, in vivo, can be converted and/or can be split off from the remainder of the molecule to provide for the active drug, a pharmaceutically acceptable salt thereof, or a biologically active metabolite thereof.

Any formula or structure given herein, including Formula (I) compounds, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl, and $^{125}$I. Various isotopically labeled compounds of the present invention, for example those into which radioactive isotopes such as $^3$H, $^{13}$C, and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients.

Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An $^{18}$F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the Formula (I).

The concentration of such a heavier isotope, specifically deuterium, may be defined by an isotopic enrichment factor. In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this invention any atom specifically designated as a deuterium (D) is meant to represent deuterium.

The term "treatment" or "treating" means any administration of a compound of the invention to a mammal having a disease or susceptible to a disease for purposes including:
  (i) preventing the disease, that is, causing the clinical symptoms of the disease not to develop;
  (ii) inhibiting the disease, that is, arresting the development of clinical symptoms; and/or
  (iii) relieving the disease, i.e. causing the regression of clinical symptoms.

In many cases, the compounds of this disclosure are capable of forming acid and/or base salts by virtue of the presence of amino and/or carboxyl groups or groups similar thereto.

The term "dopamine producing agents" as used herein includes nicotine, alcohol, amphetamnines, other drugs of addiction and foods, especially sugary foods. Thus diseases related to dopamine producing agents include addiction to alcohol, cocaine, marijuana, nicotine, food and sequela thereof e.g. obesity.

The term "pharmaceutically acceptable salt" of a given compound refers to salts that retain the biological effectiveness and properties of the given compound, and which are not biologically or otherwise undesirable. Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Where a given group (moiety) is described herein as being attached to a second group and the site of attachment is not explicit, the given group may be attached at any available site of the given group to any available site of the second group. For example, a "lower alkyl-substituted phenyl", where the attachment sites are not explicit, may have any available site of the lower alkyl group attached to any available site of the phenyl group. In this regard, an "available site" is a site of the group at which a hydrogen of the group may be replaced with a substituent.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. Also not included are infinite numbers of substituents, whether the substituents are the same or different. In such cases, the maximum number of such substituents is three. Each of the above definitions is thus constrained by a limitation that, for example, substituted aryl groups are limited to -substituted aryl-(substituted aryl)-substituted aryl.

Compounds of Formula (I)

Nomenclature:

The naming and numbering of the compounds is illustrated with a representative compound (2):

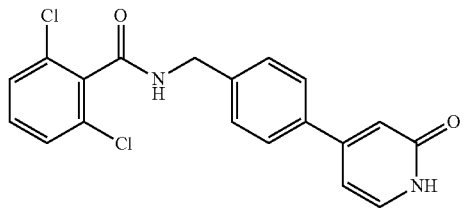

(2)

namely: 2,6-dichloro-N-[4-(2-oxo-1,2-dihydro-pyridin-4-yl)-benzyl]-benzamide.

Accordingly, in certain aspects, is provided compounds of Formula (I):

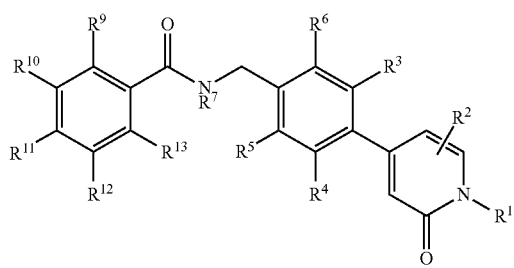

Formula (Ia)

wherein:
$R^1$ is hydrogen, —$CH_2OH$, —$CH_2OP(O)(OR^{20})(OR^{21})$, or optionally substituted $C_{1-6}$ alkyl;
$R^2$ is hydrogen, —CN, halo, optionally substituted lower $C_{1-6}$ alkyl, or cycloalkyl;
each of $R^3$, $R^4$, $R^5$, $R^6$, $R^9$, $R^{10}$, $R^{11}$, $R^{12}$ and $R^{13}$ is independently hydrogen, hydroxyl, aminocarbonyl, acyl, acylamino, —O—($C_1$ to $C_6$-alkyl)-O—($C_1$ to $C_6$-alkyl), cyano, halo, —$SO_2NR^{24}R^{25}$, —$NR^{24}R^{25}$, optionally substituted alkyl, optionally substituted alkylene, optionally substituted alkynyl, optionally substituted alkoxy, optionally substituted cycloalkyl, optionally substituted aryl, optionally substituted aralkyl, optionally substituted heteroaryl, optionally substituted heteroaralkyl, or optionally substituted heterocyclyl;
wherein said optionally substituted alkyl, alkylene, alkynyl, alkoxy, cycloalkyl, aryl, aralkyl, heteroaryl, heteroaralkyl, or heterocyclyl are optionally substituted with one, two or three substituents independently selected from the group consisting of halo, —$NO_2$, phenyl, heterocyclyl, heteroaryl, $C_{1-6}$ alkyl, cycloalkyl, —$N(R^{24})(R^{25})$, —C(O)—$R^{24}$, —C(O)—$OR^{24}$, —C(O)—$N(R^{24})(R^{25})$, —CN and —O—$R^{24}$;
$R^7$ is hydrogen or optionally substituted $C_{1-6}$ alkyl;
each of $R^{20}$ and $R^{21}$ is independently $Na^+$, $Li^+$, $K^+$, hydrogen, or $C_{1-6}$ alkyl; or $R^{20}$ and $R^{21}$ can be combined to represent a single divalent cation $Zn^{2+}$, $Ca^{2+}$, or $Mg^{2+}$;
each of $R^{22}$ and $R^{23}$ is independently optionally substituted alkyl, optionally substituted alkoxy, optionally substituted cycloalkyl, optionally substituted aryl, or —$NR^{24}R^{25}$; and
each of $R^{24}$ and $R^{25}$ is independently hydrogen or $C_{1-6}$ alkyl or when combined together with the nitrogen to which they are attached form a heterocycle; or
a pharmaceutically acceptable salt, ester, or tautomer thereof.

In certain embodiments, $R^1$ is hydrogen. In certain embodiments, $R^1$ is $C_{1-6}$ alkyl. In certain embodiments, $R^1$ is methyl. In certain embodiments, $R^1$ is —$CH_2OP(O)(OR^{20})(OR^{21})$; and each of $R^{20}$ and $R^{21}$ is independently $Na^+$, $Li^+$, $K^+$, or hydrogen. In certain embodiments, at least one of $R^1$, $R^9$, $R^{10}$, $R^{11}$, $R^{12}$, $R^{13}$ is not hydrogen. In other embodiments, at least two of $R^1$, $R^9$, $R^{10}$, $R^{11}$, $R^{12}$, $R^{13}$ is not hydrogen.

In certain embodiments, $R^2$ is hydrogen. In certain embodiments, $R^2$ is $C_{1-6}$ alkyl. In certain embodiments, $R^2$ is methyl. In certain embodiments, $R^2$ is selected from the group consisting of ethyl, n-propyl, iso-propyl, n-butyl, iso-butyl, t-butyl, and n-hexyl. In certain embodiments, $R^2$ is halo. In certain embodiments, $R^2$ is fluoro. In certain embodiments, $R^2$ is chloro. In certain embodiments, $R^2$ is bromo. In certain embodiments, $R^2$ is iodo.

In certain embodiments, each of $R^3$, $R^4$, $R^5$, $R^6$ $R^9$, $R^{10}$, $R^{11}$, $R^{12}$ and $R^{13}$ is independently hydrogen, hydroxyl, —OP(O)($OR^{20}$)($OR^{21}$), —$CH_2OH$, —$CH_2OP(O)(OR^{20})(OR^{21})$, optionally substituted $C_{1-6}$ alkyl, optionally substituted $C_{3-8}$ cycloalkyl, optionally substituted $C_{1-6}$ alkoxy, —O—($C_1$ to $C_6$-alkyl)-O—($C_1$ to $C_6$-alkyl), —$C(O)NH_2$, cyano, or halo. In certain embodiments, each of $R^3$, $R^4$, $R^5$, and $R^6$ is independently hydrogen, $C_{1-6}$ alkyl, or halo. In certain embodiments, one of $R^3$, $R^4$, $R^5$, or $R^6$ is $C_{1-6}$ alkyl or halo. In certain embodiments, one of $R^3$, $R^4$, $R^5$, or $R^6$ is selected from the group consisting of ethyl, n-propyl, iso-propyl, n-butyl, iso-butyl, t-butyl, and n-hexyl. In certain embodiments, one of $R^3$, $R^4$, $R^5$, or $R^6$ is methyl. In certain embodiments, one of $R^3$, $R^4$, $R^5$, or $R^6$ is fluoro. In certain embodiments, one of $R^3$, $R^4$, $R^5$, or $R^6$ is chloro. In certain embodiments, one of $R^3$, $R^4$, $R^5$, or $R^6$ is fluoro. In certain embodiments, one of $R^3$, $R^4$, $R^5$, or $R^6$ is iodo.

In certain embodiments, $R^7$ is hydrogen. In certain embodiments, $R^7$ is $C_{1-6}$ alkyl. In certain embodiments, $R^7$ is selected from the group consisting of ethyl, n-propyl, iso-propyl, n-butyl, iso-butyl, t-butyl, and n-hexyl. In certain embodiments, $R^7$ is methyl.

In certain embodiments, at least one of $R^9$ and $R^{13}$ is not hydrogen. In certain embodiments, at least one of $R^9$ and $R^{13}$ is halo or $C_{1-6}$ alkyl. In certain embodiments, at least one of $R^9$ and $R^{13}$ is selected from the group consisting of ethyl, n-propyl, iso-propyl, n-butyl, iso-butyl, t-butyl, and n-hexyl. In certain embodiments, at least one of $R^9$ and $R^{13}$ is independently chloro, fluoro, or methyl. In certain embodiments, at least one of $R^9$ and $R^{13}$ is bromo. In certain embodiments, at least one of $R^9$ and $R^{13}$ is iodo. In certain embodiments, $R^9$ and $R^{13}$ are independently halo or $C_{1-6}$ alkyl. In certain embodiments, $R^9$ and $R^{13}$ are independently chloro, fluoro, or methyl. In certain embodiments, $R^9$ and $R^{13}$ are chloro. In certain embodiments, $R^9$ and $R^{13}$ are methyl.

In certain embodiments, each of $R^{10}$ and $R^{12}$ is independently hydrogen, halo, or $C_{1-6}$ alkyl. In certain embodiments, each of $R^{10}$ and $R^{12}$ is independently ethyl, n-propyl, iso-propyl, n-butyl, iso-butyl, t-butyl, and n-hexyl. In certain embodiments, each of $R^{10}$ and $R^{12}$ is independently hydrogen, chloro, fluoro, or methyl. In certain embodiments, each of $R^{10}$ and $R^{12}$ is independently bromo. In certain embodiments, each of $R^{10}$ and $R^{12}$ is independently iodo. In certain embodiments, each of $R^{10}$ and $R^{12}$ is independently fluoro. In certain embodiments, each of $R^{10}$ and $R^{12}$ is independently chloro. In certain embodiments, $R^{10}$ and $R^{12}$ are hydrogen.

In certain embodiments, $R^{11}$ is hydrogen. In certain embodiments, $R^{11}$ is —O—($C_1$ to $C_6$-alkyl)-O—($C_1$ to $C_6$-alkyl). In certain embodiments, $R^{11}$ is —OCH$_2$CH$_2$OCH$_3$. In certain embodiments, $R^{11}$ is independently ethyl, n-propyl, iso-propyl, n-butyl, iso-butyl, t-butyl, and n-hexyl. In certain embodiments, $R^{11}$ is halo. In certain embodiments, $R^{11}$ is fluoro. In certain embodiments, $R^{11}$ is chloro. In certain embodiments, $R^{11}$ is bromo. In certain embodiments, $R^{11}$ is iodo.

In certain embodiments,

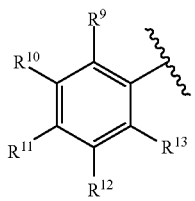

is selected from the group consisting of:

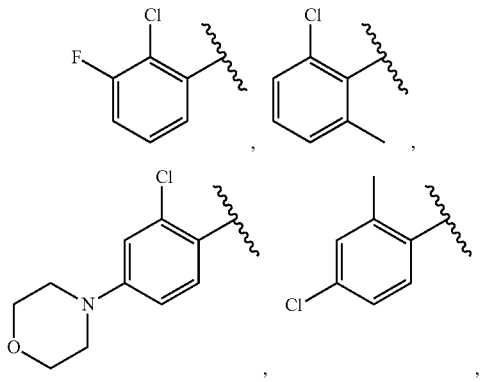

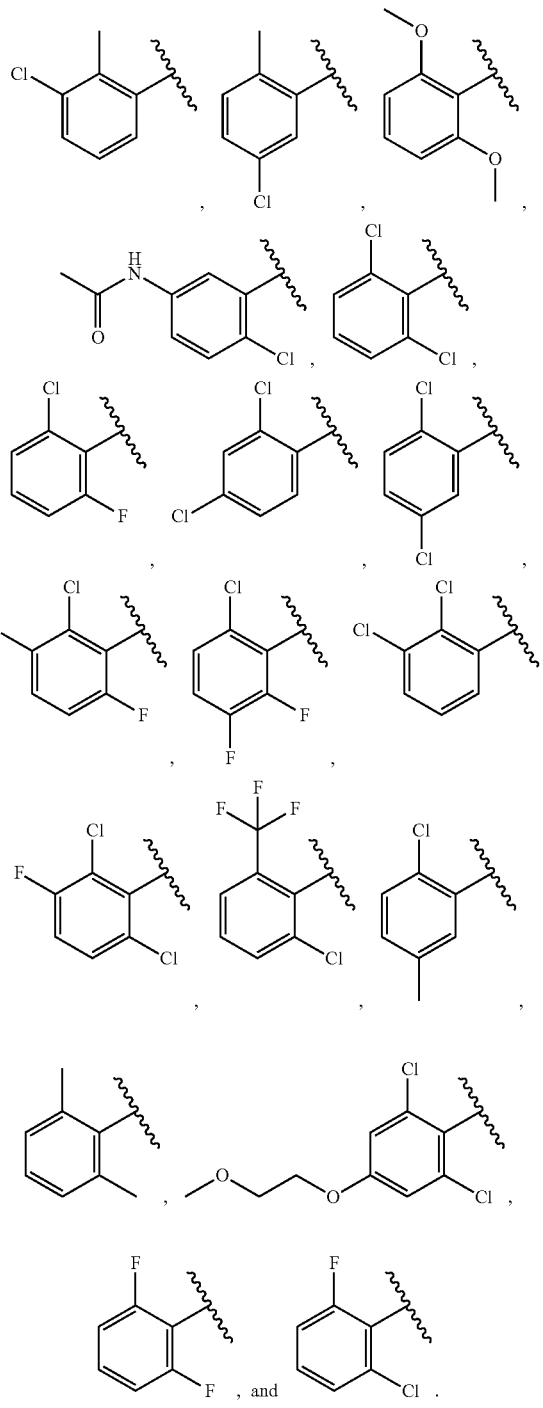

In certain embodiments, $R^1$ is hydrogen, methyl, or —CH$_2$OP(O)(OR$^{20}$)(OR$^{21}$); $R^2$ is hydrogen, methyl, or fluoro; each of $R^3$ and $R^4$ is independently hydrogen or methyl; each of $R^5$ and $R^6$ is independently hydrogen or fluoro; $R^7$ is hydrogen; $R^9$ is hydrogen, chloro, fluoro, or methyl; $R^{10}$ is hydrogen or fluoro; $R^{11}$ is hydrogen or —OCH$_2$CH$_2$OCH$_3$; $R^{12}$ is hydrogen or fluoro; $R^{13}$ is hydrogen, chloro, fluoro, or methyl; and each of $R^{20}$ and $R^{21}$ is independently Na$^+$, Li$^+$, K$^+$, or hydrogen.

In certain embodiments, the structure is:

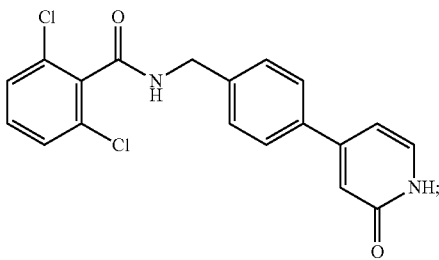 [SMILES: O=C(NCc1ccc(-c2cc[nH]c(=O)c2)cc1)c1c(Cl)cccc1Cl]

or a pharmaceutically acceptable salt, ester, single stereoisomer, mixture of stereoisomers, or tautomer thereof.

In certain embodiments, the structure is:

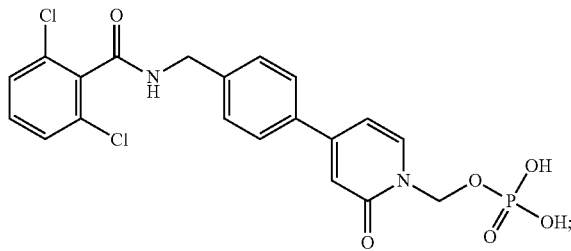 [SMILES: O=C(NCc1ccc(-c2ccn(COP(=O)(O)O)c(=O)c2)cc1)c1c(Cl)cccc1Cl]

or a pharmaceutically acceptable salt, ester, single stereoisomer, mixture of stereoisomers, or tautomer thereof. The above compound is an example of a prodrug as it generates the free amide (pyridine) compound as a metabolite. One of ordinary skill in the art is able to synthesize other prodrugs of compounds of the invention based on disclosure herein and in the art.

In certain embodiments, the compound is selected from the group consisting of:
2,6-dichloro-4-(2-methoxyethoxy)-N-(4-(2-oxo-1,2-dihydropyridin-4-yl)benzyl)benzamide (1);
2,6-dichloro-N-[4-(2-oxo-1,2-dihydro-pyridin-4-yl)-benzyl]-benzamide (2);
2-chloro-3-fluoro-N-(4-(2-oxo-1,2-dihydropyridin-4-yl)benzyl)benzamide (3);
2-chloro-6-methyl-N-(4-(2-oxo-1,2-dihydropyridin-4-yl)benzyl)benzamide (4);
2,6-dimethyl-N-(4-(2-oxo-1,2-dihydropyridin-4-yl)benzyl)benzamide (5);
2,6-dichloro-N-[4-(6-methyl-2-oxo-1,2-dihydro-pyridin-4-yl)-benzyl]-benzamide (6);
2-chloro-3,6-difluoro-N-(4-(2-oxo-1,2-dihydropyridin-4-yl)benzyl)benzamide (7);
2,6-dichloro-N-(3-methyl-4-(2-oxo-1,2-dihydropyridin-4-yl)benzyl)benzamide (8);
2,6-dichloro-N-(4-(1-methyl-2-oxo-1,2-dihydropyridin-4-yl)benzyl)benzamide (9);
2,6-difluoro-N-(4-(2-oxo-1,2-dihydropyridin-4-yl)benzyl)benzamide (10);
2-chloro-6-fluoro-N-(4-(2-oxo-1,2-dihydropyridin-4-yl)benzyl)benzamide (11);
2,6-dichloro-N-(2-fluoro-4-(2-oxo-1,2-dihydropyridin-4-yl)benzyl)benzamide (12);
2,6-dichloro-N-(4-(5-fluoro-2-oxo-1,2-dihydropyridin-4-yl)benzyl)benzamide (13); and
phosphoric acid mono-(4-{4-[(2,6-dichloro-benzoylamino)-methyl]-phenyl}-2-oxo-2H-pyridin-1-ylmethyl) ester (14); or a pharmaceutically acceptable salt, ester, single stereoisomer, mixture of stereoisomers, or tautomer thereof.

Synthesis of the Compounds of Formula (I)

Compound Preparation:

The compounds can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures Additionally, as will be apparent to those skilled in the art, conventional protecting groups may be necessary to prevent certain functional groups from undergoing undesired reactions. The term "protecting group" or "PG," as used herein, is meant that a particular functional moiety, e.g., O, S, or N, is temporarily blocked so that a reaction can be carried out selectively at another reactive site in a multifunctional compound. "Protecting groups" or "PGs," as used herein, are well known in the art and include those described in detail in *Protective Groups in Organic Synthesis*, Fourth Ed., Greene, T. W. and Wuts, P. G., Eds., John Wiley & Sons, New York: 2007, the entire contents of which are hereby incorporated by reference, and references cited therein.

The term "protecting group" or "PG" encompasses a "suitable amino protecting group" that is well known in the art and includes those described in detail in Greene et al. Non-limiting examples of suitable amino protecting groups include methyl carbamate, ethyl carbamate, 9-fluorenylmethyl carbamate (Fmoc), t-butyl carbamate (BOC), and benzyl carbamate (Cbz).

The term "protecting group" or "PG" further encompasses a "suitable carboxylic acid protecting group" and a "suitable phosphoric acid protecting group" that is well known in the art and includes those described in detail in Greene et al. Non-limiting examples of suitable carboxylic acid protecting groups and suitable phosphoric acid protecting groups further include, but are not limited to, silyl-, alkyl-, alkenyl-, aryl-, and arylalkyl-protecting groups.

The term "protecting group" or "PG" further encompasses a "suitable hydroxyl protecting group," that is well known in the art and includes those described in detail in Greene et al. Non-limiting examples of suitable hydroxyl protecting groups include methyl, t-butyl, methoxylmethyl (MOM), trimethylsilyl (TMS), triethylsilyl (TES), triisopropylsilyl (TIPS), and the like.

The term "leaving group" or "LG" as used herein, is well known among those of skill in the art as a labile substituent of a compound that is readily displaced from the compound. Leaving groups, as used herein, are described in *March's Advanced Organic Chemistry*, (John Wiley, and Sons, 5$^{th}$ Edition, 2001), and encompass the group consisting of a halo; $OR^G$; $SR^G$; $O(CO)R^G$; $S(CO)R^G$; $O(SO_2)R^G$; $OP(O)OR^GOR^H$; or $N_2^+$; wherein each $R^G$ and $R^H$ is, independently, hydrogen, a substituted or unsubstituted, branched or unbranched, cyclic or acyclic $C_{1-10}$ alkyl; a substituted or unsubstituted, branched or unbranched, cyclic or acyclic $C_{1-10}$ haloalkyl; a substituted or unsubstituted aryl; or a substituted or unsubstituted haloaryl. In certain embodiments, each LG is, independently, a chloro; bromo; iodo;

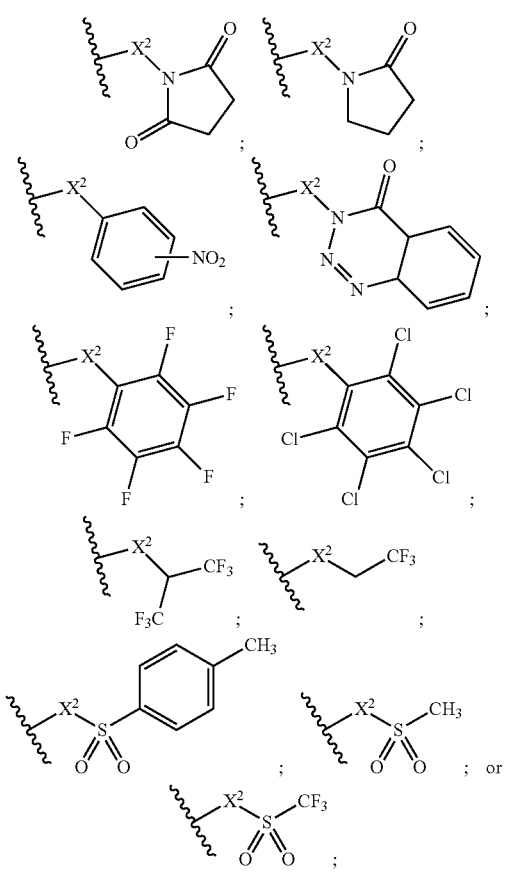

wherein each $X^2$ is, independently, O or S.

The term "peptide coupling agent" refers to reagents used in the methods of peptide coupling that are well known to those skilled in the art as described in M. Bodansky, et al., "The Practice of Peptide Synthesis, Reactivity and Structure, Concepts in Organic Chemistry," Volume 21, Second, Revised Edition, Springer-Verlag, New York, N.Y. (1994), the entire contents of which are hereby incorporated by reference. The "peptide coupling agents," as used herein, that are useful in the method include, but are not limited to those disclosed in Bodansky, et al., such as O-(7-azabenzotriazol-1-yl)-N,N,N',N'-tetramethyluronium hexafluorophosphate (HATU), O-benzotriazole-N,N,N',N'-tetramethyl-uronium-hexafluoro-phosphate (HBTU), dicyclohexyl carbodiimide (DCC), diisopropyl carbodiimide (DIC). DCC/1-hydroxy benzotriazole, DCC/N-hydroxysuccinimide, 1-ethyl-3-(3-dimethyllaminopropyl) carbodiimide hydrochloride EDC-HCl, 1-isobutoxycarbonyl-2-isobutoxy-1,2-dihydro quinone (IIDQ), carbonyldiimidizole, N-ethyl-5-phenylisoxazolium-3'-sulfonate (Woodward's Reagent K), benzotriazolyl-N-hydroxytris(dimethyamino)phosphonium hexafluorophosphate (BOP), (benzotriazol-1-yloxy) tripyrrolidinophosphonium hexafluorophosphate (PyBOP), and the like.

The term "Suzuki reaction" as used herein, is well known among those of skill in the art as and refers to a CC coupling of two reactants in which one reactant is a boronic acid or boronic ester moiety, as described by N. Miyaura and A. Suzuki; Chem. Rev.; 1995, 95, 2457-2483; and A. Suzuki, J. Organomet. Chem., 1999, 576, 147-168. Typically, the Suzuki reaction may be carried out in the presence of a palladium catalyst such as palladium(II) acetate, tetrakis (triphenylphosphine)palladium (0), palladium on activated charcoal or dichloro[1,1'-bis(diphenylphosphino)ferrocene] palladium(II), in an aprotic polar solvent (for example acetonitrile, N,N-dimethylformamide, dimethoxyethone or tetrahydrofuran) or a protic polar solvent (for example n-propanol, iso-propanol) or a mixture of these solvents with water. The volume of solvent used will be from approximately 3 to 30 times the quantity of boronic acid or boronic ester used. Advantageously, the palladium catalyst may contain a ligand selected from: a triphenylphosphine, a tri-o-tolylphosphine, a tri-m-tolylphosphine or a tri-p-tolylphosphine. The catalysts particularly preferred are palladium(II) acetate and palladium on carbon which make it possible to obtain particularly fast reaction kinetics. Palladium(II) acetate may be advantageously used in combination with a 2-(dicyclo hexylphosphino)biphenyl type ligand (J. P. Wolfe et al., J. Am. Chem. Soc., 1999, 121, 9550-9561). The reaction is generally carried out in the presence of an inorganic base such as potassium carbonate, sodium carbonate, caesium carbonate, sodium hydroxide or potassium hydroxide or in the presence of a tertiary amine such as triethylamine or diisopropylethylamine. In certain embodiments the inorganic base can be potassium carbonate or potassium hydroxide. The Suzuki reaction is preferably carried out under an inert atmosphere, for example, under an argon or nitrogen atmosphere. The reaction mixture is advantageously heated at a temperature in the range from 60° C. to 110° C., for 2 minutes to 24 hours. Quenching with an acidic medium, for example, in the presence of HCl, is often carried out. One skilled in the art will be able to modify these conditions, in particular by applying the variants of the Suzuki reaction which are described in the literature.

The term "cyclic boronic ester moiety" refers to portions of boron-comprising reactants used in Suzuki reactions such as 4,4,5,5-tetramethyl-1,3,2-dioxa boronic ester, 4,4,5,5-tetramethyl-1,3,2-dioxaboronic ester, pinacolato dioxaboronic ester, catechol dioxaboronic ester, neopentyl glycolato dioxaboronic ester, hexylene glycolato dioxaboronic ester, [(+)-pinonediolato]dioxaboronic ester, [(−)-pinonediolato] dioxaboronic ester, diethyl-d-tartrate glycolato dioxaboronic ester, diethyl-1-tartrate glycolato dioxaboronic ester, diisopropyl-d-tartrate glycolato dioxaboronic ester, diisopropyl-1-tartrate-glycolato dioxaboronic ester, N,N,N',N'-tetramethyl-d-tartaramide-glycolato dioxaboronic ester, or N,N,N', N'-tetramethyl-1-tartaramide glycolato dioxaboronic ester.

Furthermore, the compounds may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethone), diethyl ether, methanol, pyridine and the like]. Unless specified to the contrary, the solvents used in the reactions are inert organic solvents.

The term "q.s." means adding a quantity sufficient to achieve a stated function, e.g., to bring a solution to the desired volume (i.e., 100%).

Synthetic Strategies

The compounds of Formula (I) in which substituents $R^1$ through $R^{27}$, $X^1$, $Y^1$, $Z^1$ and $Z^2$ are as defined herein. LG is a leaving group (e.g., halo, hydroxyl, alkoxy, $OSO_2CF_3$, $N_2^+$, etc.); PG is a protecting group (e.g., t-butyl, t-butyl carbamate (BOC), etc.); and $Z^2$ is $(OH)_2$, $(OMe)_2$, $F_3^-$, or $(OR^H)(OR^J)$, wherein $OR^H$ and $OR^J$ may combine with boron to form a cyclic arylboronic ester moiety or cyclic alkylboronic ester moiety as described herein (e.g., 4,4,5,5-tetramethyl-1,3,2-dioxaboronic ester, catechol dioxaboronic ester, etc.); wherein $R^{17}$ is an optionally substituted alkylene moiety of 1-6 carbon atoms.

In one embodiment, the compounds of Formula (I) may be prepared according to the synthetic sequence shown in Scheme I.

Scheme I

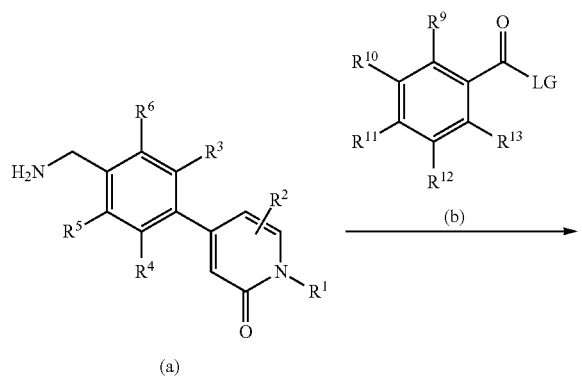

-continued

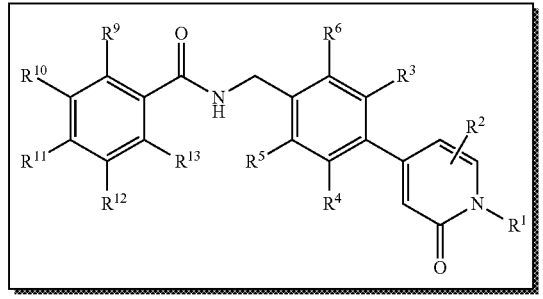

The compounds of Formula (I) can be prepared according to the synthetic sequence shown in Scheme I from reactants (a) and (b) that are commercially available or prepared by means well known in the art. In general, the reactants (a) and at least one molar equivalent, and preferably a slight excess (e.g., 1.2 to 1.5 molar equivalents) of (b), as shown in Scheme I, are combined under standard reaction conditions in an inert solvent, such as dimethylformamide (DMF), at a temperature of about 25° C. until the reaction is complete, generally about 16 hours. Standard reaction conditions may comprise the use of a molar excess of suitable base, such as sodium or potassium hydroxide, triethylamine, diisopropylethylamine, N-methylmorpholine (NMM), or pyridine, or in some cases where LG is hydroxyl, a peptide coupling reagent, such as O-(7-azabenzotriazol-1-yl)-N,N,N',N'-tetramethyluronium hexafluorophosphate (HATU), may be used. When the reaction is substantially complete, the product is subjected, if necessary, to a deprotection sequence under standard reaction conditions (e.g., THF, $CH_2Cl_2$, or the like, a molar excess of acid such as acetic acid, formic acid, trifluoroacetic acid, or the like as described herein) to yield isolated by conventional means.

Alternative methods for preparing compounds of Formula (I) are shown below in the synthetic sequences of Schemes II-V. For example, in a further embodiment, the compounds of Formula (I) may be prepared as shown in the synthetic sequence of Scheme II.

Scheme II

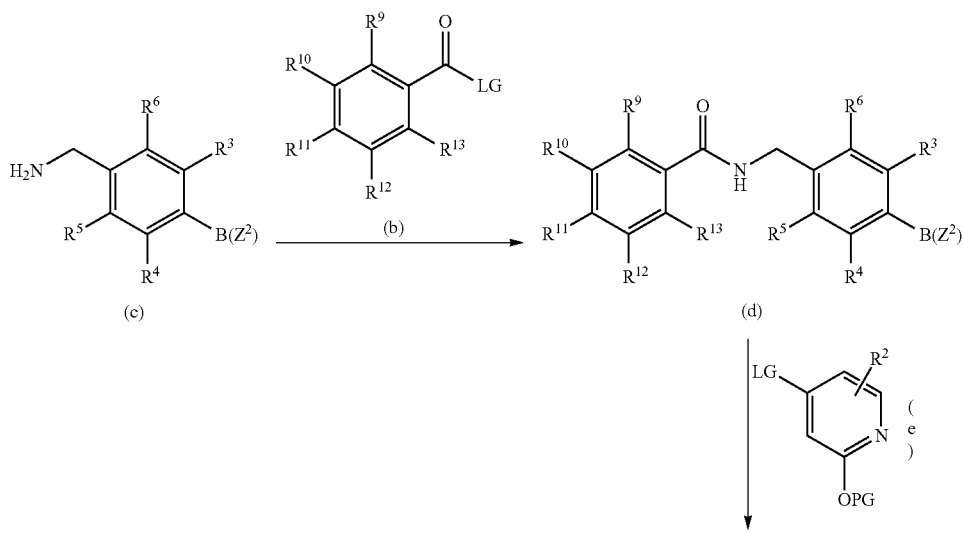

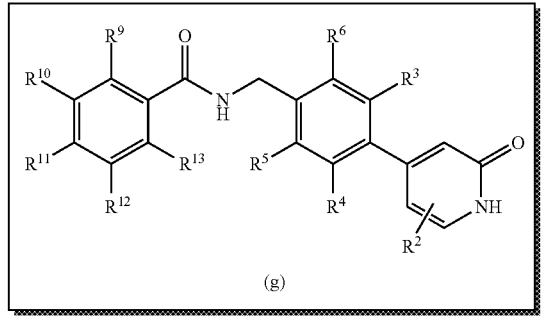

(g)

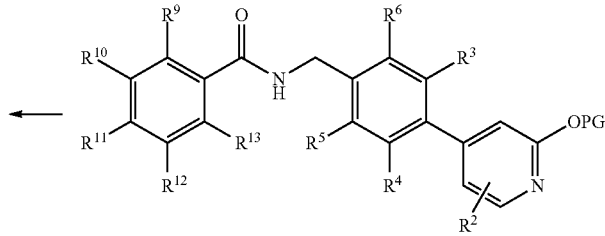

(f)

The compounds of Formula (I) can be prepared according to the synthetic sequence shown in Scheme II from the appropriate aminomethylarylboronic acid derivative (c) and at least one equivalent, and preferably a slight excess (e.g., 1.2 to 1.5 molar equivalents), of reactant (b) under standard reaction conditions. Standard reaction conditions may comprise the use of a suitable base, or in some cases where LG is hydroxyl, at least one equivalent, and preferably a slight molar excess (e.g., 1.2 to 1.5 molar equivalents), of a peptide coupling reagent as described herein. The resulting arylboronic acid derivative (d) and substituted pyridine (e) are then coupled under standard Suzuki reaction conditions (e.g., molar equivalents of (d) and (e) in dry DMF under argon atmosphere, at elevated temperatures, with approximately 5-10 molar % of palladium catalyst and a molar excess of inorganic base such as potassium carbonate, as described herein) followed, if necessary, by a deprotection sequence under standard reaction conditions (e.g., THF, $CH_2Cl_2$, or the like, a molar excess of acid such as acetic acid, formic acid, trifluoroacetic acid, or the like as described herein) to yield the pyridin-2(1H)-ones (g).

In another embodiment, the compounds of Formula (I) may be prepared as shown in the synthetic sequence of Scheme III.

Scheme III

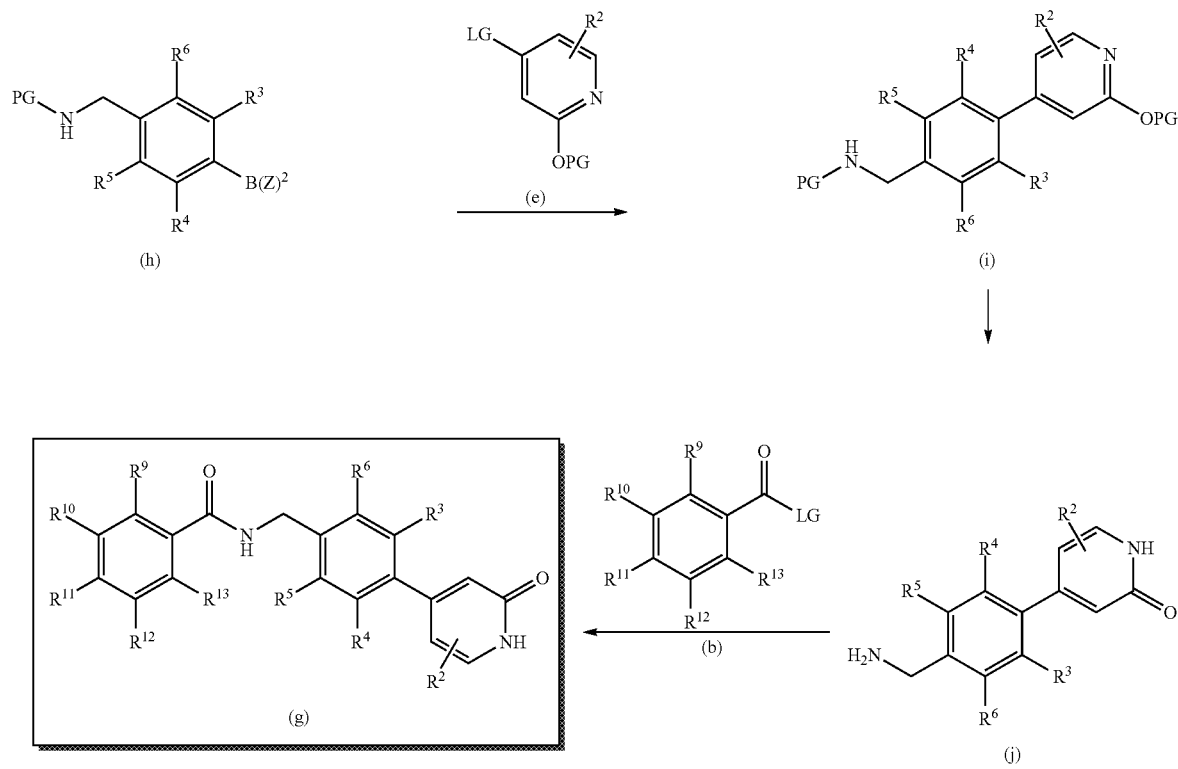

The compounds of Formula (I) can be prepared according to the synthetic sequence shown in Scheme III by the coupling of an arylboronic acid derivative, (h), and a substituted pyridine, (e), under standard Suzuki reaction conditions (e.g., molar equivalents of (h) and (e) in dry DMF, under argon atmosphere at elevated temperatures, with approximately 5-10 molar % of palladium catalyst and a molar excess of inorganic base such as potassium carbonate, as described herein) to yield the protected amine (i). Deprotection of (i) under standard conditions (e.g., THF, $CH_2Cl_2$, or the like, a molar excess of acid such as acetic acid, formic acid, trifluoroacetic acid, or the like as described herein) yields the primary amine (j), which is combined with at least one molar equivalent, and preferably a slight excess (e.g., 1.2 to 1.5 molar equivalents), of acyl derivative (b) under standard reaction conditions to yield the pyridin-2(1H)-ones (g). Standard reaction conditions may comprise the use of a suitable base, or in some cases where LG is hydroxyl, at least one equivalent, and preferably a slight molar excess (e.g., 1.2 to 1.5 molar equivalents), of a peptide coupling reagent as described herein.

In yet another embodiment, the compounds of Formula (I) may be prepared as shown in the synthetic sequence of Scheme IV.

The compounds of Formula (I) can be prepared according to the synthetic sequence shown in Scheme IV by reacting amine (k) with at least one equivalent, and preferably a slight excess (e.g., 1.2 to 1.5 molar equivalents), of acyl derivative (b) under standard reaction conditions to yield amide (l). Standard reaction conditions may comprise the use of a suitable base, or in some cases where LG is hydroxyl, at least one equivalent, and preferably a slight molar excess (e.g., 1.2 to 1.5 molar equivalents), of a peptide coupling reagent as described herein. Amide (l) is then coupled with pyridylboronic acid derivative (m) and under standard Suzuki conditions (e.g., molar equivalents of (l) and (m) in dry DMF under argon atmosphere at elevated temperatures, with approximately 5-10 molar % of palladium catalyst and a molar excess of inorganic base such as potassium carbonate, as described herein) to produce the substituted pyridine derivative (f) which is converted to the pyridin-2(1H)-ones (g) following deprotection (e.g., THF, $CH_2Cl_2$, or the like, a molar excess of acid such as acetic acid, formic acid, trifluoroacetic acid, or the like as described herein).

In certain embodiments, phosphate ester derivatives of Formula (I) may be prepared as shown below in the synthetic sequence of Scheme V.

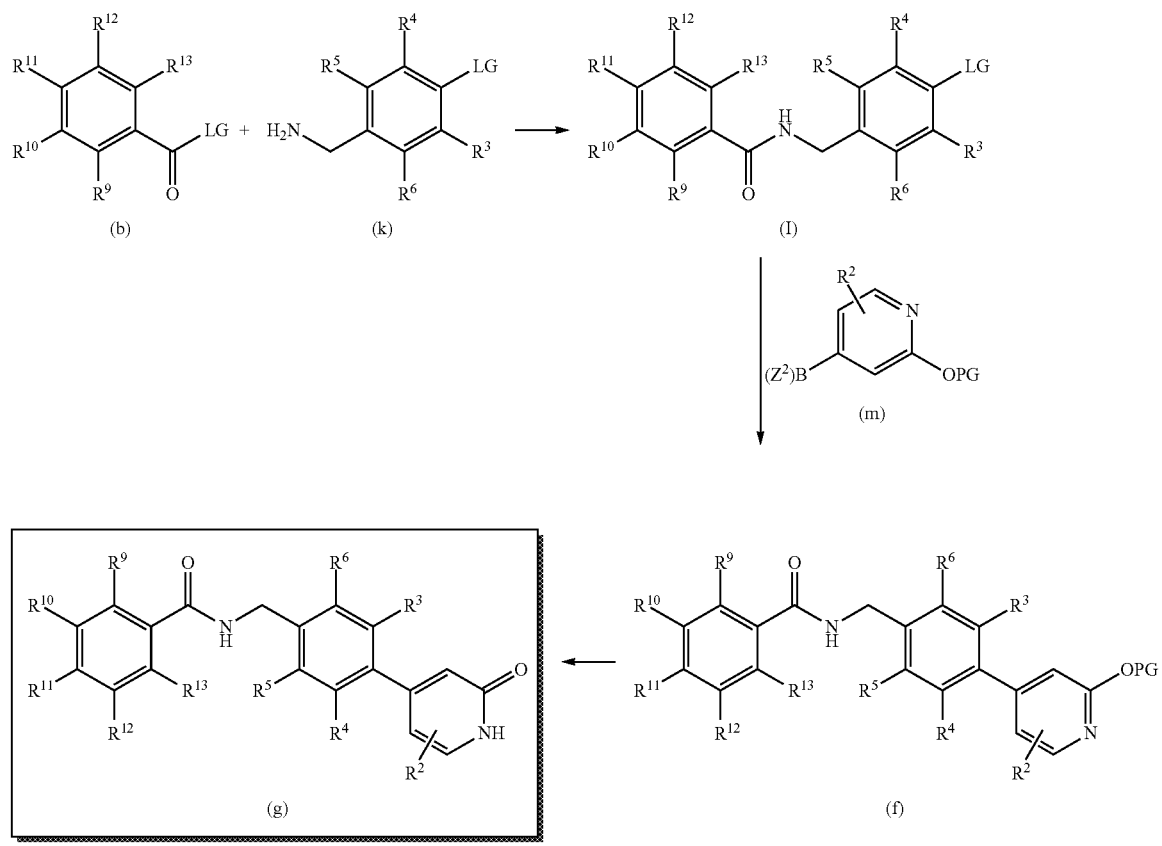

Scheme IV

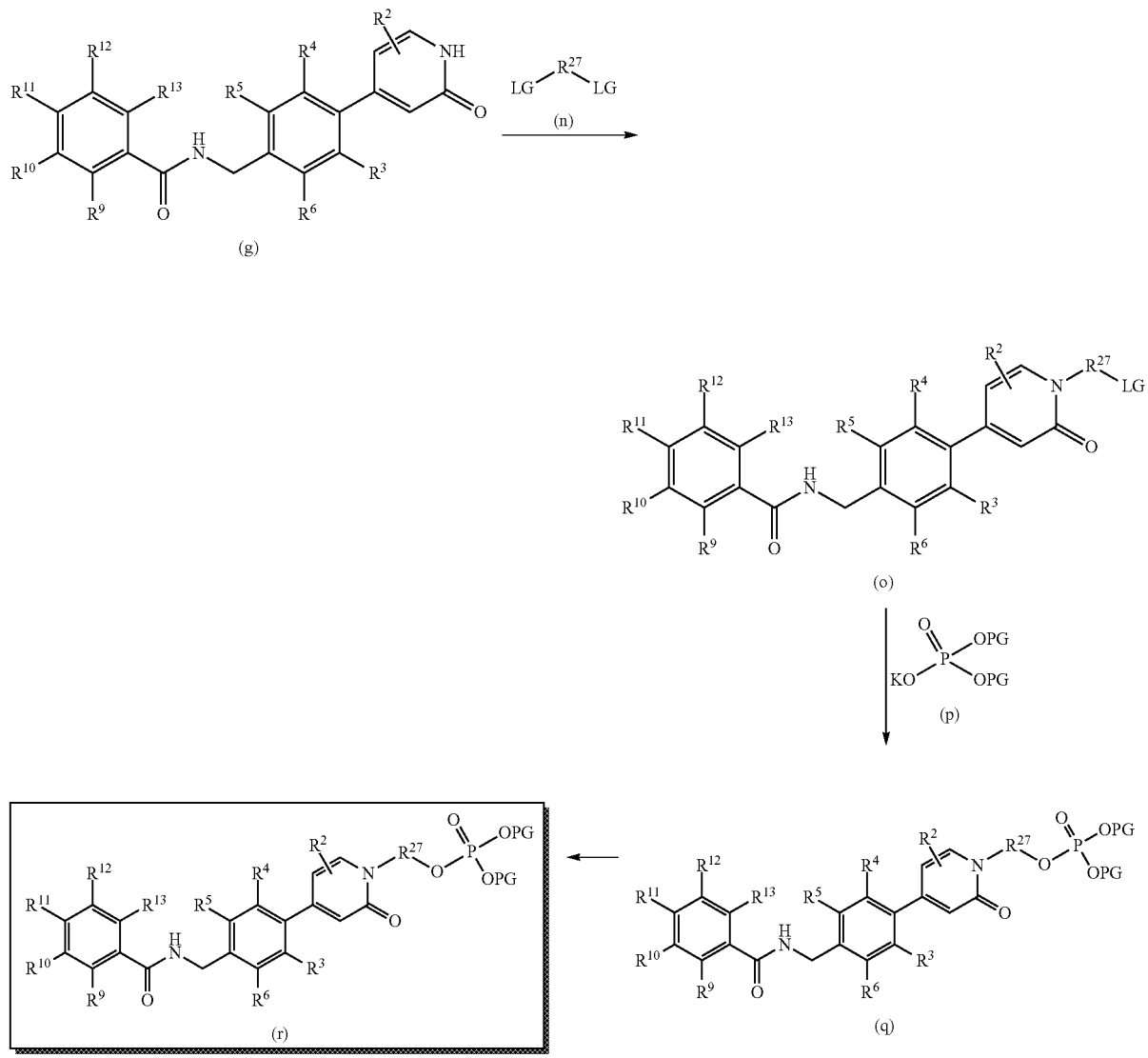

Scheme V

For example, phosphate ester derivatives (r) can be prepared according to the synthetic sequence of Scheme V by the alkylation of a pyridin-2(1H)-one (g) with at least one equivalent, and preferably a slight excess (e.g., 1.2 to 1.5 molar equivalents) of linker (n), wherein $R^{27}$ is an optionally substituted alkylene moiety of 1-6 carbon atoms, and at least one equivalent, and preferably a slight excess (e.g., 1.2 to 2 molar equivalents) of a suitable base such as triethylamine, diisopropylethylamine, N-methylmorpholine (NMM), or pyridine under standard reaction conditions to yield the alkylated pyridin-2(1H)-one (o) derivative which can subsequently be used to O-alkylate a molar excess (e.g., 1.2 to 5 molar equivalents) of phosphate diester (p) to yield a the corresponding phosphate triester (q). Deprotection of phosphate triester (q) under standard conditions (e.g., $CH_3CN/H_2O$ or the like, a molar excess of acid such as acetic acid or the like with heating, as described herein) yields phosphate ester (r).

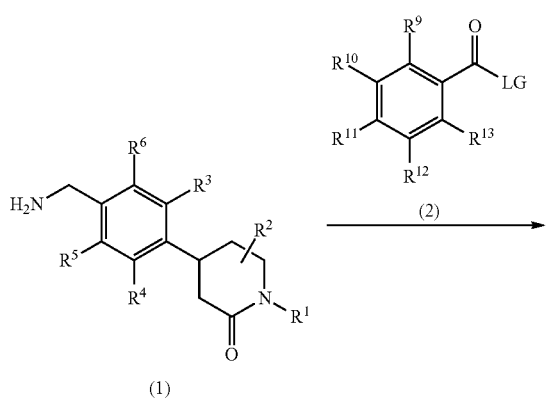

Scheme A

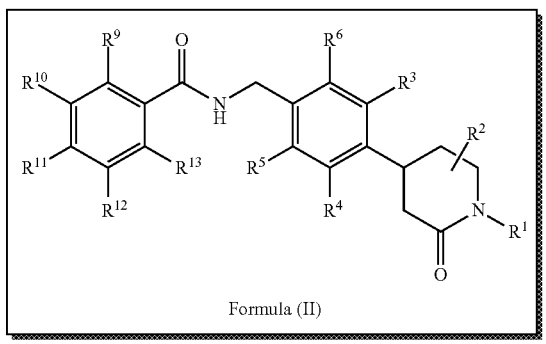

Formula (II)

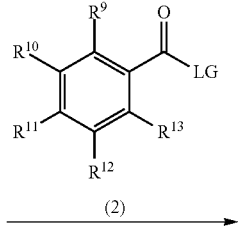

(3)

The compounds of Formula (II) can be prepared according to the synthetic sequence shown in Scheme A from reactants (1) and (2) that are commercially available or prepared by means well known in the art. In general, the reactants (1) and at least one molar equivalent, and preferably a slight excess (e.g., 1.2 to 1.5 molar equivalents) of (2), as shown in Scheme A, are combined under standard reaction conditions in an inert solvent, such as dimethylformamide (DMF), at a temperature of about 25° C. until the reaction is complete, generally about 16 hours. Standard reaction conditions may comprise the use of a molar excess of suitable base, such as sodium, potassium hydroxide, triethylamine, diisopropylethylamine, N methylmorpholine (NMM), or pyridine, or in some cases where LG is hydroxyl, a peptide coupling reagent, such as O (7 azabenzotriazol 1 yl) N,N,N',N' tetra methyluronium hexafluorophosphate (HATU), may be used. When the reaction is substantially complete, the product is subjected, if necessary, to a deprotection sequence under standard reaction conditions (e.g., THF, CH$_2$Cl$_2$, or the like, a molar excess of acid such as acetic acid, formic acid, trifluoroacetic acid, or the like as described herein) to yield isolated by conventional means.

The compounds of Formula (II) may also be prepared according to the synthetic sequence shown in Scheme B from commercially available reactant (1) or prepared by means well known in the art. Formula 3 can be prepared from reactant 1 via hydrogenation. In general the reactants (1) is hydrogenated using paladium catalyst such as Pd/C, Pd(OH)2, in solvent such as ethanol or by transfer hydrogenation. Formula 3 is then coupled with commercially available reactant 2 by means well known in the art. In general, the reactants (1) and at least one molar equivalent, and preferably a slight excess (e.g., 1.2 to 1.5 molar equivalents) of (2), as shown in Scheme A, are combined under standard reaction conditions in an inert solvent, such as dimethylformamide (DMF), at a temperature of about 25° C. until the reaction is complete, generally in about 16 hours. Standard reaction conditions may comprise the use of a molar excess of suitable base, such as sodium or potassium hydroxide, triethylamine, diisopropylethylamine, N methylmorpholine (NMM), or pyridine, or in some cases where LG is hydroxyl, a peptide coupling reagent, such as 0 (7 azabenzotriazol-1-yl) N,N,N',N' tetra methyluronium hexafluorophosphate (HATU), may be used. When the reaction is substantially complete, the product is subjected, if necessary, to a deprotection sequence under standard reaction conditions (e.g., THF, CH2Cl2, or the like, a molar excess of acid such as acetic acid, formic acid, trifluoroacetic acid, or the like as described herein) to yield isolated by conventional means.

Scheme B

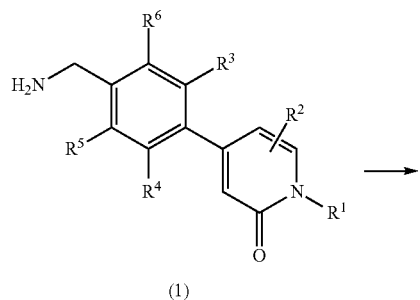

(1)

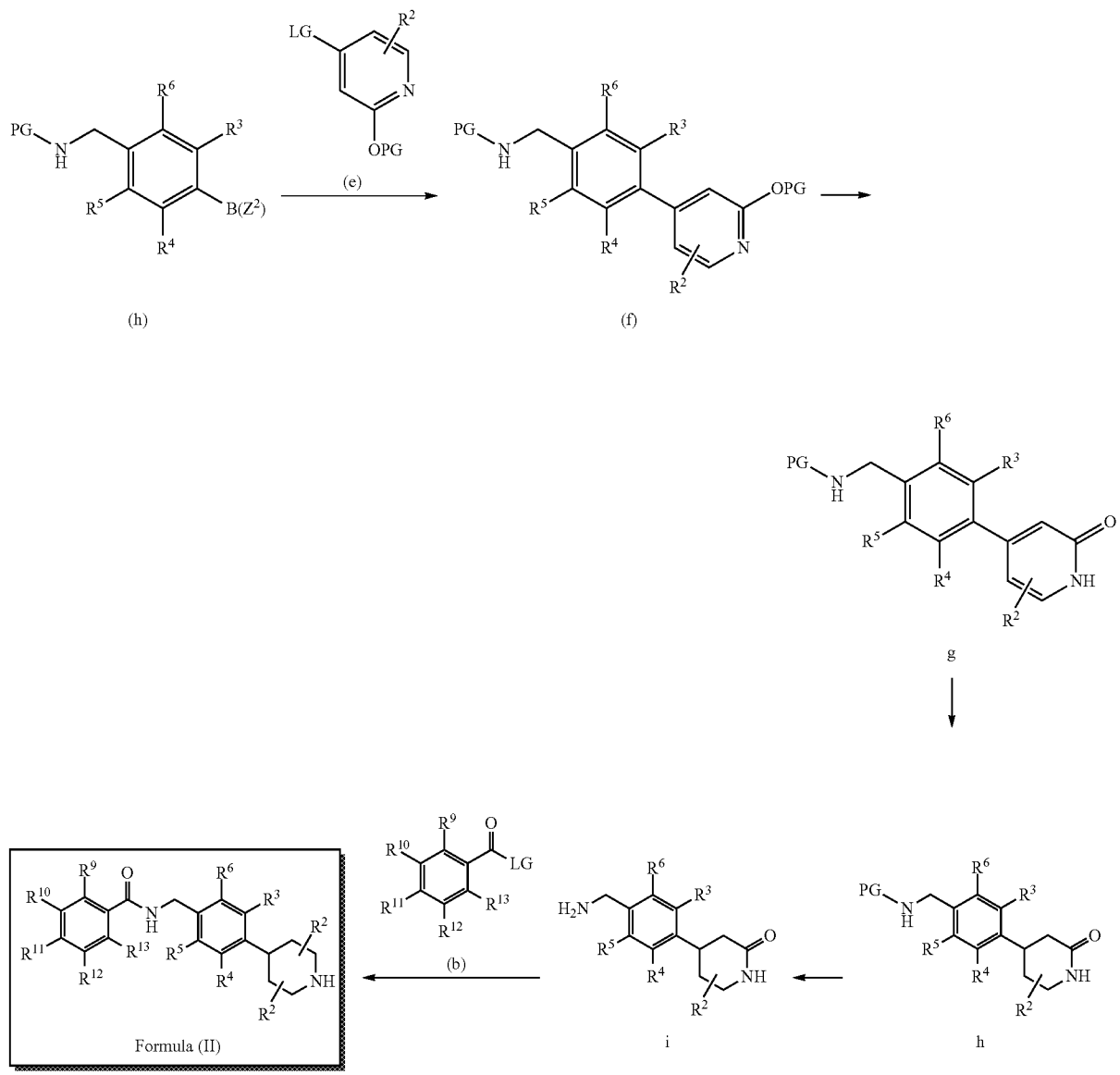

The compounds of Formula (II) may be prepared according to the synthetic sequence shown in Scheme C by the coupling an arylboronic acid derivative, (h), and a substituted pyridine, (e), under standard Suzuki reaction conditions (e.g., molar equivalents of (h) and (e) in dry DMF, under argon atmosphere at elevated temperatures, with approximately 5-10 molar % of palladium catalyst and a molar excess of inorganic base such as potassium carbonate, as described herein to produce the substituted pyridine derivative (f) which is converted to the pyridin-2(1H)-ones (g) following deprotection (e.g., THF, CH$_2$Cl$_2$, or the like, a molar excess of acid such as acetic acid, formic acid, trifluoroacetic acid, or the like as described herein). Reactant pyridin-2(1H)-one (g) can be hydrogenated using palladium catalyst such as Pd/C, Pd(OH)2, in a solvent such as ethanol or by transfer hydrogenation to produce piperidone (h) which may be converted to amine (i) which in turn may be converted to formula II.

Repairing Compounds of Formula II

Pharmaceutical Compositions

In certain aspects, pharmaceutical compositions are provided comprising a therapeutically effective amount of a compound of Formula (I) and at least one pharmaceutically acceptable carrier.

The compounds of Formula (I) are usually administered in the form of pharmaceutical compositions. Therefore, pharmaceutical compositions are provided that contain, as the active ingredient, one or more of the compounds of Formula (I), or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants.

The compounds of Formula (I) may be administered alone or in combination with other therapeutic agents. Such compositions are prepared in a manner well known in the pharmaceutical art (see, e.g., *Remington's Pharmaceutical Sciences*, Mace Publishing Co., Philadelphia, Pa. 17$^{th}$ Ed. (1985) and *Modern Pharmaceutics*, Marcel Dekker, Inc. 3$^{rd}$ Ed. (G. S. Banker & C. T. Rhodes, Eds.).

Methods of Use

In certain aspects, methods of using the compounds of Formula (I) in the treatment of addiction to a dopamine-producing agent are provided. The method comprises administering to a mammal in need thereof a therapeutically effective dose of a compound of Formula (I). Such diseases include, but are not limited to, the treatment of dependency upon cocaine, opiates, amphetamines, nicotine, and alcohol. In certain embodiments, the compounds of Formula (I) are generally effective in the treatment of conditions that respond to the administration of ALDH-2 inhibitors. While not wishing to be bound by theory, it is believed that the compounds described herein are effective in treating addiction as a consequence of their ability to normalize the increased dopamine levels associated with various addictive behaviors. See, N. D. Volkow et al., Dopamine in drug abuse and addiction: results from imaging studies and treatment implications, *Mol. Psychiatry* 9 (2004), pp. 557-569; and B. J. Everitt and M. E. Wolf, Psychomotor stimulant addiction: a neural systems perspective, *J. Neurosci.* 22 (2002), pp. 3312-3320. Addictive behavior has been shown to include addiction to food particularly sugary foods. For example, in the manuscript "Evidence for sugar addiction: Behavioral and neurochemical effects of intermittent, excessive sugar intake" (Hoebel et. Al. *Neurosci Biobehav Rev.* 2008; 32(1): 20-39), the authors wrote "What this review demonstrates is that rats with intermittent access to food and a sugar solution can show both a constellation of behaviors and parallel brain changes that are characteristic of rats that voluntarily self-administer addictive drugs. In the aggregate, this is evidence that sugar can be addictive."

Given this proposed mechanism of action, the compounds of Formula (I) are useful, for example, in the treatment of addictive and compulsive behaviors and neurological conditions associated with increased dopamine levels as described, for example, in the published U.S. patent application 20100113483. Such behaviors and conditions include, but are not limited to, compulsive gambling, overeating, and shopping, obsessive compulsive disorder (OCD), schizophrenia, attention deficit hyperactivity disorder, anxiety and the like. In certain embodiments, the compounds described herein have also been shown to be effective in treating compulsive eating disorders and obesity.

Another aspect pertains to methods of modulating (e.g., reducing) alcohol consumption, alcohol dependence and/or alcohol abuse for therapeutic purposes. Accordingly, in an exemplary embodiment, the modulatory method involves contacting ALDH-2 with a compound that inhibits ALDH-2. In yet another exemplary embodiment, the modulatory method involves administering a compound that increases the concentration of an aldehyde (e.g., 5-HIAL and/or DOPAL) formed during catabolism of a neurotransmitter (e.g., 5-HT/serotonin and/or DA/dopamine). Preferably, the compound does not inhibit MAO, or inhibits MAO only to a small degree.

Another embodiment involves a method of modulating alcohol consumption for the treatment of alcohol abuse or dependence which includes the step of administering to a patient a therapeutically effective amount of a compound which inhibits ALDH-2, and/or increases the concentration of an aldehyde (e.g., 5-HIAL and/or DOPAL) formed during catabolism of a neurotransmitter (e.g., 5-HT and/or DA).

In certain embodiments, is provided a method of modulating alcohol consumption in a mammal comprising administering a compound of Formula (I), or a pharmaceutical composition thereof, in an amount effective to increase a concentration of an aldehyde formed during catabolism of a neurotransmitter. In certain embodiments, the neurotransmitter is serotonin or dopamine. In certain embodiments, the aldehyde is 5-hydroxyindoleacetaldehyde or 3,4-dihydroxyphenylacetaldehyde. In certain embodiments, the compound does not inhibit monoamine oxidase.

Testing

Activity testing is conducted as described in those patents and patent applications referenced above, and in the Examples below, and by methods apparent to one skilled in the art. For example, as described in "The Mitochondrial Monoamine Oxidase-Aldehyde Dehydrogenase Pathway: A Potential Site of Action of Daidzein", J. Med. Chem. 2000, 43, 4169-4179. In general, the compounds of Formula (I) are assayed to determine their effects on MAO and ALDH-2 independently using the membrane and lysate of a density-gradient-purified mitochondria preparation as the respective enzyme sources. The results are expressed in $IC_{50}$ values.

Monitoring the influence of a compound of Formula (I) on the modulation of alcohol consumption, dependence and/or abuse in a patient can be determined by a screening assay as described herein and as described, for example, in the published U.S. patent application 20040068003. In such an assay, decreased consumption of alcohol can be used to measure the effectiveness of compounds of Formula (I).

For example, and not by way of limitation, ALDH-2 activity is decreased in cells treated with a compound of Formula (I) which inhibits ALDH-2 and as a consequence diverts part of 5-HT metabolic flux from the oxidative pathway, which leads to the formation of 5-hydroxyindoleacetic acid (5-HIAA), to the reductive pathway, further leading to the formation of 5-hydroxytryptophol (5-HTOL). Thus, to study the effect of a compound of Formula (I) on alcohol dependence and/or abuse, for example, in a clinical trial, urine samples can be collected and levels of 5-HIAA and 5-HTOL in the samples can be determined. Decreased levels of 5-HIAA and increased levels of 5-HTOL will indicate inhibition of ALDH-2 activity. In this way, the urine [5-HTOL]/[5-HIAA] ratio can serve as a marker, indicative of the physiological response of the cells to the compound. Accordingly, this response state may be determined before, and at various points during treatment of the individual with the compound.

In one embodiment, is provided a method for monitoring the effectiveness of treatment of a subject with a compound of Formula (I) including the steps of (i) obtaining pre-administration urine samples from a subject before and after alcohol detoxification but prior to administration of the compound of Formula (I); (ii) determining the [5-HTOL]/[5-HIAA] ratios in the pre-administration samples; (iii) obtaining one or more post-administration samples from the subject; (iv) determining the [5-HTOL]/[5-HIAA] ratio in the post-administration samples; (v) comparing the [5-HTOL]/[5-HIAA] ratios in the pre-administration samples with that in the post administration sample or samples; and (vi) altering the administration of the compound of Formula (I) to the subject accordingly. According to such an embodiment, ALDH-2 inactivation and/or an increase in urine [5-HTOL]/[5-HIAA] ratio may be used as an indicator of the effectiveness of the compound of Formula (I), even in the absence of an observable phenotypic response.

Administration

The compounds of Formula (I) are usually administered in the form of pharmaceutical compositions. Therefore provided herein are pharmaceutical compositions that contain, as the active ingredient, one or more of the compounds of Formula (I), or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The compounds of Formula I may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17$^{th}$ Ed. (1985) and "Modern Pharmaceutics", Marcel Dekker, Inc. 3$^{rd}$ Ed. (G. S. Banker & C. T. Rhodes, Eds.).

The compounds of Formula (I) may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parental, particularly by injection. The forms in which the novel compositions may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of Formula (I) in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the known methods of preparation include vacuum-drying and freeze-drying techniques which yield a powder of the active ingredient plus any additional desired ingredient from a previously sterile-filtered solution thereof.

Oral administration is another route for administration of the compounds of Formula (I). Administration may be via capsule or enteric coated tablets, or the like. In making the pharmaceutical compositions that include at least one compound of Formula (I), the active ingredient is usually diluted by an excipient and/or enclosed within such a carrier that can be in the form of a capsule, sachet, paper or other container. When the excipient serves as a diluent, it can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods employs transdermal delivery devices ("patches"). Such transdermal patches may be used to provide continuous or discontinuous infusion of the compounds in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, or ampoule). The compounds of Formula (I) are effective over a wide dosage range and is generally administered in a pharmaceutically effective amount. Preferably, for oral administration, each dosage unit contains from about 10 mg to 1 g of a compound of Formula (I), more preferably from 10 to 700 mg, and for parenteral administration, preferably from 10 to 700 mg of a compound of Formula (I), more preferably about 50-300 mg. Preferred dose regimens may also include administering about 100-300 mg twice daily to a patient in need thereof. Nonetheless, it will be understood, that the amount of the compound of Formula (I) actually administered will be determined by a physician, in light of the relevant circumstances of the patient, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound. When referring to these preformulation compositions as homogeneous, it is meant that the active ingredient is dispersed evenly throughout the composition so that the composition may be readily subdivided into equally effective unit dosage forms such as tablets, pills and capsules.

Tablets or pills may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

The following examples are included to demonstrate certain embodiments. It should be appreciated by those of skill in the art that the techniques disclosed in the examples which follow represent techniques discovered by the inventor to function well in the practice, and thus can be considered to constitute modes for its practice. However, those of skill in the art should, in light of the present disclosure, appreciate that many changes can be made in the specific embodiments which are disclosed and still obtain a like or similar result without departing from the spirit and scope.

EXAMPLES

Unless otherwise stated all temperatures are in degrees Celsius (° C.). Also, in these examples and elsewhere, abbreviations and acronyms have the following meanings:
Abbreviation Meaning
° C. Degree Celsius
5-HIAA 5-Hydroxyindoleacetic acid
5-HIAL 5-Hydroxyindoleacetaldehyde
5-HT 5-Hydroxytryptamine (serotonin)
5-HTOL 5-Hydroxytryptophol
Ae Enzyme activities measured in the presence of a test compound
AIDS Acquired immune deficiency syndrome
ALDH-2 Human mitochondrial aldehyde dehydrogenase
Ao Enzyme activities measured in the absence of a test compound
BHA Butylated hydroxy anisole
BOC tert-Butoxycarbonyl
BOP Benzotriazolyl-N-hydroxytris(dimethyamino)phosphonium hexafluorophosphate
Cbz Benzyl carbamate
cm centimeter
d Doublet
dd Doublet of doublets
DA Dopamine
DCC Dicyclohexyl carbodiimide
DCM Dichloromethone
DIC Diisopropyl carbodiimide
DIEA N,N-Diisopropylethylamine
DMF Dimethylformamide
DMSO Dimethylsulfoxide
dt Doublet of triplets
EDTA Ethylenediaminetetraacetic acid
equiv/eq Equivalents
EtOAc Ethyl acetate
EtOH Ethanol
FR Fixed ratio
g Grams
HATU O-(7-Azabenzotriazol-1-yl)-N,N,N',N'-tetramethyluronium hexafluorophosphate
HBTU O-Benzotriazole-N,N,N',N'-tetramethyl-uronium-hexafluoro-phosphate
HPLC High-performance liquid chromatography
hrs/h Hours
Hz Hertz
$IC_{50}$ The half maximal inhibitory concentration
IIDQ 1-Isobutoxycarbonyl-2-isobutoxy-1,2-dihydro quinone
ip Intraperitoneal
iv Intravenous
J Coupling constant
Kg Kilogram
L Liter
LAD Low alcohol-drinking rat
LCMS/LC-MS Liquid chromatography-mass spectrometry
LG Leaving group
M Molar
m/z mass-to-charge ratio
M+ Mass peak
M+H Mass peak plus hydrogen
M+Na Mass peak plus sodium
MAO Monoamine oxidase
Me Methyl
mg Milligram
MHz Megahertz
min Minute
ml/mL Milliliter
mM Millimolar
mmol Millimole
MOM Methoxylmethyl
MS Mass spectroscopy
NAD Nicotinamide Adenine Dinucleotide
NaPPi Sodium pyrophosphate
NIH National Institute of Health
NMM N-Methylmorpholine
NMR Nuclear magnetic resonance
NP Alcohol non-preferring rat
OCD Obsessive compulsive disorder
PG Protecting group Ph Phenyl
PyBOP (Benzotriazol-1-yloxy)tripyrrolidinophosphonium hexafluorophosphate
q.s. Quantity sufficient to achieve a stated function
RT/rt/R.T Room temperature
s Second
s Singlet
SA Self-administration
sc Subcutaneous
SEM Standard error of means
t Triplet
TEA Triethylamine
TES Triethylsilyl
TFA Trifluoroacetic acid
THF Tetrahydrofuran
TIPS Triisopropylsilyl
TKK TKK buffer
TLC Thin layer chromatography
TMS Trimethylsilyl
TO Time out
Tris tris(hydroxymethyl)aminomethone
δ Chemical shift
μg Microgram
μL/μl Microliter
μM Micromolar
μmol Micromole Example 1

The preparation of 2,6-dichloro-4-(2-methoxyethoxy)-N-(4-(2-oxo-1,2-dihydropyridin-4-yl)benzyl)benzamide (1) according to the synthetic route of Scheme I

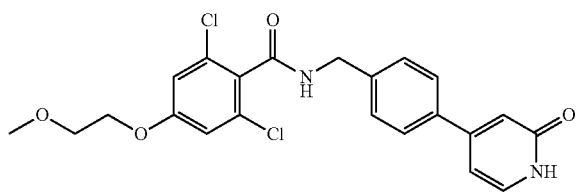 [SMILES: COCCOc1cc(Cl)c(C(=O)NCc2ccc(-c3cc[nH]c(=O)c3)cc2)c(Cl)c1]

Step 1—The preparation of 2,6-dichloro-4-(2-methoxyethoxyl)benzaldehyde 2,6-Dichloro-4-hydroxybenzaldehyde (0.5 g, 2.62 mmol), 1-bromo-2-methoxyethone (0.3 mL), sodium iodide (0.4 g, 0.4 mmol) and potassium carbonate (0.9 g, 6.55 mmol) were added in DMF (5 mL) and heated at 100° C. for 1 h under stirring. When the reaction was done, the reaction mixture was diluted with EtOAc and extracted three times with water. The organic phase was dried over magnesium sulfate, filtered and concentrated in vacuum. The resulting solid was purified by normal phase chromatography (hexanes:EtOAc 3:1) to afford 2,6-dichloro-4-(2-methoxyethoxy)benzaldehyde.

Step 2—The preparation of 2,6-dichloro-4-(2-methoxyethoxyl)benzoic acid 2,6-Dichloro-4-(2-methoxyethoxyl)benzaldehyde (0.5 g, 2.0 mmol) in acetone (20 mL) were cooled down in ice bath and then potassium permanganate (0.47 g, 3.0 mmol) in water (5 mL) was added slowly under vigorous stirring. The reaction mixture was warmed up slowly to room temperature and reacted over 24 h. The reaction mixture was filtered through celite and washed with acetone. The organic phase was evaporated and then re-dissolved in EtOAc to be extracted with 1N HCl aqueous solution. The organic phase was dried over magnesium sulfate, filtered and concentrated in vacuum to afford the compound 2,6-dichloro-4-(2-methoxyethoxyl)benzoic acid.

Step 3—The preparation of N-(4-bromobenzyl)-2,6-dichloro-4-(2-methoxyethoxyl)benzamide 2,6-Dichloro-4-(2-methoxyethoxyl)benzoic acid (0.1 g, 0.23 mmol), (4-bromophenyl) methanamine hydrochloride (0.1 g, 0.27 mmol), 2-(1H-7-azabenzotriazol-1-yl)-1,1,3,3-tetramethyl uronium hexafluorophosphate methanaminium (HATU) (0.17 g, 0.27 mmol), and triethylamine (0.15 mL, 0.7 mmol) were combined in DMF (3 mL) and then stirred at room temperature until reaction was completed. The reaction mixture was diluted with ethyl acetate and washed with water and twice with a saturated sodium bicarbonate solution. The organic phase was dried over magnesium Scheme VII

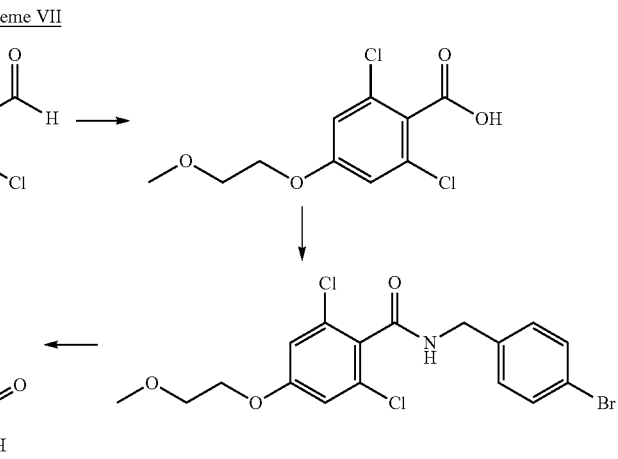

sulfate, filtered and concentrated in vacuum. The solid resulting was used for next step without further purification.

Step 4—The preparation of 2,6-dichloro-4-(2-methoxyethoxy)-N-(4-(2-oxo-1,2-dihydropyridin-4-yl)benzyl)benzamide N-(4-Bromobenzyl)-2,6-dichloro-4-(2-methoxyethoxyl) benzamide (0.11 g, 0.25 mmol), 2-tert-butoxy-4-(4,4,5,5-tetramethyl-1,3,2-dioxaborolan-2-yl)pyridine (0.085 g, 0.3 mmol), cesium carbonate (0.21 g, 0.75 mmol), and [1,1' Bis(diphenyl phosphino(ferrocene]dichloropalladium(II) (15 mg, 0.025 mmol) were dissolved in degassed DMF (3 mL) and H₂O (1.5 mL). The reaction mixture was degassed by bubbling nitrogen through for 15 min and then heated in the microwave at 85° C. for 20 min. The reaction mixture was diluted with EtOAc and extracted with water. The organic phase was dried over magnesium sulfate, filtered and concentrated in vacuum. The crude product was suspended in hot acetonitrile and the solids filtered out to have the pure compound N-(4-(2-tert-butoxypyridin-4-yl)benzyl)-2,6-dichloro-4-(2-methoxy ethoxy)benzamide that was used for next step without further purification.

Compound N-(4-(2-tert-butoxypyridin-4-yl)benzyl)-2,6-dichloro-4-(2-methoxy ethoxy)benzamide was re-dissolved in DCM (2 mL) and trifluoroacetic acid (2 mL) and stirred at room temperature for 1 h. after the reaction was done it was concentrated in vacuum and then purified by reverse phase chromatography to afford 2,6-dichloro-4-(2-methoxyethoxy)-N-(4-(2-oxo-1,2-dihydropyridin-4-yl)benzyl)benzamide.

MS found for $C_{22}H_{20}Cl_2N_2O_4$ as $(M+H)^+$ 448.32 $^1H$ NMR (400 MHz, dmso-$d_6$): $^1$H-NMR (DMSO) δ: 11.58 (s, 1H), 9.10 (t, J=6.0 Hz, 1H), 7.66 (d, J=8.4 Hz, 2H), 7.46 (d, J=8.0 Hz, 2H), 7.4 (s, 1H), 7.12 (s, 2H), 6.56 (s, 1H), 6.48 (d, J=5.2 Hz, 1H), 4.47 (d, J=6.0 Hz, 2H), 4.16 (t, J=4.4 Hz, 2H), 4.62 (t, J=4.4 Hz, 2H), 3.27 (s, 3H).

Example 2

The preparation of 2,6-dichloro-N-[4-(2-oxo-1,2-dihydro-pyridin-4-yl)-benzyl]-benzamide (2) according to the synthetic route of Scheme II

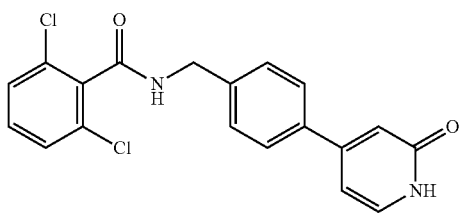 [SMILES: O=C(NCc1ccc(-c2cc[nH]c(=O)c2)cc1)c1c(Cl)cccc1Cl]

Scheme VIII

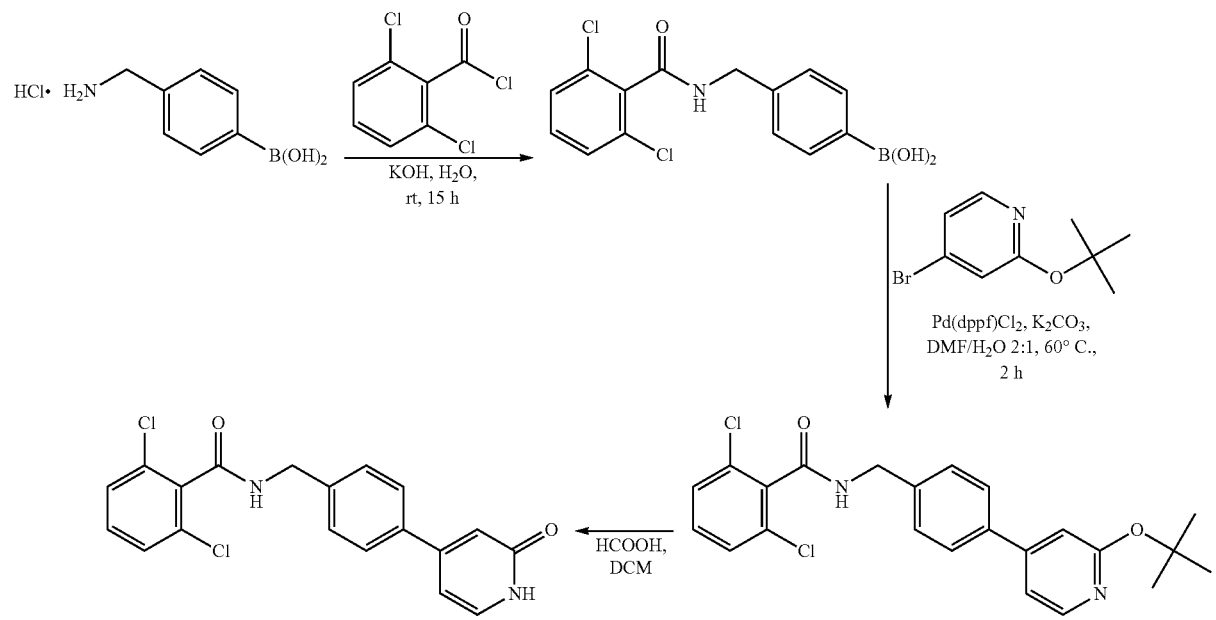

Step 1—The preparation of 4-[(2,6-dichloro-benzoylamino)methyl]phenylboronic acid

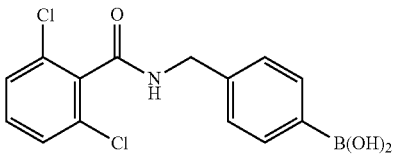 [SMILES: O=C(NCc1ccc(B(O)O)cc1)c1c(Cl)cccc1Cl]

4-(Aminomethyl)phenylboronic acid hydrochloride (5 g, 26.7 mmol) was dissolved in 25 mL water. 16 mL 50% aqueous KOH solution was added followed by 2,6-dichlorobenzoyl chloride (6.7 g, 32 mmol). The mixture was stirred rapidly at room temperature over night. Acidification with 1N HCl gave a thick, white precipitate which was filtered, washed with water and dried giving 4-[(2,6-dichloro-benzoylamino)methyl]phenylboronic acid as a white powder in quantitative yield.

Step 2—The preparation of N-[4-(2-tert-butoxy-pyridin-4-yl)-benzyl]-2,6-dichloro-benzamide

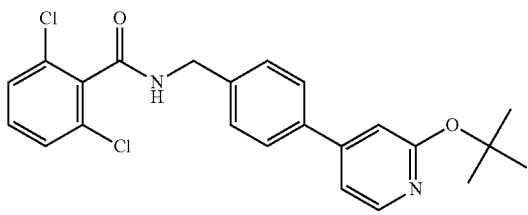 [SMILES: CC(C)(C)Oc1cc(-c2ccc(CNC(=O)c3c(Cl)cccc3Cl)cc2)ccn1]

4-[(2,6-Dichloro-benzoylamino)methyl]phenylboronic acid (5 g, 15.4 mmol), potassium carbonate (5 g), and [1,1'-bis(diphenylphosphino)ferrocene]dichloropalladium (II) (0.56 g, 0.77 mmol) were combined in a round bottom flask. 4-Bromo-2-(t-butoxy) pyridine (3.55 g, 15.4 mmol) was dissolved in 20 mL DMF and added to the flask under stirring. The flask was flushed with nitrogen and 10 mL water was added. The reaction mixture was stirred at 70° C. for two hours. After cooling the mixture was poured into 300 mL ethyl acetate and washed with water and brine. The organic phase was dried with magnesium sulfate and evaporated under vacuum. The crude N-[4-(2-tert-butoxy-pyridin-4-yl)-benzyl]-2,6-dichloro-benzamide was further purified by silica gel chromatography (eluent: hexone/ethyl acetate 1:1).

Step 3—The preparation of 2,6-Dichloro-N-[4-(2-oxo-1,2-dihydro-pyridin-4-yl)-benzyl]-benzamide

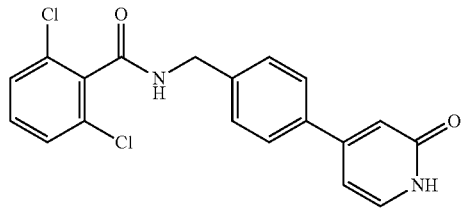 [SMILES: O=C(NCc1ccc(-c2cc[nH]c(=O)c2)cc1)c1c(Cl)cccc1Cl]

N-[4-(2-tert-Butoxy-pyridin-4-yl)-benzyl]-2,6-dichloro-benzamide was dissolved in 30 mL dichloromethone and 12 mL of 98% formic acid. The mixture was stirred at 40° C. for three hours after which the volatile components were evaporated under vacuum. The residue was triturated with ethyl acetate, filtered, washed with ethyl acetate and dried giving 2,6-dichloro-N-[4-(2-oxo-1,2-dihydro-pyridin-4-yl)-benzyl]-benzamide (4.34 g, 75.5% yield over two steps) as white powder. $C_{19}H_{14}Cl_2N_2O_2$; MS m/z: 373 (MH$^+$) $^1$H NMR (DMSO-d$_6$): δ 11.56 (s, 1H), δ 9.21 (t, J=5.6 Hz, 1H), δ 7.67 (d, J=8.0 Hz, 2H), δ 7.46 (m, 6H), δ 6.57 (d, J=1.2 Hz, 1H), δ 6.49 (dd, J=6.8 Hz, J'=1.6 Hz, 1H), δ 4.50 (d, J=6.0 Hz, 2H.

Example 3

A. The preparation of 2-chloro-3-fluoro-N-(4-(2-oxo-1,2-dihydropyridin-4-yl)benzyl)benzamide (3) according to the synthetic route of Scheme III

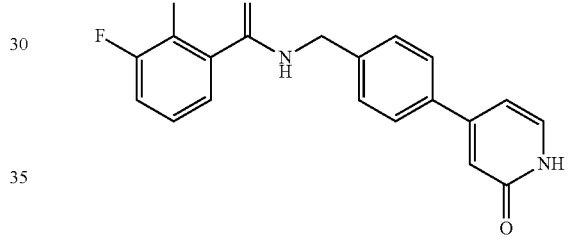

Scheme IX

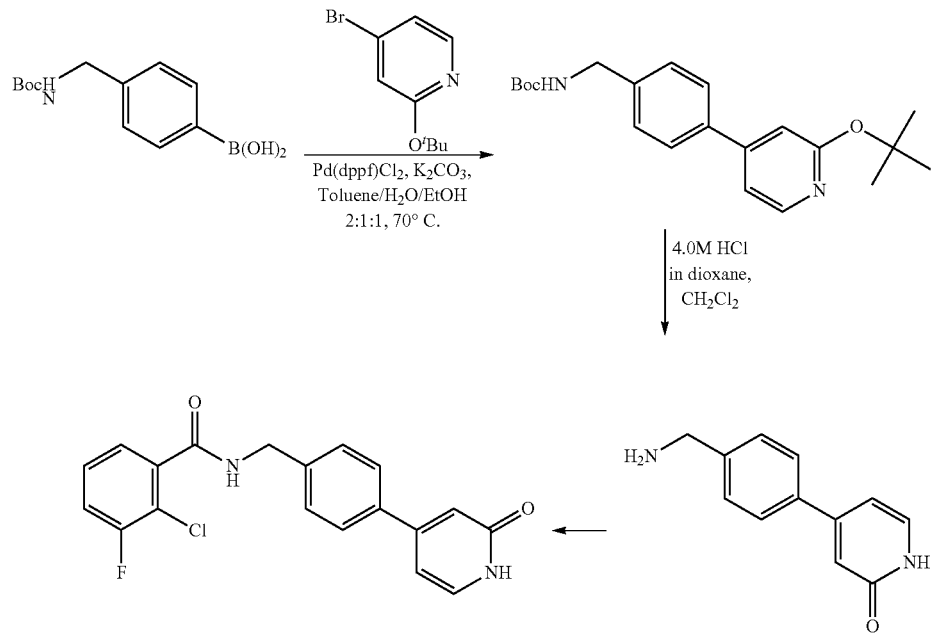

Step 1—The preparation of 4-(4-(aminomethyl)phenyl)pyridin-2(1H)-one

To a solution of 4-((tert-butoxycarbonylamino)methyl) phenylboronic acid (1 g, 3.98 mmol), potassium carbonate (1.1 g, 7.96 mmol), 4-Bromo-2-(t-butoxy)pyridine (1.1 g, 4.78 mmol) in degassed toluene/EtOH/water (2:1:1) (6 mL) was added [1,1'-Bis(diphenylphosphino)ferrocene]dichloropalladium (II) (0.14 g, 0.199 mmol). The reaction mixture was then heated in the microwave at 75° C. for 30 min. After cooling the mixture, it was purified by silica gel chromatography (eluent: $CH_2Cl_2$/ethyl acetate 95:5) to yield tert-butyl 4-(2-tert-butoxypyridin-4-yl)benzylcarbamate (1). MS found for $C_{21}H_{28}N_2O_3$ as $(M+H)^+$ 356.8. To the above Boc protected compound (462 mg, 1.3 mmol) in $CH_2Cl_2$ (3 mL), 4.0 M HCl dioxane (1.6 mL, 6.5 mmol) was added and stirred at rt for 1 h. The reaction mixture was then diluted with ether and the resulting solids were filtered and washed with ether and dried to give 4-(4-(aminomethyl)phenyl) pyridin-2(1H)-one (2) as hydrochloride salt. $C_{12}H_{12}N_2O$ 201.0 (M+1).

Step 2—The preparation of 2-chloro-3-fluoro-N-(4-(2-oxo-1,2-dihydropyridin-4-yl)benzyl)benzamide To the above amine (50 mg, 0.212 mmol), 2-chloro-3-fluorobenzoic acid (48 mg, 0.276 mmol), HATU (121 mg, 0.318 mmol), in DMF (1 mL) was added NMM (0.06 mL, 0.53 mmol) and stirred at rt for 16 hours. The reaction mixture was diluted with water and acetonitrile and the resulting solid was filtered and washed with ether and dried to give 2-chloro-3-fluoro-N-(4-(2-oxo-1,2-dihydropyridin-4-yl)benzyl)benzamide.

MS found for $C_{19}H_{14}ClFN_2O_2$ as $(M+H)^+$ 357.1 $^1H$ NMR (400 MHz, dmso-$d_6$): δ: 11.56 (br, 1H), 9.13 (t, J=6.0 Hz, 1H), 7.68 (d, J=8.0 Hz, 2H), 7.50-7.42 (m, 4H), 7.32 (d, J=7.2 Hz, 2H); 6.56 (s, 1H), 6.50 (d, J=7.2 Hz, 1H); 4.49 (d, J=6.0 Hz, 2H).

B. The Preparation of Additional Compounds of Formula (I) According to the Synthetic Route of Scheme III The preparation n of 2-chloro-6-methyl-N-(4-(2-oxo-1,2-dihydropyridin-4-yl)benzyl)benzamide (4):

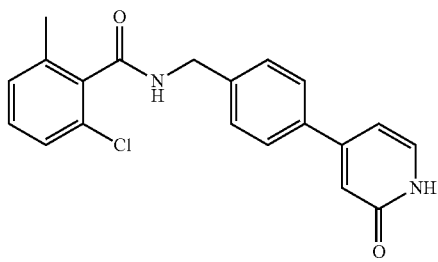 [SMILES: Cc1cccc(Cl)c1C(=O)NCc1ccc(-c2cc[nH]c(=O)c2)cc1]

Compound (4) was prepared using a similar procedure as that described for Compound (3) with the appropriate starting materials. MS found for $C_{20}H_{17}ClN_2O_2$ as $(M+H)^+$ 353.1 $^1H$ NMR (400 MHz, dmso-$d_6$): δ: 11.54 (br, 1H), 9.04 (t, J=6.0 Hz, 1H), 7.68 (d, J=8.0 Hz, 2H), 7.47 (d, J=8.0 Hz, 2H), 7.45 (d, J=7.2 Hz, 2H), 7.30-7.19 (m, 3H), 6.56 (s, 1H), 6.50 (d, J=7.2 Hz, 1H); 4.49 (d, J=6.0 Hz, 2H); 2.22 (s, 3H).

The preparation of 2,6-dimethyl-N-(4-(2-oxo-1,2-dihydropyridin-4-yl)benzyl)benzamide (5)

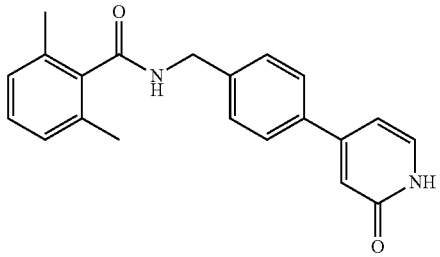

Compound (5) was prepared using a similar procedure as that described for Compound (3) with the appropriate starting materials. MS found for $C_{23}H_{20}N_2O_2$ as $(M+H)^+$ 353.1 $^1H$ NMR (400 MHz, dmso-$d_6$): δ: 11.55 (br, 1H), 8.86 (t, J=6.0 Hz, 1H), 7.68 (d, J=8.0 Hz, 2H), 7.45-7.40 (m, 3H), 7.16 (t, J=8.0 Hz, 1H), 7.02 (d, J=7.2 Hz, 2H), 6.56 (s, 1H), 6.50 (d, J=7.2 Hz, 1H); 4.47 (d, J=6.0 Hz, 2H); 2.18 (s, 6H).

The preparation of 2,6-Dichloro-N-[4-(6-methyl-2-oxo-1,2-dihydro-pyridin-4-yl)-benzyl]-benzamide (6)

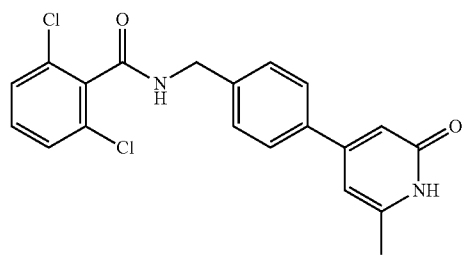 [SMILES: Cc1cc(-c2ccc(CNC(=O)c3c(Cl)cccc3Cl)cc2)cc(=O)[nH]1]

Compound (6) was prepared using a similar procedure as that described for Compound (3) with the appropriate starting materials. $^1H$-NMR (DMSO) δ: 11.55 (br, 1H), 9.21 (t, J=6.0 Hz, 1H), 7.65 (d, J=8.0 Hz, 2H), 7.52-7.40 (m, 5H), 6.38 (s, 1H), 6.35 (s, 1H), 4.50 (d, J=6.0 Hz, 2H), 2.21 (s, 3H). MS: 387/389 (MH$^+$).

Example 4

A. The preparation of 2-chloro-3,6-difluoro-N-(4-(2-oxo-1,2-dihydropyridin-4-yl)benzyl)benzamide (7) according to the synthetic route of Scheme IV

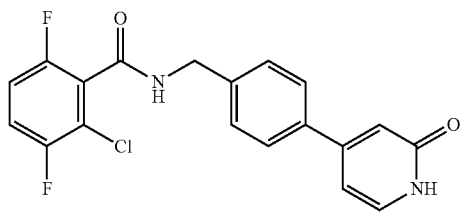 [SMILES: O=C(NCc1ccc(-c2cc[nH]c(=O)c2)cc1)c1c(F)ccc(F)c1Cl]

Scheme X

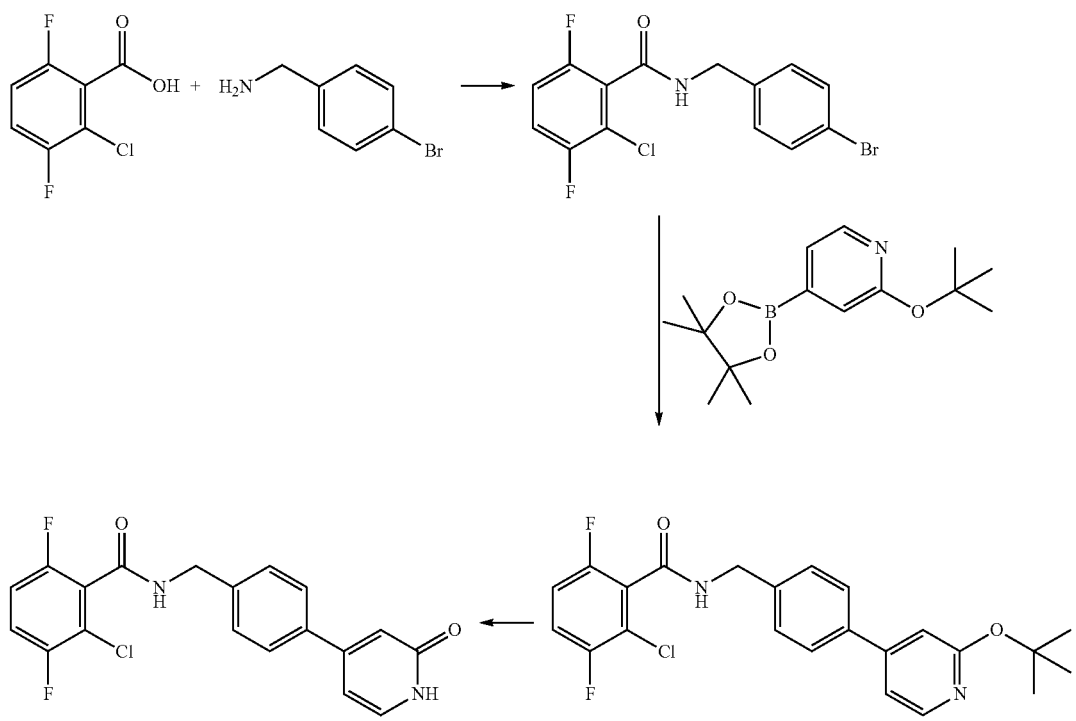

Step 1—The preparation of N-(4-bromobenzyl)-2-chloro-3,6-difluorobenzamide (4-Bromophenyl) methanamine hydrochloride (0.5 g, 2.25 mmol), 2-chloro-3,6-difluorobenzoic acid (0.52 g, 2.7 mmol), 2-(1H-7-azabenzotriazol-1-yl)-1,1,3,3-tetra methyl uronium hexafluorophosphate methanaminium (HATU) (1.2 g, 2.7 mmol), and N,N-diisopropyl-ethylamine (1.17 mL, 6.75 mmol) were combined in DMF (6 mL) and then stirred at room temperature for 1 h. The reaction mixture was diluted in ethyl acetate and washed once with water and twice with an aqueous saturated sodium bicarbonate solution. The organic phase was dried over magnesium sulfate, filtered and concentrated in vacuum. The crude product was suspended in hot acetonitrile and then filtered to have the pure compound N-(4-bromobenzyl)-2-chloro-3,6-difluorobenzamide.

Step 2—The preparation of 2-tert-butoxy-4-(4,4,5,5-tetramethyl-1,3,2-dioxaborolan-2-yl)pyridine 4-Bromo-2-tert-butoxypyridine (1.0 g, 4.34 mmol), pinacoldiboron (1.32 g, 5.2 mmol), potassium acetate (1.28 g, 5.2 mmol) and [1,1' Bis(diphenylphosphino(ferrocene]dichloropalladium(II) (0.318 g, 0.52 mmol) were dissolved in degassed DMF (8 mL) and H$_2$O (4 mL). This mixture was heated at 85° C. for 20 min. The reaction mixture was extracted with EtOAc in presence of water. The organic phase was dried over magnesium sulfate, filtered and concentrated in vacuum. The solids were purified by column (hexone:EtOAc, 3:1) to yield the pure compound 2-tert-butoxy-4-(4,4,5,5-tetramethyl-1,3,2-dioxaborolan-2-yl) pyridine.

Step 3—The preparation of N-(4-(2-tert-butoxypyridin-4-yl)benzyl)-2-chloro-3,6-difluorobenzamide Compound N-(4-bromobenzyl)-2-chloro-3,6-difluorobenzamide (0.2 g, 0.55 mmol), 2-tert-butoxy-4-(4,4,5,5-tetramethyl-1,3,2-dioxaborolan-2-yl)pyridine (0.17 g, 0.6 mmol), Cs$_2$CO$_3$ (0.54 g, 1.65 mmol), and [1,1' Bis(diphenyl phosphino (ferrocene]dichloro palladium (II) (40 mg, 0.05 mmol) were dissolved in degassed DMF (3 mL) and H$_2$O (1.5 mL). The reaction mixture was degassed again by bubbling nitrogen through for 15 min and then heated in the microwave at 85° C. for 20 min. The reaction mixture was diluted with EtOAc and extracted two times with water. The organic phase was dried over magnesium sulfate, filtered and concentrated in vacuum. The crude product was heated in acetonitrile and the solids filtered to have the pure compound N-(4-(2-tert-butoxypyridin-4-yl)benzyl)-2-chloro-3,6-difluorobenzamide that was used for next step without further purification.

The compound N-(4-(2-tert-butoxypyridin-4-yl)benzyl)-2-chloro-3,6-difluorobenzamide was re-dissolved in DCM (2 mL) and trifluoroacetic acid (2 mL) and stirred at room temperature for 1 h. The reaction mixture was concentrated in vacuum and then purified by reverse phase chromatography to afford 2-chloro-3,6-difluoro-N-(4-(2-oxo-1,2-dihydropyridin-4-yl)benzyl)benzamide.

MS found for $C_{19}H_{13}ClF_2N_2O_2$ as (M+H)⁺ 377.16 ¹H NMR (400 MHz, dmso-d₆): ¹H-NMR (DMSO) δ: 11.65 (s, 1H), 9.36 (t, J=6.0 Hz, 1H), 7.69 (d, J=8.4 Hz, 2H), 7.58-7.52 (m, 1H), 7.46-7.37 (m, 4H), 6.61 (s, 1H), 6.55-6.53 (m, 1H), 4.52 (d, J=5.6 Hz, 2H).

B. The Preparation of Additional Compounds of Formula (I) According to the Synthetic Route of Scheme IV The preparation of 2,6-dichloro-N-(3-methyl-4-(2-oxo-1,2-dihydropyridin-4-yl)benzyl)benzamide (8)

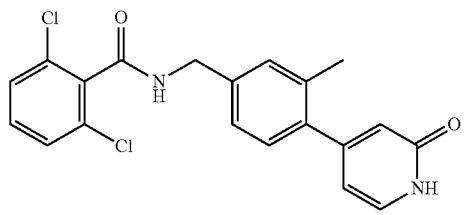 [SMILES: Cc1cc(CNC(=O)c2c(Cl)cccc2Cl)ccc1-c1cc[nH]c(=O)c1]

Step 1—The preparation of N-(4-bromo-3-methylbenzyl)-2,6-dichlorobenzamide

4-Bromo-3-methylphenyl)methanamine (0.1 g, 0.5 mmol), 2,6-dichlorobenzoic acid (0.11 g, 0.6 mmol), 2-(1H-7-azabenzotriazol-1-yl)-1,1,3,3-tetramethyl uronium hexafluorophosphate methanaminium (HATU) (0.23 g, 0.6 mmol), and N,N-Diisopropylethylamine (0.2 mL, 1.25 mmol) were combined in DMF (3 mL) and then stirred at room temperature until reaction was completed. Compound was precipitated by the addition of water and aqueous saturated solution of sodium bicarbonate. The precipitates were collected by filtration and then re-suspended in hot acetonitrile. When the solution was cooled down the solids were collected by filtration to have the pure compound N-(4-bromo-3-methylbenzyl)-2,6-dichlorobenzamide that was used for next step without further purification.

Step 2—The preparation of 2,6-dichloro-N-(3-methyl-4-(2-oxo-1,2-dihydropyridin-4-yl)benzyl) benzamide N-(4-Bromo-3-methylbenzyl)-2,6-dichlorobenzamide (0.13 g, 0.35 mmol), 2-oxo-1,2-dihydropyridin-4-ylboronic acid (0.053 g, 0.39 mmol), cesium carbonate (0.34 g, 1.05 mmol), [1,1' Bis(diphenylphosphino(ferrocene]dichloropalladium(II) (25 mg, 0.035 mmol) were dissolved in degassed DMF (3 mL) and H₂O (1.5 mL). The reaction mixture was degassed again by bubbling nitrogen through for 15 min then heated in the microwave at 85° C. for 20 min. The reaction mixture was diluted with EtOAc and extracted three times with water. The organic phase was dried over magnesium sulfate, filtered and concentrated in vacuum. The resulting solid was purified by reverse phase chromatography to afford 2,6-dichloro-N-(3-methyl-4-(2-oxo-1,2-dihydropyridin-4-yl)benzyl)benzamide.

MS found for $C_{20}H_{16}Cl_2N_2O_2$ as (M+H)⁺ 389.13 ¹H NMR (400 MHz, dmso-d₆): ¹H-NMR (DMSO) δ: 11.62 (s, 1H), 9.18 (t, J=6.4 Hz, 1H), 7.51-4.49 (m, 2H), 7.44-7.37 (m, 2H), 7.3 (s, 2H), 7.26 (d, J=7.6 Hz, 1H), 7.17 (d, J=7.6 Hz, 1H), 6.18 (s, 1H), 6.15-6.13 (m, 1H), 4.46 (d, J=6.0 Hz, 1H), 2.24 (s, 3H).

The preparation of 2,6-dichloro-N-(4-(1-methyl-2-oxo-1,2-dihydropyridin-4-yl)benzyl)benzamide (9)

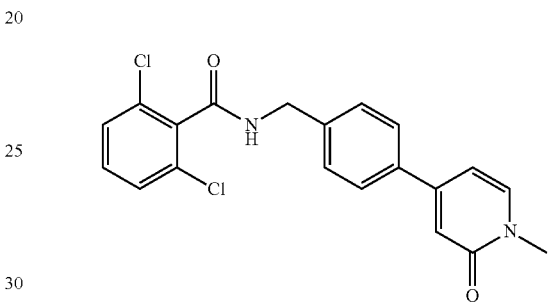

Compound (9) was prepared using a similar procedure as that described for Compound (8) with the appropriate starting materials. MS found for $C_{20}H_{16}Cl_2N_2O_2$: 387 (MH⁺); ¹H NMR (DMSO-d₆): δ 9.21 (t, J=6.0 Hz, 1H), δ 7.74 (d, J=7.2 Hz, 1H), δ 7.69 (d, J=8.4 Hz, 2H), δ 7.46 (m, 5H), δ 6.66 (d, J=2.0 Hz, 1H), δ 6.56 (dd, J=6.8 Hz, J'=2.0 Hz, 1H), δ 4.50 (d, J=5.6 Hz, 2H), δ 3.43 (s, 3H).

The preparation of 2,6-difluoro-N-(4-(2-oxo-1,2-dihydropyridin-4-yl)benzyl)benzamide (10)

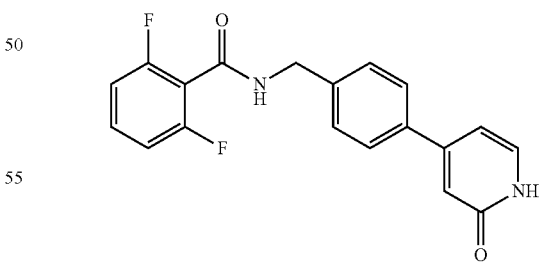

Compound (10) was prepared using a similar procedure as that described for Compound (8) with the appropriate starting materials. MS found for $C_{19}H_{14}F_2N_2O_2$: 341 (MH⁺); ¹H NMR (DMSO-d₆): δ 11.56 (s, 1H), δ 9.29 (t, J=6.0 Hz, 1H), δ 7.68 (d, J=8.0 Hz, 2H), δ 7.51 (m, 1H), δ 7.42 (m, 3H), δ 7.17 (m, 2H), δ 6.57 (d, J=1.2 Hz, 1H), δ 6.49 (dd, J=6.8 Hz, J'=1.6 Hz, 1H), δ 4.50 (d, J=6.0 Hz, 2H).

The preparation of 2-chloro-6-fluoro-N-(4-(2-oxo-1,2-dihydropyridin-4-yl)benzyl)benzamide (11)

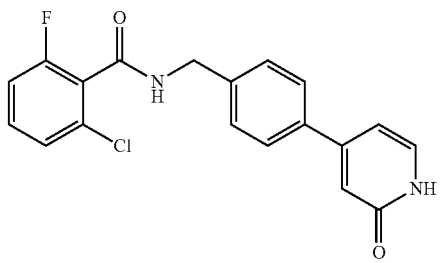

Compound (11) was prepared using a similar procedure as that described for Compound (8) with the appropriate starting materials. MS found for $C_{19}H_{14}ClFN_2O_2$: 357 (MH$^+$); $^1$H NMR (DMSO-d$_6$): δ 11.56 (s, 1H), δ 9.29 (t, J=4.8 Hz, 1H), δ 7.70 (d, J=7.6 Hz, 2H), δ 7.41 (m, 6H), δ 6.59 (s, 1H), δ 6.52 (d, J=6.4 Hz, 1H), δ 4.53 (d, J=5.6 Hz, 2H).

The preparation of 2,6-dichloro-N-(2-fluoro-4-(2-oxo-1,2-dihydropyridin-4-yl)benzyl)benzamide (12)

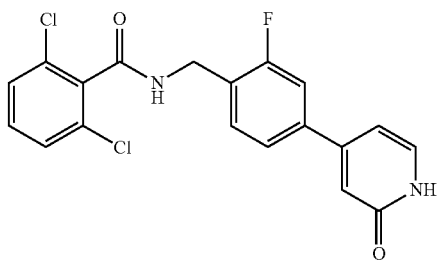 [SMILES: O=C(NCc1ccc(-c2cc[nH]c(=O)c2)cc1F)c1c(Cl)cccc1Cl]

Compound (12) was prepared using a similar procedure as that described for Compound (8) with the appropriate starting materials. MS found for $C_{19}H_{13}Cl_2FN_2O_2$: 391 (MH$^+$); $^1$H NMR (DMSO-d$_6$): δ 11.62 (s, 1H), δ 9.23 (t, J=5.6 Hz, 1H), δ 7.57 (m, 3H), δ 7.50 (m, 2H), δ 7.43 (m, 2H), δ 6.63 (d, J=1.2 Hz, 1H), δ 6.52 (dd, J=6.8 Hz, J'=1.6 Hz, 1H), δ 4.51 (d, J=6.0 Hz, 2H).

The preparation of 2,6-dichloro-N-(4-(5-fluoro-2-oxo-1,2-dihydropyridin-4-yl)benzyl)benzamide (13)

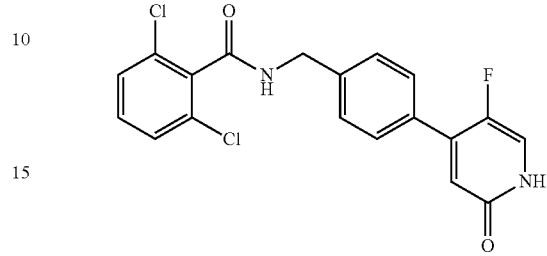

Compound (13) was prepared using a similar procedure as that described for Compound (8) with the appropriate starting materials. MS found for $C_{19}H_{13}Cl_2FN_2O_2$: 391 (MH$^+$); $^1$H NMR (DMSO-d$_6$): δ 11.27 (s, 1H), δ 9.23 (t, J=6.0 Hz, 1H), δ 7.80 (d, J=4.0 Hz, 1H), δ 7.50 (m, 7H), δ 6.53 (d, J=6.4 Hz, 1H), δ 4.52 (d, J=6.0 Hz, 2H).

Example 5

The preparation of phosphoric acid mono-(4-{4-[(2,6-dichloro-benzoylamino)-methyl]-phenyl}-2-oxo-2H-pyridin-1-ylmethyl) ester (14) according to the synthetic route of Scheme V

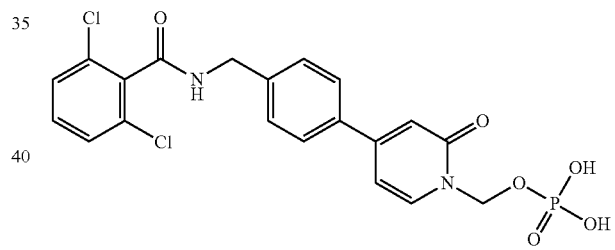

Scheme XI

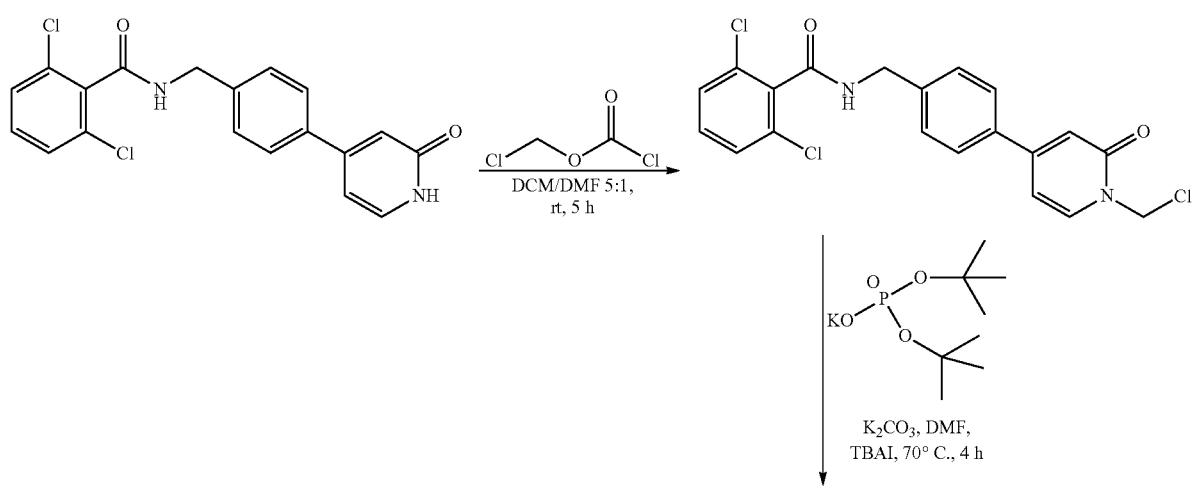

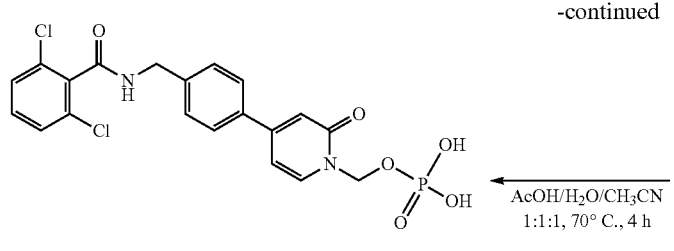 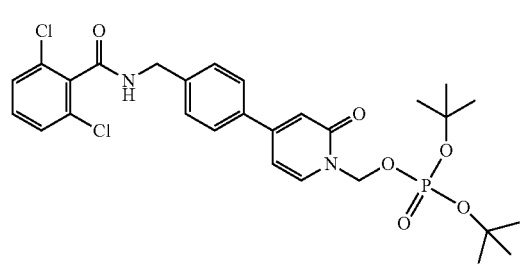

AcOH/H₂O/CH₃CN
1:1:1, 70° C., 4 h

Step 1—The preparation of 2,6-dichloro-N-[4-(1-chloromethyl-2-oxo-1,2-dihydro-pyridin-4-yl)-benzyl]-benzamide 2,6-Dichloro-N-[4-(2-oxo-1,2-dihydro-pyridin-4-yl)-benzyl]-benzamide (1.62 g, 4.34 mmol) was suspended in 15 mL dichloromethone. Chloromethylchloroformate (0.672 g, 5.21 mmol) was added followed by 3 mL DMF. The mixture was stirred at room temperature for five hours. After diluting with 200 mL ethyl acetate, the organic phase was washed with saturated, aqueous sodium bicarbonate solution and brine, dried with magnesium sulfate and evaporated under vacuum. The crude 2,6-dichloro-N-[4-(1-chloromethyl-2-oxo-1,2-dihydro-pyridin-4-yl)-benzyl]-benzamide was used in the following step without further purification.

Step 2—The preparation of phosphoric acid di-tert-butyl ester 4-{4-[(2,6-dichloro-benzoylamino)-methyl]-phenyl}-2-oxo-2H-pyridin-1-ylmethyl ester 2,6-Dichloro-N-[4-(1-chloromethyl-2-oxo-1,2-dihydro-pyridin-4-yl)-benzyl]-benzamide from the previous step was dissolved in 50 mL DMF. Potassium carbonate (1 g) was added followed by potassium di(t-butyl)phosphate (2 g) and tetrabutylammonium iodide (50 mg). The mixture was stirred at 70° C. for four hours after which it was poured into 300 mL ethyl acetate. The organic phase was washed with water and brine, dried with magnesium sulfate and evaporated under vacuum. The crude product was further purified by silica gel chromatography (eluent: ethyl acetate), giving phosphoric acid di-tert-butyl ester 4-{4-[(2,6-dichloro-benzoylamino)-methyl]-phenyl}-2-oxo-2H-pyridin-1-ylmethyl ester as a colorless oil which slowly crystallized.

Step 3—The preparation of phosphoric acid mono-(4-{4-[(2,6-dichloro-benzoylamino)-methyl]-phenyl}-2-oxo-2H-pyridin-1-ylmethyl) ester Phosphoric acid di-tert-butyl ester 4-{4-[(2,6-dichloro-benzoylamino)-methyl]-phenyl}-2-oxo-2H-pyridin-1-ylmethyl ester from the previous step was dissolved in 20 mL acetonitrile, 20 mL acetic acid and 20 mL water, and heated at 70° C. for four hours. All volatile components were evaporated under vacuum and the residue was dissolved in 10 mL DMF. Slow addition of acetonitrile (~60 mL) precipitated the product which was filtered, washed with more acetonitrile and dried, giving phosphoric acid mono-(4-{4-[(2,6-dichloro-benzoylamino)-methyl]-phenyl}-2-oxo-2H-pyridin-1-ylmethyl) ester (1.17 g, 56% over three steps) as a white powder.
¹H-NMR (DMSO) δ: 9.23 (t, J=6.2 Hz, 1H), 7.73 (d, J=8.4 Hz, 2H), 7.71 (d, J=8.4 Hz, 1H), 7.52-7.40 (m, 5H), 6.72 (d, J=1.6 Hz, 1H), 6.65 (dd, J=7.2 Hz, J=1.6 Hz, 1H), 5.61 (d, J=9.6 Hz, 2H), 4.52 (d, J=6.4 Hz, 2H). MS: 483/485 (MH⁺).

Example 6

2,6-dimethyl-N-(4-(2-oxopiperidin-4-yl)benzyl)benzamide

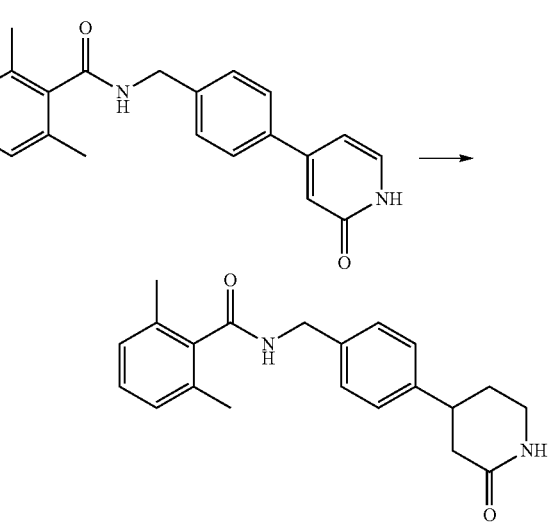

To a solution of 2,6-dimethyl-N-(4-(2-oxo-1,2-dihydro-pyridin-4-yl)benzyl)benzamide (see compound 5 of example 3B) in ethanol/methanol (5:1), 10% Pd/C was added and the mixture was hydrogenated (1 atm) at 23° C. for 12 hours. The catalyst was filtered through celite pad and washed with methanol Filtrate and washings were combined and the solvent was then concentrated and chromatographed (SiO2, 3-15% EtOAc/MeOH) to provide the title compound. MS found for $C_{21}H_{24}N_2O_2$ as (M+H)⁺ 337.1 ¹H NMR (400 MHz, dmso-d₆): δ: 8.76 (t, J=5.6 Hz, 1H); 7.52 (brs, 1H), 7.27-7.14 (m, 4H); 7.13-6.99 (m, 3H); 4.40 (d, J=6.4 Hz, 2H); 3.23-3.16 (m, 2H); 3003-2.98 (m, 1H); 2.35-2.21 (m 2H); 2.17 (s, 6H); 1.88-1.78 (m, 2H).

Example 7

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules.

Example 8

A tablet of a compound of Formula (I) is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

Example 9

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

Example 10

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch, and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Example 11

Suppositories, each containing 25 mg of active ingredient, are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Example 12

Suspensions, each containing 50 mg of active ingredient per 5.0 mL dose, are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Example 13

A subcutaneous formulation may be prepared as follows:

| Ingredient | Quantity |
| --- | --- |
| Active Ingredient | 5.0 mg |
| Corn Oil | 1.0 mL |

Example 14

An injectable preparation is prepared having the following composition:

| Ingredients | Amount |
| --- | --- |
| Active ingredient | 2.0 mg/mL |
| Mannitol, USP | 50 mg/mL |
| Gluconic acid, USP | q.s. (pH 5-6) |
| water (distilled, sterile) | q.s. to 1.0 mL |
| Nitrogen Gas, NF | q.s. |

Example 15

A topical preparation is prepared having the following composition:

| Ingredients | grams |
| --- | --- |
| Active ingredient | 0.01-1 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

Example 16

Sustained Release Composition

| Ingredient | Weight Range (%) | Range 1 (%) | Range 2 (%) |
| --- | --- | --- | --- |
| Active ingredient | 50-95 | 70-90 | 75 |
| Microcrystalline cellulose (filler) | 1-35 | 5-15 | 10.6 |
| Methacrylic acid copolymer | 1-35 | 5-12.5 | 10.0 |
| Sodium hydroxide | 0.1-1.0 | 0.2-0.6 | 0.4 |
| Hydroxypropyl methylcellulose | 0.5-5.0 | 1-3 | 2.0 |
| Magnesium stearate | 0.5-5.0 | 1-3 | 2.0 |

The sustained release formulations are prepared as follows: compound and pH-dependent binder and any optional excipients are intimately mixed (dry-blended). The dry-blended mixture is then granulated in the presence of an aqueous solution of a strong base which is sprayed into the blended powder. The granulate is dried, screened, mixed with optional lubricants (such as talc or magnesium stearate), and compressed into tablets. Certain aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl, methylcellulose, cationic methacrylate copolymers (dimethylaminoethyl methacrylate/methyl-butyl methacrylate copolymers—Eudragit® E—Röhm Pharma) and the like. These film-forming agents may optionally contain colorants, plasticizers, and other supplemental ingredients.

The compressed tablets preferably have a hardness sufficient to withstand 8 Kp compression. The tablet size will depend primarily upon the amount of compound in the tablet. The tablets will include from 300 to 1100 mg of compound free base. Preferably, the tablets will include amounts of compound free base ranging from about 10-200 mg, 100-300 mg, or 400-600 mg.

In order to influence the dissolution rate, the time during which the compound containing powder is wet mixed is controlled. Preferably the total powder mix time, i.e., the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

Example 17

ALDH2 Assays

Standard ALDH2 reaction mixtures contained 150 uM formaldehyde, 2.5 mM NAD$^+$, 10 mM MgCl2 and 10 nM recombinant human ALDH2 in 50 mM Hepes buffer, pH 7.4, 0.01% Tween 20 in a final volume of 50 ul using 384-well plates. After 60 min of pre-incubation of compound with ALDH2 and formaldehyde, the reaction was started by adding NAD+ and the reaction mixture was allowed to proceed for 90 minutes. Activity of the enzyme was determined by monitoring NADH formation using Perkin-Elmer Envision Reader with excitation and emission wavelengths set at 340 and 460 nm, respectively.

MAO-A and MAO-B Assays

MAO assays included luminogenic MAO substrate, reaction buffers, Luciferin Detection and the reconstitution buffer with esterase. Standard MAO reaction mixtures included microsome contained MAO-A (2 ug) or MAO-B (10 ug), 160 uM substrate for MAO-A or 16 uM substrate for MAO-B, MAO-A buffer (100 mM Hepes buffer, pH 7.5, 5% glycerol) or MAO-B buffer (100 mM Hepes, pH 7.5, 5% glycerol, 10% dimethyl sulfoxide) in a final volume of 30 ul. After 20 minutes of pre-incubation of the enzyme with compounds, the reaction was initiated by adding enzyme substrate and the reaction was allowed to proceed for 60 minutes. Reconstituted Luciferin Detection Reagent (30 ul) was then added is added to simultaneously stop the MAO reaction and convert the methyl ester derivative to luciferin and produce light. The amount of light produced is directly proportional to the activity of MAO. The mixtures were further incubated for 20 minutes and activity of the enzyme was determined using Perkin-Elmer Envision Reader.

Note:

IC50 refers to the concentration of a compound that inhibits a reaction by 50%. In the case of competitive inhibition, IC50=2Ki when the substrate is present at the Km concentration, as per the relationship:

$$Ki=IC50/[1+(\text{substrate concentration}/Km)].$$

Representative data for several compounds are presented in Table 1 below.

TABLE 1

| | | ALDH-2 AND MAO INHIBITION | | |
| --- | --- | --- | --- | --- |
| NUMBER | COMPOUND | $IC_{50}$ HALDH2 NM | $IC_{50}$ HMAO-A μM | $IC_{50}$ HMAO-B μM |
| 1 | 2,6-dichloro-4-(2-methoxyethoxy)-N-(4-(2-oxo-1,2-dihydropyridin-4-yl)benzyl)benzamide | 63 | >130 | >130 |
| 2 | 2,6-dichloro-N-[4-(2-oxo-1,2-dihydro-pyridin-4-yl)-benzyl]-benzamide | 102 | >130 | >130 |

TABLE 1-continued

ALDH-2 AND MAO INHIBITION

| NUMBER | COMPOUND | IC$_{50}$ HALDH2 NM | IC$_{50}$ HMAO-A μM | IC$_{50}$ HMAO-B μM |
|---|---|---|---|---|
| 3 | 2-chloro-3-fluoro-N-(4-(2-oxo-1,2-dihydropyridin-4-yl)benzyl)benzamide | 215 | >130 | >130 |
| 4 | 2-chloro-6-methyl-N-(4-(2-oxo-1,2-dihydropyridin-4-yl)benzyl)benzamide | 23 | >130 | >130 |
| 5 | 2,6-dimethyl-N-(4-(2-oxo-1,2-dihydropyridin-4-yl)benzyl)benzamide | 166 | >130 | >130 |
| 6 | 2,6-dichloro-N-[4-(6-methyl-2-oxo-1,2-dihydro-pyridin-4-yl)-benzyl]-benzamide | 1113 | >130 | >130 |
| 7 | 2-chloro-3,6-difluoro-N-(4-(2-oxo-1,2-dihydropyridin-4-yl)benzyl)benzamide | 464 | >130 | >130 |
| 8 | 2,6-dichloro-N-(3-methyl-4-(2-oxo-1,2-dihydropyridin-4-yl)benzyl)benzamide | 480 | >130 | >130 |
| 9 | 2,6-dichloro-N-(4-(1-methyl-2-oxo-1,2-dihydropyridin-4-yl)benzyl)benzamide | 2093 | >130 | >130 |
| 10 | 2,6-difluoro-N-(4-(2-oxo-1,2-dihydropyridin-4-yl)benzyl)benzamide | 890 | >130 | >130 |
| 11 | 2-chloro-6-fluoro-N-(4-(2-oxo-1,2-dihydropyridin-4-yl)benzyl)benzamide | 379 | >130 | >130 |
| 12 | 2,6-dichloro-N-(2-fluoro-4-(2-oxo-1,2-dihydropyridin-4-yl)benzyl)benzamide | 304 | >130 | >130 |
| 13 | 2,6-dichloro-N-(4-(5-fluoro-2-oxo-1,2-dihydropyridin-4-yl)benzyl)benzamide | 25 | >130 | >130 |
| 14 | phosphoric acid mono-(4-{4-[(2,6-dichloro-benzoylamino)-methyl]-phenyl}-2-oxo-2H-pyridin-1-ylmethyl) ester | >10000.00 | >129.51 | >130 |

The above data suggests that compounds of the invention generally inhibit the ALDH2 enzyme with an IC$_{50}$ of less than 1 uM.

Example 18

Reduction of Alcohol Dependency

Animals: The strains of alcohol-preferring rats are housed individually in stainless-steel wire mesh cages (26' 34' 20 cm) under constant temperature of 21±1° C. and reversed 12 hour light-12 hour dark cycle (10:00-22:00 dark). These rats consume significantly more alcohol than their respective control strains: the selectively-bred alcohol non-preferring (NP), the low alcohol-drinking (LAD) rat, and the Wistar rat. The FH and P rats are derived from the Wistar rat. Water and food (Agway Prolab Rat/Mouse/Hamster 3000 formula, Agway, Syracuse, USA) are provided ad lib.

Establishment of Baseline: Following the standard method (Murphy et al., 1988; Rezvani and Grady, 1994; Rezvani et al., 1995), alcohol-preferring rats are given 1 day access to water in a Richter tube followed by 3 days of free access to a solution of 10% (v/v) ethanol given as the only source of fluid. Thereafter, the rats are given a choice between alcohol and water for the remainder of the study. All experiments involve 24 hour free access to food, water, and alcohol in a two-bottle choice paradigm.

Experimental Protocol: After establishment of a stable baseline for alcohol and water intakes, animals are maintained on a continuous access to alcohol and water via a two-bottle choice paradigm for about 2 months. Then, rats receive a single i.p. injection of the saline vehicle, or a test compound at 09:30 am. Alcohol and water intakes are measured at 6 and 24 hours after the injection. Food intake is measured 24 hours after the injection.

Chronic Systemic Administration: A chronic experiment is conducted with adult male P rats. After establishment of stable baselines for alcohol and water intakes, and following a cross-over design, the test drug or vehicle is given i.p. once a day for 10 consecutive days. Alcohol and water intakes are measured at 6 and 24 hours after the treatment, whereas food intake is measured 24 hours after the treatment. Each rat receives both treatments, and a washout period of 3 days is imposed between treatments.

Statistical Analysis: The results are expressed as means±standard error of means (SEM). Alcohol intake (g/kg) is calculated by multiplying the volume of alcohol consumed by 10% and 0.7893 (ethanol density)/animal body weight in kg. Alcohol preference, expressed as a percentage, is calculated as follows: (volume of alcohol consumed in mL/total fluid intake in mL)×100 (Rezvani et al., 1990; Rezvani and Grady, 1994). Statistical differences between different groups are determined using analysis of variance followed by Newman-Keuls protected t-test.

Rat Alcohol Self Administration

Alcohol-preferring (iP) male rats were trained to daily (Monday to Friday) self-administer alcohol (10% v/v) under operant conditions. A fixed-ratio of 3 (FR3), where rats had to press a lever 3 times to get one drop of alcohol during 20-min sessions was used (Cowen et al, 2005a; Cowen et al., 2005b; Lawrence et al., 2006). Availability of alcohol was conditioned by the presence of an olfactory cue (2 drops of vanilla essence, placed on the bedding of the operant chamber directly under the active lever), plus a 1-sec light stimulus when FR3 was obtained. For each session, total alcohol and water responses were recorded. Following acquisition of lever pressing behavior and stable alcohol self-administration, rats were administered oral vehicle or compound of Example 5 (5, 10 and 30 mg-eq/kg) 1 hr before each session in a counterbalanced order. Every rat received all drug doses and vehicle once per week in a randomly assigned order. Compound of Example 5 at 10 and 30 mg-eq/kg significantly decreased the number of lever presses for alcohol (FIG. 1).

Example 19

Reduction of Cocaine Dependency and Relapse

Intravenous cocaine (0.35 mg/kg/inj) is used in an operant self administration and reinstatement model in rats. In this model, rats addicted to cocaine repeatedly press a lever to obtain an intravenous dose (iv) of cocaine. When cocaine is removed, rats stop pressing the lever. However, rats resume lever pressing for cocaine (reinstatement) if subjected to a small intraperitoneal (ip) dose (10 mg/kg) of cocaine that normally has no effect in naïve animals. This is a valid animal model of relapse in cocaine addicted humans, and tests the ability of the compounds of Formula (I) to block cocaine craving and relapse.

Male Sprague-Dawley rats with jugular vein catheterization are used. Rats are presented with a choice of two levers in the test/training chamber. Depression of the active lever results in delivery of a cocaine reinforcer, while depression of the inactive lever does not result in reinforcement. During the initial 15 hour fixed ratio (FR) 1 training session (FR1 stands for one lever press equals one reinforcement delivery), a food pellet is taped to the active lever to facilitate lever pressing, and each active lever press results in the delivery of a single 45 mg food pellet (Noyes, Lancaster, N.H.). The following day the reinforcer is switched to FR1 lever pressing for cocaine (0.35 mg/kg/inj, delivered in 0.27 sec). Cocaine reinforcement is delivered on a modified FR1 schedule such that each drug infusion is accompanied by illumination of a stimulus over the active lever and a 20 second timeout during which active lever presses are counted but do not result in reinforcer delivery. After 20 seconds the stimulus light is turned off and the first lever press again results in drug delivery. Depression of the inactive lever does not have any consequence. Daily training sessions for each group lasts 2 hours, or until a subject earns 200 drug infusions, whichever comes first. The subjects remain in drug self-administration training mode until acquisition criterion is met (average presses on the active lever varied by <10% over 3 consecutive training days). This typically takes 10-14 days.

Extinction and Reinstatement

For extinction and reinstatement experiments, rats are required to display stable responding (variability not higher than 15% in 2 consecutive sessions) on the FR1 schedule of reinforcement. After achieving these criteria, extinction procedures begin such that lever presses no longer result in delivery of the reinforcer. When average responding across three consecutive extinction sessions falls to 15% of responding during maintenance, subjects are tested for reinstatement. In cocaine-experienced animals, reinstatement is primed with a non-contingent injection of cocaine (10 mg/kg ip) immediately before the reinstatement session. In order to increase statistical power and therefore decrease animal usage, a second extinction period is initiated 3-4 days after the first, which allows for additional within-subjects comparisons. Experiments use a between-session-training and testing method in which animals are trained to self administer drug. Their behavior is then extinguished and then reinstatement is primed on different days.

Results: Effect of Compounds of Formula (I) on Cocaine Induced Relapse

Ip injections of the compounds of Formula (I) dose dependently block relapse for cocaine. Animals are trained to self administer cocaine (0.35 mg/kg/inj) until they reach stable responding. They are then trained in the same chambers but cocaine is no longer available. Once they drop their lever presses responding to a minimal level (extinction), they are then given a priming dose of cocaine (10 mg/kg) and consequently their responding lever presses significantly increase (relapse). Those same animals receiving effective compounds of Formula (I) prior to the priming injection of cocaine do not show an increase in their lever presses responding (did not relapse).

Rat Cocaine Cue Reinstatement

Figure 2:
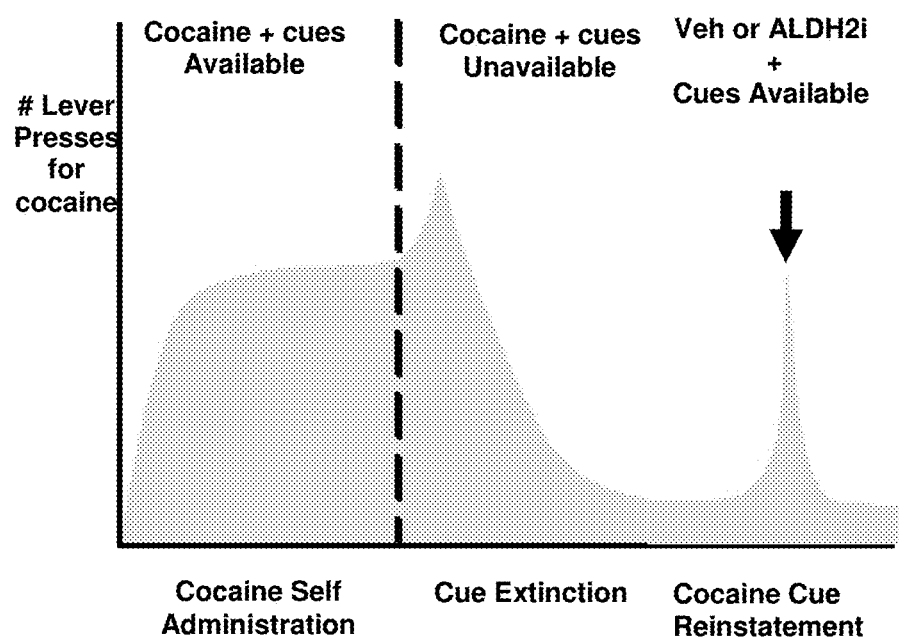
FIG. 2 is a graphical representation of cocaine cue replacement study design.

Training of male Sprague Dawley (SD) rats had 3 separate stages. First, during self administration, animals were trained to lever press for cocaine with presentation of concomitant cues associated with drug delivery. Rats that reached criteria for addiction were included in the study. Afterward, during cue extinction, cocaine-cue dependent behavior was extinguished. Lastly, during cocaine cue reinstatement, the effect of compounds was tested on lever presses upon cue presentation (FIG. 2).

Cocaine Self Administration

Rats were trained to self administer i.v. cocaine (0.35 mg/kg/injection) daily (Monday to Friday) in standard operant chambers with retractable levers (Coulbourn Instruments, PA). During the daily 2 hr session, rats received a 0.05 ml infusion of 0.35 mg/kg cocaine every time the active lever was pressed. A cue light and tone turned on for 2 sec together with activation of a pump that delivered the cocaine solution. Rats were required to maintain an infusion rate of ≥20+ per day for at least 10 days before being moved to extinction training. Rats that did not reach this criterion were excluded from the study.

Cue Extinction

During extinction sessions lever presses no longer produced cocaine infusion and cue light/tone presentation was absent. Rats received a maximum of 15 extinction sessions. Rats were considered to have extinguished behavior when during 2 consecutive sessions they exhibited an average of <15 active lever presses or 30% of the number of responses per session that occurred during the last 2 sessions of cocaine self-administration, whichever came first.

Cocaine Cue Reinstatement

On the next day after reaching extinction criteria, rats were treated orally with vehicle (Formulation 2B: 25% PEG400/5% Vit E TPGS/1% SLS/69% water with 0.5% Methocel) or drug (compound of Example 2 or compound of Example 5) before the cue reinstatement session. Cue reinstatement began with a tone and cue light. This 2 hr session was identical to the self-administration session (cue light and tone present upon active lever press) except that no cocaine was delivered. The number of active lever presses was compared to extinction lever responding. This is considered a measure of reinstatement. The next day, rats were returned to extinction sessions for at least 2 or 3 more sessions. Rats then received a second and last reinstatement session with an opposite treatment to the one received on the first reinstatement session (vehicle or drug treatment). When rats pretreated with vehicle are presented with cues associated with cocaine availability, they significantly increase their number of lever presses. The light/tone presentation triggers this response and it is interpreted as a measure of reinstatement even though cocaine is not available.

Figure 3:
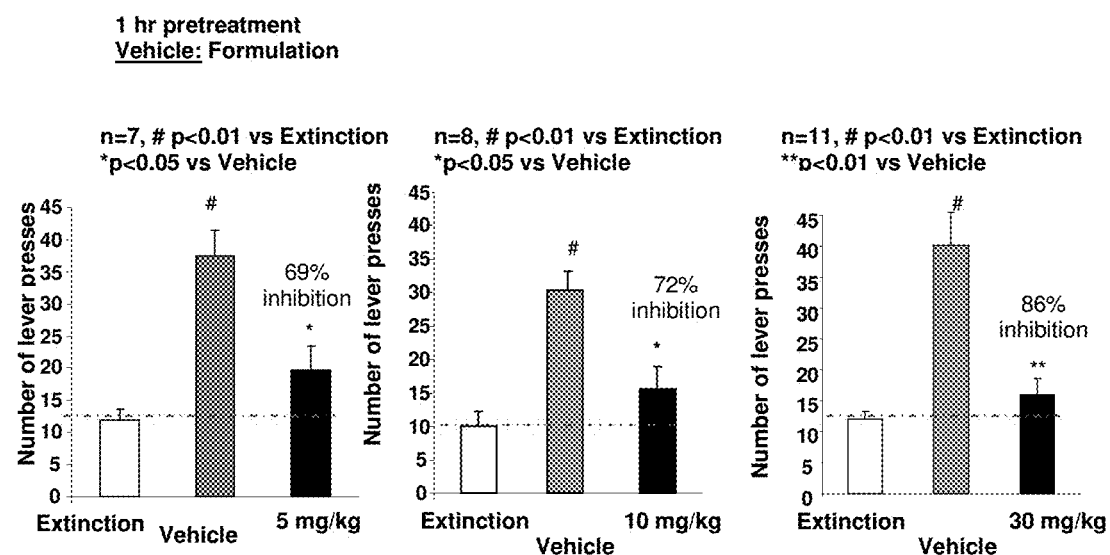
FIG. 3 shows significant inhibition of cocaine cue reinstatement in rats orally administered a compound of the invention compared to vehicle.

Compound of Example 2 significantly reduced cocaine cue-induced reinstatement in SD rats by 69%, 72% and 86% at 5, 10 and 30 mg/kg, respectively, when compared to vehicle (FIG. 3). An ANOVA revealed a significant effect of treatment on number of lever presses. A significant effect of treatment was observed for all doses tested (p<0.001). Fisher post-hoc comparisons showed that rats treated with vehicle prior to cue reinstatement session had a significant increase in number of lever presses when compared with extinction session (p<0.05). After treatment with compound of Example 2 (5, 10 or 30 mg/kg) prior to cue reinstatement session, rats significantly decreased lever presses responding compared with vehicle treatment (69% inhibition: p<0.05, 72% inhibition: p<0.05 and 86% inhibition: p<0.01, respectively). #p<0.01 compared with extinction; *p<0.05 and **p<0.01 compared with vehicle.

Figure 4:
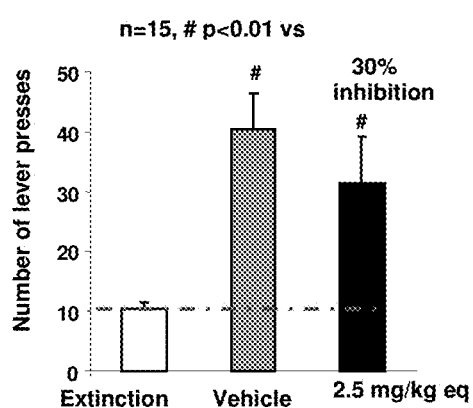
FIG. 4 shows significant inhibition of cocaine cue reinstatement in rats orally administered a compound of the invention compared to vehicle.
Figure 4:
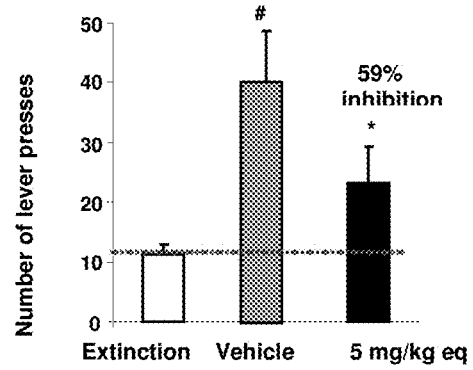
Figure 4:
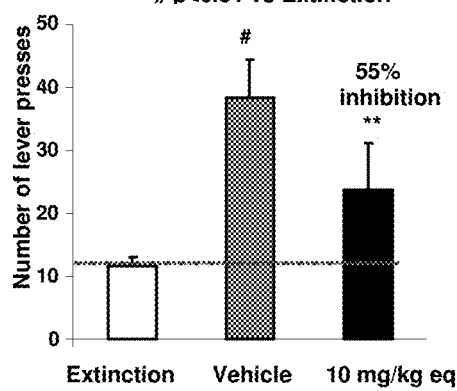
Figure 4:
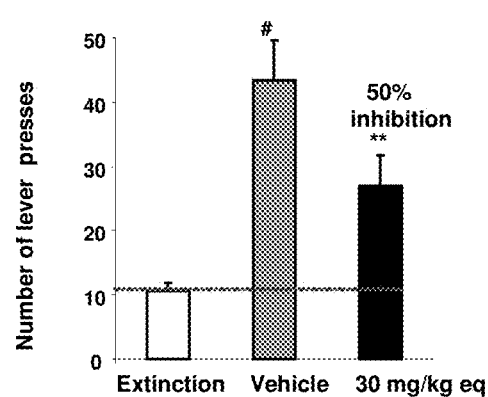

The prodrug compound of Example 5 was efficacious at 5, 10 and 30 mg-eq/kg in cocaine cue reinstatement with 59%, 55% and 50% inhibition, respectively (FIG. 4). At the lowest dose tested, 2.5 mg-eq/kg, the effect was not significantly different from vehicle.

Compound of Example 5 reduced cocaine cue-induced reinstatement in SD rats. The number of lever presses was recorded during the 2 hr cue-induced reinstatement session. An ANOVA revealed a significant effect of treatment on number of lever presses. Rats that had extinguished lever press responding were treated with oral vehicle and compound of Example 5 (2.5, 5, 10 or 30 mg-eq/kg) 1 hr before the cue-induced reinstatement session. A significant effect of treatment was observed for 2.5, 5, 10 and 30 mg-eq/kg doses tested (2.5 mg/kg eq: $F(2, 28)=9.39$, $p<0.01$, $n=15$; 5 mg/kg eq: $F(2, 14)=11.47$, $p<0.01$, $n=8$; 10 mg/kg eq: $F(2, 18)=13.901$, $p<0.001$, $n=10$; 30 mg/kg eq: $F(2, 22)=18.221$, $p<0.001$, $n=12$). Fisher post-hoc comparisons revealed that rats treated with vehicle prior to cue reinstatement session showed a significant increase in number of lever presses when compared with extinction session (p<0.01). After treatment with compound of Example 5 (5, 10 or 30 mg/kg) prior to cue reinstatement session, rats significantly decreased lever presses responding compared with vehicle treatment (59% inhibition: p<0.05, 55% inhibition: p<0.01 and 50% inhibition: p<0.01, respectively). Fisher post-hoc comparisons revealed that 2.5 mg/kg eq dose was not significantly different from vehicle (30% inhibition, p>0.05, N.S.). #p<0.01 compared with extinction; *p<0.05 and **p<0.01 compared with vehicle).

Example 20

Reduction of Nicotine Dependency

Biological Material: Wistar-derived male rats (250-300 g) are housed in groups of two and maintained in a temperature-controlled environment on a 12 hour:12 hour light cycle (0600 h on-1800 h off), upon arrival in the laboratory. Animals are given free access to food and water during a one-week habituation period to the laboratory. Animals used in the research studies are handled, housed, and sacrificed in accord with the current NIH guidelines regarding the use and care of laboratory animals, and all applicable local, state, and federal regulations and guidelines. Animals are handled daily for several days to desensitize them to handling stress before experimental testing. Sample sizes (e.g., n=8) are sufficient to provide reliable estimates of drug effects.

Drug Treatments: The Wistar-derived rats receive several doses of the compounds of Formula (I) administered intraperitonealy (i.p.), and a positive control compound, mecamylamine (1.5 mg/kg, subcutaneously (s.c.). The compounds are administered 30 minutes prior to SA sessions. The compounds of Formula (I) are administered at 2 mL/kg for the 7.5 mg/kg (3.75 mg/mL) and 10 mg/kg (5 mg/mL), doses, and at 3 mL/kg for the 15 mg/kg dose (5 mg/mL). The compound is dissolved in corn oil (VEH), and sonicated for at least 30-minutes, up to 2 hours prior to administration. Mecamylamine is dissolved in 0.09% isotonic saline and administered at a volume of 1 mL/kg.

Apparatus: Food training and nicotine self-administration takes place in 8 standard Coulbourn operant chambers. Each chamber is housed in a sound-attenuated box. Operant chambers are equipped with two levers; mounted 2 cm above the floor, and a cue light mounted 2 cm above the right lever on the back wall of the chamber. For food training, a food hopper is located 2-cm to the left/right of either lever, in the middle of the back wall. Intravenous infusions are delivered in a volume of 0.1 mL over a 1 second interval via an infusion pump (Razel, Conn.) housed outside of the sound attenuated chamber.

Food Training: Lever pressing is established as demonstrated by the method of Hyytia et al., (1996). Initially, rats are restricted to 15 grams of food daily (approximately 85% of their free-feeding body weight). After the second day of food restriction, rats are trained to respond for food under a fixed-ratio 1 (FR1) schedule of reinforcement (1 food pellet for each lever press) with a 1 second time-out (TO-1 s) after each reinforcement. Training sessions are given twice per day, and TO periods are gradually increased to 20 seconds. Once rats obtain a steady baseline responding at a FR1-TO20 s schedule of reinforcement, they are returned to ad libitum food prior to preparation for intravenous jugular catheter implant surgery.

Surgery: Rats are anesthetized with a ketamine/xylazine mixture and chronic silastic jugular catheters are inserted into the external jugular vein and passed subcutaneously to a polyethylene assembly mounted on the animal's back. The catheter assembly consists of a 13-cm length of silasitic tubing (inside diameter 0.31 mm; outside diameter 0.64 mm), attached to a guide cannula that is bent at a right angle. The cannula is embedded into a dental cement base and anchored with a 2×2 cm square of durable mesh. The catheter is passed subcutaneously from the rats back to the jugular vein where it is inserted and secured with a nonabsorbable silk suture. Upon successful completion of surgery, rats are given 3-5 days to recover before self-administration sessions are started. During the recovery period, rats remain ad libitum food access, and have catheter lines flushed daily with 30 units/mL of heparinized saline containing 66 mg/mL of Timentin to prevent blood coagulation and infection in the catheters.

Nicotine Self-Administration: Following successful recovery from catheter implant surgery, rats are again food deprived to 85% of their free-feeding body weight. Once self-administration sessions begin, subjects are trained to IV self-administer nicotine in 1-hour baseline sessions, 5 days per week, under a FR1-TO-20 schedule of reinforcement until stable responding is achieved. Stable responding is defined as less than 20% variability across 3 consecutive sessions. After acquisition of stable responding for nicotine, various doses of the compounds of Formula (I) are tested using a within-subjects Latin square design. Rats are allowed to self-administer nicotine after treatment with each dose of the compounds of Formula (I) for 1 test session, and subsequently "rebaselined" for 1-3 days before the next dose probe during one test self-administrations sessions. Following the testing of the first compound, rats receive the positive control compound, mecamylamine (1.5 mg/kg), administered according to a crossover design.

During SA sessions, rats are flushed with saline before test session to ensure catheter patency, and again flushed after test sessions with 30 units/mL of heparinized saline containing 66 mg/mL of Timentin, to prevent blood coagulation and infection in the catheters. If catheter patency is in question, as demonstrated by an unexpected shift in response rates, or inability to draw blood from the catheter, 0.1 mL of a short-acting anesthetic (Brevital) is infused. Animals with patent catheters exhibit rapid loss of muscle tone within 3-seconds. Rats with catheters no longer patent according to the Brevital test are removed from the experiment.

Data Analysis: Data is collected on-line from multiple operant chambers, and reported as mean cumulative number of bar presses for nicotine. The data is analyzed using the StatView statistical package on a PC-compatible computer.

Results: The Effect of Compounds on Nicotine Self Administration:

Increasing doses of the compounds of Formula (I) administered as described in the above protocol reduce the number of bar presses (plotted as the number of infusions) for nicotine administration.

Rat Nicotine Self Administration

Acute Treatment

Figure 5:
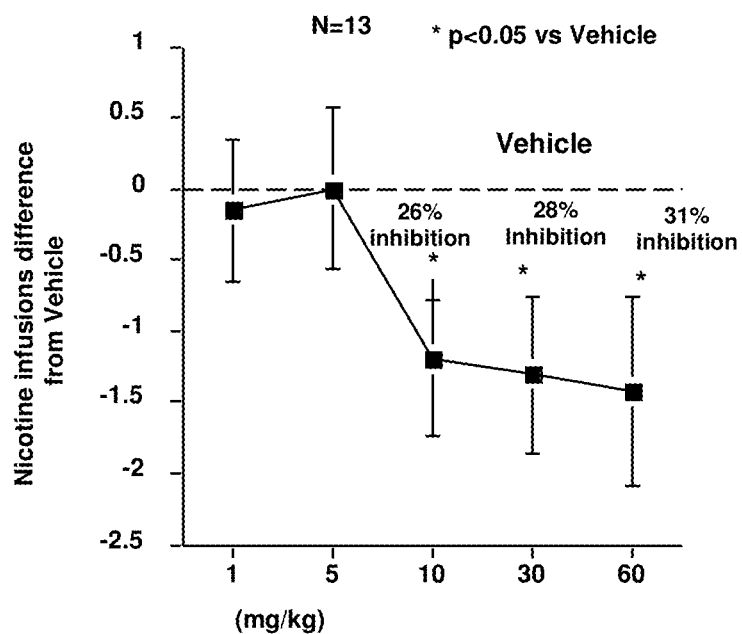
FIG. 5 shows significantly reduced nicotine self administration in rats orally administered a compound of the invention compared to vehicle.
Figure 6:
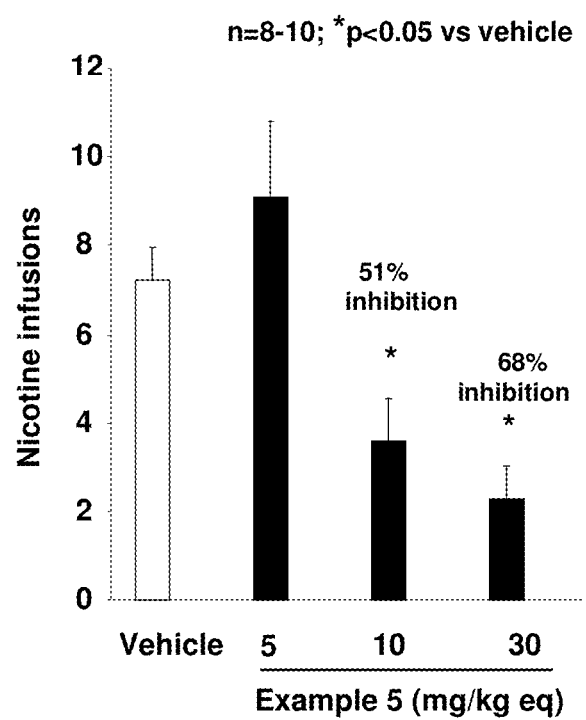
FIG. 6 shows significantly reduced nicotine self administration in rats orally administered a compound of the invention compared to vehicle.

Male SD rats were trained to self administer i.v. nicotine (0.03 mg/kg/inj) daily (Monday to Friday) in standard operant chambers with retractable levers (MED Associates, Inc) as previously published (Levin et al., 2003; Levin et al., 2007). During the daily 45 min session, rats received 0.05 ml infusion of 0.03 mg/kg/infusion of nicotine every time the active lever was pressed. A cue light and tone turned on for 0.5 sec together with the activation of a pump that delivered the nicotine solution. Daily sessions were run for at least 10 days before the initiation of drug testing. Solutions of compounds of Example 2 and Example 5 were prepared fresh daily in Formulation 2B: 25% PEG400/5% Vit E TPGS/1% SLS/69% water with 0.5% Methocel) for oral dosing. Compound of Example 2 doses were administered in a counterbalanced design for testing 1 hr before each nicotine session. Every rat received all drug doses and vehicle in a randomly assigned order. The oral drug administrations were made twice per week. Compound of Example 2 at 10, 30 and 60 mg/kg significantly reduced the number of nicotine infusions when compared to vehicle treatment (26%, 28% and 31% inhibition, respectively). Doses of 1 and 5 mg/kg were without effect (FIG. 5).

Compound of Example 5 was tested in a study using 4 independent groups. Each group received either oral vehicle or 1 of the 3 doses of compound of Example 5 (5, 10 or 30 mg-eq/kg). The 2 higher doses of compound of Example 5 (10 and 30 mg-eq/kg) significantly reduced the number of nicotine infusions when compared to vehicle treatment (51% and 68% inhibition, respectively). The 5 mg/kg dose was ineffective.

Chronic Treatment

Figure 7:
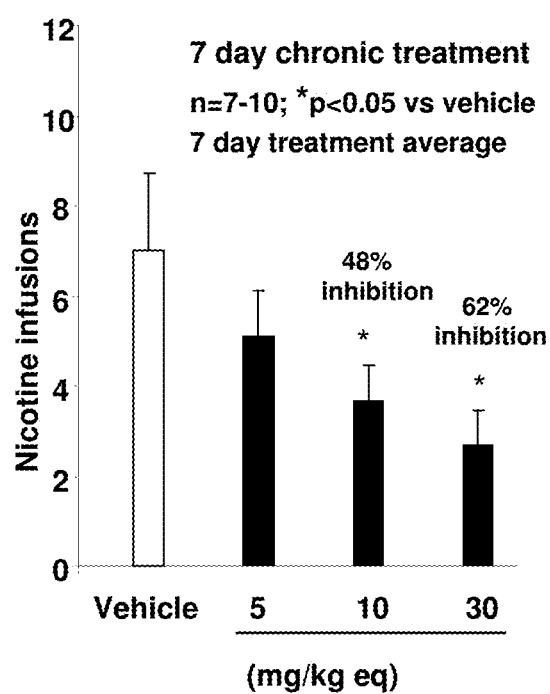
FIG. 7 shows significantly reduced nicotine self administration in rats chronically administered oral doses of a compound of the invention compared to vehicle.

Upon completion of the acute compound of Example 5 treatment study, the same animals were used to test the effect of 7-day chronic oral administration of compound of Example 5 in the nicotine self administration model. Rats were treated orally with compound of Example 5 (5, 10 or 30 mg-eq/kg) or vehicle 1 hr before nicotine self administration session for 7 consecutive days. Compound of Example 5 at 10 and 30 mg-eq/kg significantly reduced the number of nicotine infusions when compared to vehicle treatment during the 7 days of chronic oral administration (48% and 62% inhibition, respectively). Similar to the acute treatment, the 5 mg-eq/kg dose was ineffective (FIG. 7). There was no development of tolerance to the therapeutic effect during the course of the study (data not shown). Animals in nicotine self administration studies had to reach pre defined criteria (e.g. rat strain, minimum number of nicotine infusions, consistent baseline nicotine self administration throughout the study, patent iv catheters, etc.) to be included in analysis.

What is claimed is:

1. A method of treating obesity comprising administering a compound of Formula (Ia):

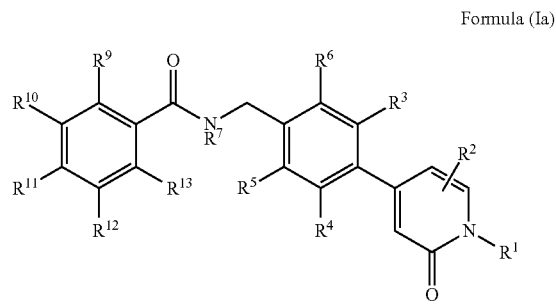

Formula (Ia)

wherein:

$R^1$ is hydrogen, optionally substituted $C_{1-6}$ alkyl, —$CH_2OH$, —$CH_2OP(O)(OR^{20})(OR^{21})$, —$C(O)R^{22}$, or —$SO_2R^{23}$;

$R^2$ is hydrogen, optionally substituted $C_{1-6}$ alkyl, cycloalkyl, or halo;

each of $R^3$, $R^4$, $R^5$, $R^6$, $R^9$, $R^{10}$, $R^{11}$, $R^{12}$ and $R^{13}$ is independently hydrogen, hydroxyl, —$OP(O)(OR^{20})(OR^{21})$, —$CH_2OH$, —$CH_2OP(O)(OR^{20})(OR^{21})$, optionally substituted alkyl, optionally substituted alkylene, optionally substituted alkynyl, optionally substituted alkoxy, optionally substituted cycloalkyl, aminocarbonyl, acyl, acylamino, —O—($C_1$ to $C_6$-alkyl)-O—($C_1$ to $C_6$-alkyl), cyano, halo, —$SO_2NR^{24}R^{25}$, or —$NR^{24}R^{25}$;

$R^7$ is hydrogen or optionally substituted $C_{1-6}$ alkyl;

each of $R^{20}$ and $R^{21}$ is independently $Na^+$, $Li^+$, $K^+$, hydrogen, or $C_{1-6}$ alkyl; or $R^{20}$ and $R^{21}$ can be combined to represent a single divalent cation $Zn^{2+}$, $Ca^{2+}$, or $Mg^{2+}$;

each of $R^{22}$ and $R^{23}$ is independently optionally substituted alkyl, optionally substituted alkoxy, optionally substituted cycloalkyl, optionally substituted aryl, or —$NR^{24}R^{25}$; and each of $R^{24}$ and $R^{25}$ is independently hydrogen or $C_{1-6}$ alkyl or when combined together with the nitrogen to which they are attached form a heterocycle; or a pharmaceutically acceptable salt or prodrug thereof, to a human patient in need thereof.

2. A method of treating obesity comprising administering a compound selected from the group consisting of:

2,6-dichloro-4-(2-methoxyethoxy)-N-(4-(2-oxo-1,2-dihydropyridin-4-yl) benzyl)benzamide;

2,6-dichloro-N-[4-(2-oxo-1,2-dihydro-pyridin-4-yl)-benzyl]-benzamide;

2-chloro-3-fluoro-N-(4-(2-oxo-1,2-dihydropyridin-4-yl) benzyl)benzamide;

2-chloro-6-methyl-N-(4-(2-oxo-1,2-dihydropyridin-4-yl) benzyl)benzamide;

2,6-dimethyl-N-(4-(2-oxo-1,2-dihydropyridin-4-yl)benzyl)benzamide;

2,6-dichloro-N-[4-(6-methyl-2-oxo-1,2-dihydro-pyridin-4-yl)-benzyl]-benzamide;

2-chloro-3,6-difluoro-N-(4-(2-oxo-1,2-dihydropyridin-4-yl)benzyl)benzamide;

2,6-dichloro-N-(3-methyl-4-(2-oxo-1,2-dihydropyridin-4-yl)benzyl)benzamide);
2,6-dichloro-N-(4-(1-methyl-2-oxo-1,2-dihydropyridin-4-yl)benzyl)benzamide;
2,6-difluoro-N-(4-(2-oxo-1,2-dihydropyridin-4-yl)benzyl)benzamide;
2-chloro-6-fluoro-N-(4-(2-oxo-1,2-dihydropyridin-4-yl)benzyl)benzamide;
2,6-dichloro-N-(2-fluoro-4-(2-oxo-1,2-dihydropyridin-4-yl)benzyl)benzamide;
2,6-dichloro-N-(4-(5-fluoro-2-oxo-1,2-dihydropyridin-4-yl)benzyl)benzamide; and
phosphoric acid mono-(4-{4-[(2,6-dichloro-benzoylamino)-methyl]-phenyl}-2-oxo-2H-pyridin-1-ylmethyl) ester; or
a pharmaceutically acceptable salt, single stereoisomer, mixture of stereoisomers, or tautomer thereof, to a patient in need thereof.

3. The method of claim 1 wherein the compound is:

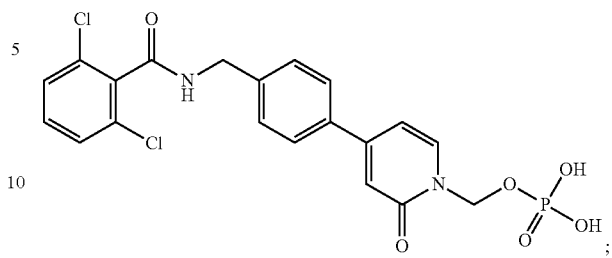

or a pharmaceutically acceptable salt, ester, or tautomer thereof.

* * * * *